United States Patent
Strano et al.

(10) Patent No.: US 11,208,628 B2
(45) Date of Patent: Dec. 28, 2021

(54) NANOBIONIC ENGINEERING OF ORGANELLES AND PHOTOSYNTHETIC ORGANISMS

(71) Applicants: Michael S. Strano, Lexington, MA (US); Juan Pablo Giraldo Gomez, Somerville, MA (US); Sean Mitchell Faltermeier, Cambridge, MA (US); Markita P. Landry, Cambridge, MA (US)

(72) Inventors: Michael S. Strano, Lexington, MA (US); Juan Pablo Giraldo Gomez, Somerville, MA (US); Sean Mitchell Faltermeier, Cambridge, MA (US); Markita P. Landry, Cambridge, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 197 days.

(21) Appl. No.: 14/454,196

(22) Filed: Aug. 7, 2014

(65) Prior Publication Data

US 2015/0047074 A1 Feb. 12, 2015

Related U.S. Application Data

(60) Provisional application No. 61/903,520, filed on Nov. 13, 2013, provisional application No. 61/864,166, filed on Aug. 9, 2013.

(51) Int. Cl.

| | |
|---|---|
| *C12N 5/04* | (2006.01) |
| *A01H 5/00* | (2018.01) |
| *C12N 15/82* | (2006.01) |
| *A01H 3/00* | (2006.01) |
| *G01N 33/52* | (2006.01) |
| *C12N 15/87* | (2006.01) |

(52) U.S. Cl.
CPC .......... *C12N 5/04* (2013.01); *A01H 3/00* (2013.01); *A01H 5/00* (2013.01); *C12N 15/8207* (2013.01); *C12N 15/8212* (2013.01); *C12N 15/8214* (2013.01); *C12N 15/8269* (2013.01); *G01N 33/52* (2013.01); *C12N 15/87* (2013.01)

(58) Field of Classification Search
None
See application file for complete search history.

(56) References Cited

U.S. PATENT DOCUMENTS

| | | | |
|---|---|---|---|
| 7,534,453 B1* | 5/2009 | Rzigalinski | A01N 1/02 424/617 |
| 8,795,733 B1 | 8/2014 | Perez et al. | |
| 2008/0023396 A1 | 1/2008 | Fugetsu et al. | |
| 2011/0045081 A1 | 2/2011 | Steitz et al. | |
| 2012/0107800 A1* | 5/2012 | Subramanian | A61K 49/0067 435/6.1 |
| 2012/0244569 A1 | 9/2012 | Samuel et al. | |

FOREIGN PATENT DOCUMENTS

| | | |
|---|---|---|
| WO | 2013/033513 A1 | 3/2013 |
| WO | 2013/192310 A1 | 12/2013 |

OTHER PUBLICATIONS

Yuan et al., 2011, Nanoscale Res. Lett. 6: 44.*
Standard Reference Material® 2483 data on SWCN CAS No. 308068-56-6 (NIST SRM 2483).*
Eastman et al., 1997, Biochimica et Biophysica Acta 1325: 41-62.*
Khodakovskaya et al., 2011, Proc. Natl. Acad. Sci. USA 108: 1028-1033.*
Salata, 2004, Journal of Nanobiotechnology DOI: 10.1186/1477-3155-2-3.*
Ilani and Mceuen, 2010, Annual Review of Condensed Matter Physics 1: 1-25.*
Pogodin et al., 2011, ACS Nano 5: 1141-1146.*
Ma et al., 2012, ACS Nano. 6: 10486-10496.*
Liu et al., 2009, Nano Lett. 9: 1007-1010.*
Calkins et al., 2013, High photo-electrochemical activity of thylakoid-carbon nanotube composites for photosynthetic energy conversion, Energy & Environmental Science 6: 1891-1900, with supplementary material.*
Shi et al., 2011, Cell entry of one-dimensional nanomaterials occurs by tip recognition and rotation, Nature Nanotechnology 6: 714-719, with supplementary information.*
Liu et al., 2009, Carbon Nanotubes as Molecular Transporters for Walled Plant Cells, Nano Letters 9: 1007-1010, with supplementary information.*
Reuel et al., 2012, Three-Dimensional Tracking of Carbon Nanotubes within Living Cells, ACS Nano 6: 5420-5428.*
Chen, 2012, Understanding nanoparticle-cell interaction, PhD thesis, Clemson University, pp. 1-166.*
Ghosh, 2009, Tailoring the surface-coating of gold nanoparticles for bio-applications, PhD thesis, University of Massachusetts Amherst, pp. 1-125.*
International Search Report dated Nov. 19, 2014, issued in International Application No. PCT/US2014/050127.
Written Opinion of the International Searching Authority dated Nov. 19, 2014, issued in International Application No. PCT/US2014/050127.
Notification of Transmittal of The International Search Report and The Written Opinion of the International Searching Authority, or The Declaration dated Nov. 19, 2014, issued in International Application No. PCT/US2014/050127.

* cited by examiner

*Primary Examiner* — Bratislav Stankovic
(74) *Attorney, Agent, or Firm* — Honigman LLP

(57) ABSTRACT

In one aspect, a composition can include an organelle, and a nanoparticle having a zeta potential of less than −10 mV or greater than 10 mV contained within the organelle. In a preferred embodiment, the organelle can be a chloroplast and the nanoparticle can be a single-walled carbon nanotube associated with a strongly anionic or strongly cationic polymer.

29 Claims, 56 Drawing Sheets

| Time | Treatment | PAA-NC (μM) | | | SWNT-NC (mg/L) | | | SWNT (mg/L) | | | m-SWNT (mg/L) | | |
|---|---|---|---|---|---|---|---|---|---|---|---|---|---|
| | | 4 | 8 | 17 | 0.7 | 1.4 | 2.8 | 0.7 | 1.4 | 2.8 | 0.7 | 1.4 | 2.8 |
| 30 min | Chloroplasts | 1.90 | 6.01 | 9.03 | 11.32 | 14.30 | 16.72 | 16.59 | 21.03 | 25.74 | 11.85 | 14.46 | 18.33 |
| | Buffer | 4.30 | 4.65 | 5.33 | 0.94 | 3.81 | 1.80 | 1.76 | 1.84 | 1.64 | 0.37 | 2.16 | 1.45 |
| 6 hrs | Chloroplasts | -3.49 | -3.01 | -5.80 | 4.03 | 8.54 | 12.66 | 14.74 | 15.02 | 16.53 | 9.59 | 7.71 | 8.40 |
| | Buffer | 1.71 | 1.26 | 0.92 | 4.42 | 4.73 | 4.41 | 7.21 | 5.02 | 4.08 | 5.38 | 1.77 | 2.54 |

FIGURE 39

NANOBIONIC ENGINEERING OF ORGANELLES AND PHOTOSYNTHETIC ORGANISMS

CLAIM OF PRIORITY

This application claims the benefit of prior U.S. Provisional Application No. 61/903,520 filed on Nov. 13, 2013, and provisional U.S. Patent Application No. 61/864,166, filed Aug. 9, 2013, each of which is incorporated by reference in its entirety.

FEDERAL SPONSORSHIP

This invention was made with Government support under Grant No. DBI-1103600 awarded by the National Science Foundation and under Contract No. DE-FG02-08ER46488 awarded by the Department of Energy. The government has certain rights in the invention.

FIELD OF INVENTION

This invention relates to nanobionic engineering of organelles and photosynthetic organisms.

BACKGROUND

A eukaryotic cell is a cell that contains membrane-bound organelles, most notably a nucleus. An organelle is a specialized subunit within a cell that has a specific function, and can be separately enclosed within its own lipid bilayer. Examples of organelles include mitochondria, chloroplasts, Golgi apparatus, endoplasmic reticulum, and as previously mentioned, the nucleus. Organelles are found within the cell cytoplasm, an intracellular fluid that is separated from extracellular fluid by the plasma membrane. The plasma membrane is a double layer (i.e., a bilayer) of phospholipids that permits only certain substances to move in and out of the cell.

In addition to these features, plant cells include specialized organelles that are not generally found in animal cells. For example, plant cells include a rigid cell wall. Plant cells also include chloroplasts. Chloroplasts are chlorophyll-containing double-membrane bound organelles that perform photosynthesis. Chloroplasts are believed to be descendants of prokaryotic cells (e.g., cyanobacteria) that were engulfed by a eukaryotic cell.

SUMMARY OF THE INVENTION

In one aspect, a composition can include a nanoparticle and an organelle.

In another aspect, a composition can include a nanoparticle and a photocatalytic unit.

In another aspect, a method for monitoring activity in an organelle can include introducing a nanoparticle into an organelle. Preferably, a photoluminescent nanoparticle can be introduced into an organelle.

In some embodiments, a method can include measuring a photoluminescence emission of the photoluminescent nanoparticle at a first time point. In some cases, a method can include measuring a photoluminescence emission of the photoluminescent nanoparticle at a second time point. In some cases, a method can include measuring the photoluminescence emission of the photoluminescent nanoparticle at a plurality of time points.

In some embodiments, a method can include comparing the photoluminescence emission measured at the first time point to the photoluminescence emission measured at the second time point. A change in the photoluminescence emission between the first time point and the second time point can indicate a change in a stimulus within the organelle. A change in the photoluminescence emission can include a change in photoluminescence intensity, a change in peak wavelength, a Raman shift, or a combination thereof.

In another aspect, a method for reducing reactive oxygen species in an organelle can include coupling at least one cerium oxide nanoparticle to a nanoparticle to form a nanoparticle conjugate. In some embodiments, a method can include exposing an organelle to the nanoparticle conjugate.

In another aspect, a method of delivering a material into an organelle can include coupling the material to a nanoparticle to form a material-nanoparticle conjugate. In some embodiments, a method can include exposing an organelle to the material-nanoparticle conjugate.

In some embodiments of the above aspects, a nanoparticle can be strongly anionic or strongly cationic. The nanoparticle can have a zeta potential of less than −10 mV or greater than 10 mV. In preferred embodiments, the nanoparticle can have a zeta potential of less than −20 mV or greater than 20 mV, a zeta potential of less than −30 mV or greater than 30 mV, or a zeta potential of less than −40 mV or greater than 40 mV.

In some embodiments, a composition can include an organelle, for example, a nucleus, endoplasmic reticulum, Golgi apparatus, chloroplast, chromoplast, gerontoplast, leucoplast, lysosome, peroxisome, glyoxysome, endosome or vacuole. In a preferred embodiment, an organelle is a chloroplast. In some embodiments, a nanoparticle can be contained within the organelle.

In some embodiments, a photocatalytic can be a structure capable of performing photosynthesis or photocatalysis. For example, a photocatalytic unit can be a chloroplast, a cyanobacteria, or a bacterial species selected from the group consisting of Chlorobiacea spp., a Chromaticacea spp. and a Rhodospirillacae spp. In some cases, a photocatalytic unit can include an outer lipid membrane. In some embodiments, a nanoparticle can be contained within the outer lipid membrane of the photocatalytic unit.

In some embodiments, a nanoparticle can be associated with a thylakoid membrane within a chloroplast.

In a preferred embodiment, a composition can include an organelle, and a nanoparticle having a zeta potential of less than −10 mV or greater than 10 mV contained within the organelle.

In a preferred embodiment, a composition can include a photocatalytic unit including an outer lipid membrane, and a nanoparticle having a zeta potential of less than −10 mV or greater than 10 mV contained within the outer lipid membrane of the photocatalytic unit.

In some embodiments, a nanoparticle can include a nanotube. In some cases, a nanotube can be a carbon nanotube, or more preferably, a single-walled carbon nanotube.

In some embodiments, a nanoparticle can include a metal oxide. For example, a nanoparticle can include cerium oxide. In some embodiments, a nanoparticle can be conjugated with at least one cerium oxide nanoparticle. Conjugation can be direct or indirect. Conjugation can also be through a covalent bond, ionic bond or Van der Waals interaction. In some cases, a nanoparticle can be cross-linked with at least one cerium oxide nanoparticle.

In some embodiments, a nanoparticle can include a polymer. In some cases, the polymer can include a polynucleotide, for example, poly(AT). In some cases, the polymer can include a polysaccharide. The polysaccharide can include dextran, pectin, hyaluronic acid, chitosan, or hydroxyethylcellulose. In some cases, the polymer can include poly(acrylic acid). In some cases, the polymer of the nanoparticle can be cross-linked with at least one cerium oxide nanoparticle.

In some embodiments, any lipids associated with a nanoparticle originated in the organelle. In some cases, a nanoparticle outside an organelle or photocatalytic unit is free of lipids. In some cases, any lipids associated with a nanoparticle became associated with the nanoparticle when the nanoparticle was introduced into an organelle or photocatalytic unit.

In some embodiments, a nanoparticle can be photoluminescent. In a preferred embodiment, a nanoparticle can emit near-infrared radiation.

In a preferred embodiment, a nanoparticle can absorb light over a broad range of wavelengths. For example, a nanoparticle can absorb light over the ultraviolet, visible, near infrared spectra, or combinations thereof.

In some embodiments, the photoluminescence emission of the photoluminescent nanoparticle can be altered by a change in a stimulus within the organelle. In some cases, the stimulus can be the pH of the organelle. In some cases, the stimulus can be the concentration of an analyte. An analyte can include a reactive oxygen species, nitric oxide, carbon dioxide, adenosine triphosphate, nicotinamide adenine dinucleotide phosphate, oxygen, or nitroaromatic compounds.

In some embodiments, the photoluminescence can be detected from a distance, for example, a several meters, tens of meters or hundreds of meters away. In some embodiments, the photoluminescence can be detected from a satellite.

In some embodiments, a nanoparticle can be a semiconductor.

In some embodiments, a composition can be in a green plant, tissues of a green plant, or a cell of a green plant. In some embodiments, a composition can be immobilized with a light emitting compound, for example, luciferase, in a green plant.

The details of one or more embodiments of the invention are set forth in the accompanying drawings and description below. Other features, objects and advantages of the invention will be apparent from the description and drawings and from the claims.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 4($a$) includes visible images. FIG. 4($b$) includes nIR images. FIG. 4($c$) includes nIR images.

FIG. 5($a$) is a graph of the fluorescence from ss(AT)15-SWNTs, FIG. 5($b$) is a graph of the fluorescence from PVA-SWNTs, FIG. 5($c$) is a graph of the fluorescence from Chitosan-SWNTs and FIG. 5($d$) is a graph of the fluorescence from lipid-SWNTs.

FIG. 10($a$) includes visible and nIR images of nanoparticles and lamina. FIG. 10($b$) includes visible and nIR images of nanoparticles and a plant vein. FIG. 10($c$) includes visible and nIR images of nanoparticles and cross-sections of parenchyma cells. FIG. 10($d$) includes visible and nIR images of nanoparticles and chloroplasts. FIG. 10($e$) is a graph of nIR signal of CoMoCAT SWNTs in leaves relative to SWNTs in solution. FIG. 10($f$) is a graph of emission intensity as a function of emission wavelength. FIG. 10($g$) is a graph showing temporal patters of chlorophyll absorbance.

FIG. 23(a) includes CRi Maestro nIR images of leaf lamina. FIG. 23(b) includes images of leaf veins at 20× magnification, FIG. 23(c) includes images of parenchyma cells with chloroplasts at 20× magnification, and FIG. 23(d) includes images of chloroplasts in vivo at 63× magnification. Laser excitation was 785 nm.

FIG. 39 is a table including a comparison of DCPIP (μM) change between chloroplasts with nanoparticles minus chloroplasts without nanoparticles vs. DCPIP reduced by nanoparticles in buffer after 30 minutes and 6 hrs.

DETAILED DESCRIPTION

Figure 1:
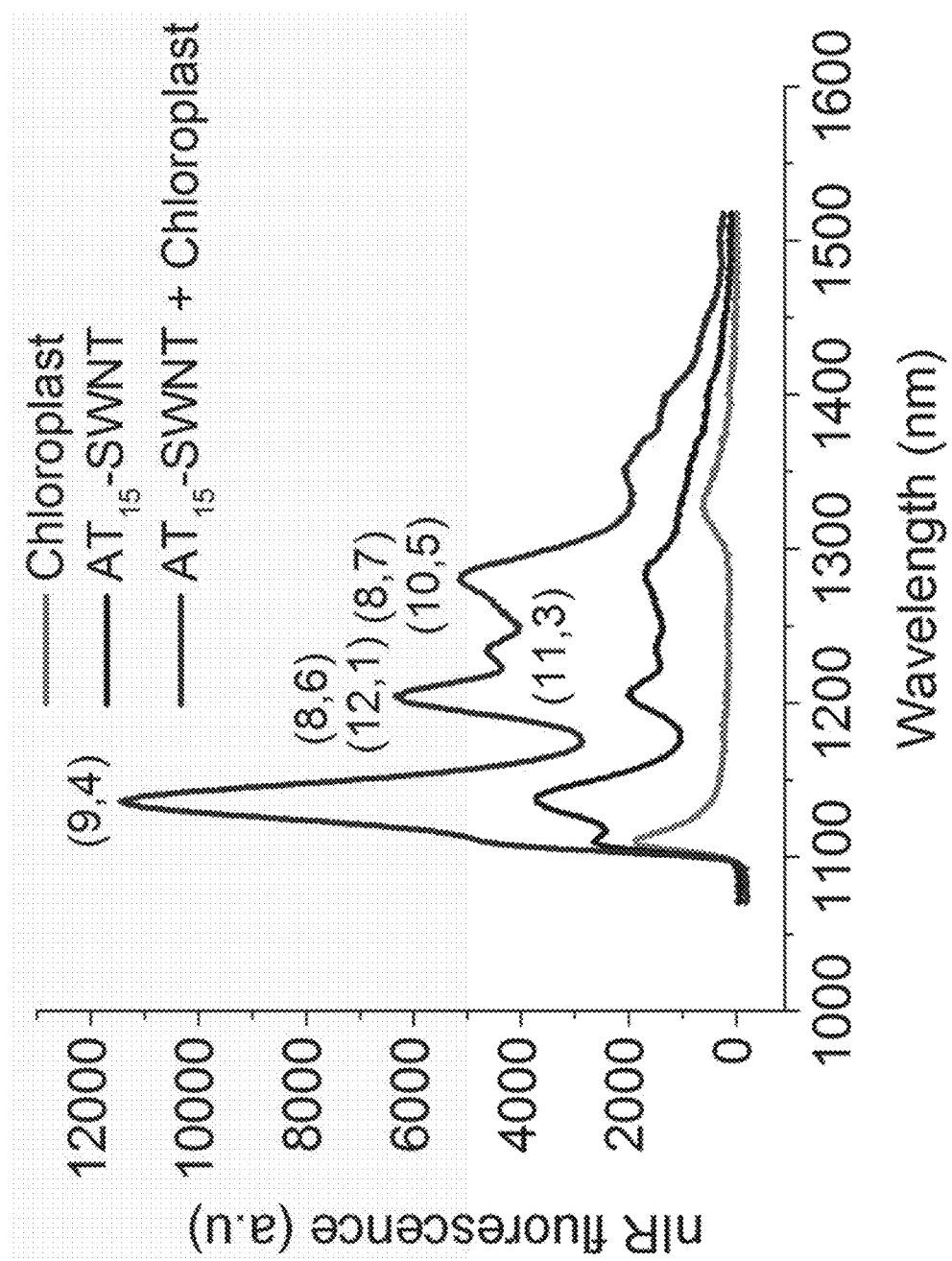
FIG. 1 is a graph showing nIR fluorescence of chloroplasts and SWNTs. Chloroplast autofluorescence was masked from nIR images by a long pass 1100 nm filter.

As used herein, the term "nanoparticle" refers to articles having at least one cross-sectional dimension of less than about 1 micron. A nanoparticle can also be referred to as a "nanostructure." A nanoparticle can have at least one cross-sectional dimension of less than about 500 nm, less than about 250 nm, less than about 100 nm, less than about 75 nm, less than about 50 nm, less than about 25 nm, less than about 10 nm, or, in some cases, less than about 1 nm. Examples of nanoparticle include nanotubes (e.g., carbon nanotubes), nanowires (e.g., carbon nanowires), graphene, and quantum dots, among others. In some embodiments, the nanoparticle can include a fused network of atomic rings, the atomic rings comprising a plurality of double bonds.

A nanoparticle can be a photoluminescent nanoparticle. A "photoluminescent nanoparticle," as used herein, refers to a class of nanoparticles that are capable of exhibiting photoluminescence. In some cases, photoluminescent nanoparticles can exhibit fluorescence. In some instances, photoluminescent nanoparticles exhibit phosphorescence. Examples of photoluminescent nanoparticles suitable for use include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, and graphene, among others.

A variety of nanoparticles can be used. Sometimes a nanoparticle can be a carbon-based nanoparticle. As used herein, a "carbon-based nanoparticle" can include a fused network of aromatic rings wherein the nanoparticle includes primarily carbon atoms. In some instances, a nanoparticle can have a cylindrical, pseudo-cylindrical, or horn shape. A carbon-based nanoparticle can include a fused network of at least about 10, at least about 50, at least about 100, at least about 1000, at least about 10,000, or, in some cases, at least about 100,000 aromatic rings. A carbon-based nanoparticle may be substantially planar or substantially non-planar, or may include a planar or non-planar portion. A carbon-based nanoparticle may optionally include a border at which the fused network terminates. For example, a sheet of graphene includes a planar carbon-containing molecule including a border at which the fused network terminates, while a carbon nanotube includes a non-planar carbon-based nanoparticle with borders at either end. In some cases, the border may be substituted with hydrogen atoms. In some cases, the border may be substituted with groups comprising oxygen atoms (e.g., hydroxyl).

In some embodiments, a nanoparticle can include or be a nanotube. The term "nanotube" is given its ordinary meaning in the art and can refer to a substantially cylindrical molecule or nanoparticle including a fused network of primarily six-membered rings (e.g., six-membered aromatic rings). In some cases, a nanotube can resemble a sheet of graphite formed into a seamless cylindrical structure. It should be understood that a nanotube may also include rings or lattice structures other than six-membered rings. Typically, at least one end of the nanotube may be capped, i.e., with a curved or non-planar aromatic group. A nanotube may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may include a carbon nanotube. The term "carbon nanotube" can refer to a nanotube including primarily carbon atoms. Examples of carbon nanotubes can include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, a carbon nanotube can be a single-walled carbon nanotube. In some cases, a carbon nanotube can be a multi-walled carbon nanotube (e.g., a double-walled carbon nanotube).

In some embodiments, a nanoparticle can include non-carbon nanoparticles, specifically, non-carbon nanotubes. Non-carbon nanotubes may be of any of the shapes and dimensions outlined above with respect to carbon nanotubes. A non-carbon nanotube material may be selected from polymer, ceramic, metal and other suitable materials. For example, a non-carbon nanotube may include a metal such as Co, Fe, Ni, Mo, Cu, Au, Ag, Pt, Pd, Al, Zn, or alloys of these metals, among others. In some instances, a non-carbon nanotube may be formed of a semi-conductor such as, for example, Si. In some cases, a non-carbon nanotube may include a Group II-VI nanotube, wherein Group II includes Zn, Cd, and Hg, and Group VI includes O, S, Se, Te, and Po. In some embodiments, a non-carbon nanotube may include a Group III-V nanotube, wherein Group III includes B, Al, Ga, In, and Tl, and Group V includes N, P, As, Sb, and Bi. As a specific example, a non-carbon nanotube may include a boron-nitride nanotube. In other embodiments, the nanoparticle can be a ceramic, for example, a metal oxide, metal nitride, metal boride, metal phosphide, or metal carbide. In this example, the metal can be any metal, including Group I metal, Group II metal, Group III metal, Group IV metal, transition metal, lanthanide metal or actinide metal. For example, the ceramic can include one or more of metal, for example, Li, Na, K, Rb, Cs, Be, Mg, Ca, Sr, Ba, Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os, Co, Rh, Ir, Ni, Pd, Pt, Cu, Ag, Su, Zn, Cd, Hg, Al, Ga, In, Tl, Si, Ge, Sn, Pb or Bi.

In some embodiments, a nanotube may include both carbon and another material. For example, in some cases, a multi-walled nanotube may include at least one carbon-based wall (e.g., a conventional graphene sheet joined along a vector) and at least one non-carbon wall (e.g., a wall comprising a metal, silicon, boron nitride, etc.). In some embodiments, the carbon-based wall may surround at least one non-carbon wall. In some instances, a non-carbon wall may surround at least one carbon-based wall.

The term "quantum dot" is given its normal meaning in the art and can refer to semi-conducting nanoparticles that exhibit quantum confinement effects. Generally, energy (e.g., light) incident upon a quantum dot can excite the quantum dot to an excited state, after which, the quantum dot can emit energy corresponding to the energy band gap between its excited state and its ground state. Examples of materials from which quantum dots can be made include PbS, PbSe, CdS, CdSe, ZnS, and ZnSe, among others.

A photoluminescent nanoparticle can be, in some cases, substantially free of dopants, impurities, or other non-nanoparticle atoms. For example, in some embodiments, a nanoparticle can include a carbon nanoparticle that is substantially free of dopants. As a specific example, in some embodiments, a nanoparticle can include single-walled carbon nanotube that contains only aromatic rings (each of which contains only carbon atoms) within the shell portion of the nanotube. In other words, a nanoparticle can consist essentially of a single material, for example, carbon.

In some embodiments, a photoluminescent nanoparticle may emit radiation within a desired range of wavelengths. For example, in some cases, a photoluminescent nanoparticle may emit radiation with a wavelength between about 750 nm and about 1600 nm, or between about 900 nm and about 1400 nm (e.g., in the near-infrared range of wavelengths). In some embodiments, a photoluminescent nanoparticle may emit radiation with a wavelength within the visible range of the spectrum (e.g., between about 400 nm and about 700 nm).

In some embodiments, a photoluminescent nanoparticle may be substantially free of covalent bonds with other entities (e.g., other nanoparticles, a current collector, the surface of a container, a polymer, an analyte, etc.). The absence of covalent bonding between a photoluminescent nanoparticle and another entity may, for example, preserve the photoluminescent character of the nanoparticle. In some cases, single-walled carbon nanotubes or other photoluminescent nanoparticles may exhibit modified or substantially no fluorescence upon forming a covalent bond with another entity (e.g., another nanoparticle, a current collector, a surface of a container, and the like).

In some embodiments, a nanoparticle can include cerium oxide. A nanoparticle including cerium oxide can be referred to as nanoceria. A nanoparticle can be cerium oxide. A nanoparticle can also be conjugated to at least one cerium oxide nanoparticle. Conjugation can be direct or indirect. Conjugation can also be through a covalent bond, ionic bond or van der Waals interaction. A nanoparticle can be cross-linked with at least one cerium oxide nanoparticle, more specifically, cross-linked using via carbodiimide chemistry. In one example, a carbodiimide agent N-ethyl-N'-(3-dimethylaminopropyl) carbodiimide hydrochloride (EDAC) can be used.

A nanoparticle can be strongly cationic or anionic. Strongly cationic or anionic can mean that the nanoparticle (or other element) has a high magnitude of the zeta potential. For example, the nanoparticle can have a zeta potential of less than −10 mV or greater than 10 mV. In preferred embodiments, the nanoparticle can have a zeta potential of less than −20 mV or greater than 20 mV, a zeta potential of less than −30 mV or greater than 30 mV, or a zeta potential of less than −40 mV or greater than 40 mV.

Figure 50:
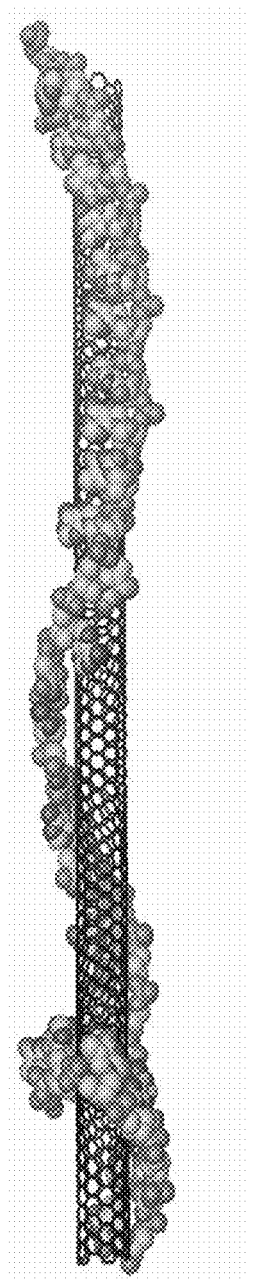
FIG. 50 is a schematic of a nanotube associated with a polymer.

A nanoparticle can include a coating or be suspended in a coating with a high magnitude of the zeta potential. A coating can be a polymer (see, e.g., FIG. 50). A variety of polymers may be used in association with the embodiments described herein. In some cases, the polymer may be a polypeptide. In some embodiments, the length and/or weight of the polypeptide may fall within a specific range. For example, the polypeptide may include, in some embodiments, between about 5 and about 50, or between about 5 and about 30 amino acid residues. In some cases, the polypeptide may have a molecular weight of between about 400 g/mol and about 10,000 g/mol, or between about 400 g/mol and about 600 g/mol. Examples of protein polymers can include glucose oxidase, bovine serum albumin and alcohol dehydrogenase.

A polymer may include a synthetic polymer (e.g., polyvinyl alcohol, poly(acrylic acid), poly(ethylene oxide), poly(vinyl pyrrolidinone), poly(allyl amine), poly(2-vinylpyridine), poly(maleic acid), and the like), in some embodiments.

In some embodiments, the polymer may include an oligonucleotide. The oligonucleotide can be, in some cases, a single-stranded DNA oligonucleotide. The single-stranded DNA oligonucleotide can, in some cases, include a majority (>50%) A or T nucleobases. In some embodiments, single-stranded DNA oligonucleotide can include more than 75%, more than 80%, more than 90%, or more than 95% A or T nucleobases. In some embodiments, the single-stranded DNA oligonucleotide can include a repeat of A and T. For example, a oligonucleotide can be, in some cases, at least 5, at least 10, at least 15, between 5 and 25, between 5 and 15, or between 5 and 10 repeating units, in succession, of (GT) or (AT). Repeating units can include at least 2 nucleobases, at least 3 nucleobases, at least 4 nucleobases, at least 5 nucleotides long. The nucleobases described herein are given their standard one-letter abbreviations: cytosine (C), guanine (G), adenine (A), and thymine (T).

In some embodiments, the polymer can include a polysaccharide such as, for example, dextran, pectin, hyaluronic acid, hydroxyethylcellulose, amylose, chitin, or cellulose.

In preferred embodiments, the interaction between a polymer and a nanoparticle can be non-covalent (e.g., via van der Waals interactions); however, a polymer can covalently bond with a nanoparticle. In some embodiments, the polymer may be capable of participating in a pi-pi interaction with the nanostructure. A pi-pi interaction (a.k.a., "pi-pi stacking") is a phenomenon known to those of ordinary skill in the art, and generally refers to a stacked arrangement of molecules adopted due to interatomic interactions. Pi-pi interactions can occur, for example, between two aromatic molecules. If the polymer includes relatively large groups, pi-pi interaction can be reduced or eliminated due to steric hindrance. Hence, in certain embodiments, the polymer may be selected or altered such that steric hindrance does not inhibit or prevent pi-pi interactions. One of ordinary skill in the art can determine whether a polymer is capable or participating in pi-pi interactions with a nanostructure.

The polymer may be strongly cationic or anionic, meaning that the polymer has a high magnitude of the zeta potential. For example, the polymer can have a zeta potential of less than −10 mV or greater than 10 mV, less than −20 mV or greater than 20 mV, less than −30 mV or greater than 30 mV, or less than −40 mV or greater than 40 mV.

A nanoparticle can be contained within a chloroplast, as demonstrated more fully herein. A nanoparticle can traverse and/or localize within the outer membrane layer (i.e., lipid bilayer). The process can be complete and/or irreversible. Because other organelles include an outer membrane layer (i.e., lipid bilayer), a nanoparticle can be contained within other organelles. For example, other organelles that a nanoparticle can be introduced into can include a nucleus, endoplasmic reticulum, Golgi apparatus, chloroplast, chromoplast, gerontoplast, leucoplast, lysosome, peroxisome, glyoxysome, endosome, mitochondria or vacuole.

Thylakoids are a membrane-bound compartment inside a chloroplast. Cyanobacteria can also include thylakoids. In some embodiments, a nanoparticle can be associated with a thylakoid membrane within a chloroplast, cyanobacteria or other photocatalytic cell or organelle.

A nanoparticle can be contained within a photocatalytic unit, most preferably, including an outer lipid membrane (i.e., lipid bilayer). A photocatalytic unit can be a structure capable of performing photosynthesis or photocatalysis, preferably a cell or an organelle capable of performing photosynthesis or photocatalysis. For example, a photocatalytic unit can be a chloroplast, a cyanobacteria, or a bacterial species selected from the group consisting of Chlorobiacea spp., a Chromaticacea spp. and a Rhodospirillacae spp.

An organelle can be part of a cell, a cell can be part of a tissue, and a tissue can be part of an organism. For example, a nanoparticle can be contained within a cell of a leaf of a plant. More to the point, a cell can be intact. In other words, the organelle may not be an isolated organelle, but rather, the organelle can be contained within the outer lipid membrane of a cell.

A nanoparticle that is independent of an organelle or cell can be free of lipids. An outer lipid membrane can enclose or encompass an organelle or cell. As the nanoparticle traverses the outer lipid membrane of an organelle or cell, lipids from the outer lipid membrane can associate or coat the nanoparticle. As a result, a nanoparticle inside the outer lipid membrane of an organelle or cell can be associated with or coated with lipids that originated in the organelle or cell.

Transport of a nanoparticle into an organelle or a cell can be a passive process. In some cases, transport across the outer lipid membrane can be independent of the temperature or light conditions.

Embedding a nanoparticle within an organelle or cell can be useful for monitoring the activity of the organelle or cell. For example, a nanoparticle, preferably a photoluminescent nanoparticle, can be introduced into the organelle or cell. Measurements of the photoluminescence of a photoluminescent nanoparticle can provide information regarding a stimulus within an organelle or cell. Measurements of the photoluminescence of a photoluminescent nanoparticle can be taken at a plurality of time points. A change in the photoluminescence emission between a first time point and a second time point can indicate a change in a stimulus within the organelle or cell.

In some embodiments, a change in the photoluminescence emission can include a change in the photoluminescence intensity, a change in an emission peak width, a change in an emission peak wavelength, a Raman shift, or combination thereof. One of ordinary skill in the art would be capable of calculating the overall intensity by, for example, taking the sum of the intensities of the emissions over a range of wavelengths emitted by a nanoparticle. In some cases, a nanoparticle may have a first overall intensity, and a second, lower overall intensity when a stimulus changes within the organelle or cell. In some cases, a nanoparticle may emit a first emission of a first overall intensity, and a second emission of a second overall intensity that is different from the first overall intensity (e.g., larger, smaller) when a stimulus changes within the organelle or cell.

A nanoparticle may, in some cases, emit an emission of radiation with one or more distinguishable peaks. One of ordinary skill in the art would understand a peak to refer to a local maximum in the intensity of the electromagnetic radiation, for example, when viewed as a plot of intensity as a function of wavelength. In some embodiments, a nanoparticle may emit electromagnetic radiation with a specific set of peaks. In some cases, a change in a stimulus may cause the nanoparticle to emit electromagnetic radiation including one or more peaks such that the peaks (e.g., the frequencies of the peaks, the intensity of the peaks) may be distinguishable from one or more peaks prior to the change in stimulus. In some cases, the change in a stimulus may cause the nanoparticle to emit electromagnetic radiation comprising one or more peaks such that peaks (e.g., the frequencies of the peaks, the intensity of the peaks) are distinguishable from the one or more peaks observed prior to the change in the stimulus. When the stimulus is the concentration of an analyte, the frequencies and/or intensities of the peaks may, in some instances, allow one to determine the analyte interacting with the nanoparticle by, for example, producing a signature that is unique to a particular analyte that is interacting with the nanoparticle. Determination of a specific analyte can be accomplished, for example, by comparing the properties of the peaks emitted in the presence of the analyte to a set of data (e.g., a library of peak data for a predetermined list of analytes).

A stimulus can include the pH of the organelle or cell. A change in the pH can be an increase or decrease in the pH.

A stimulus can include a modification of an analyte. For example, an analyte may be oxidized or reduced. In other examples, an analyte can be ionized. In another example, an analyte can include an ether, ester, acyl, or disulfide or other derivative.

A stimulus can include the concentration of an analyte. An analyte can include a reactive oxygen species, for example, hydrogen peroxide, superoxide, nitric oxide, and a peroxidase. Alternatively, an analyte can be carbon dioxide, adenosine triphosphate (ATP), nicotinamide adenine dinucleotide phosphate ($NADP^+$ or NADPH), or oxygen. In some instances, the concentration of the analyte may be relatively low (e.g., less than about 100 micromolar, less than about 10 micromolar, less than about 1 micromolar, less than about 100 nanomolar, less than about 10 nanomolar, less than about 1 nanomolar, or about a single molecule of the analyte). In some cases, the concentration of an analyte may be zero, indicating that no analyte is present.

Functionalized nanotubes can be useful in many areas. In one embodiment, nanotubes can be functionalized in different ways to serve as sensors for harmful compounds. To detect explosives, bombolitin-functionalized nanotubes can be infused into the leaves of the plant. Bombolitin is a unique peptide which allows for recognition of nitroaromatics, the key compounds in many explosives. Therefore, a plant with bombolitin-functionalized nanoutbes can recognize the nitroaromatics from explosives. Using stand-off devices for detecting the spectral shift, semiconducting SWNT and SWNT-based sensors within plants can be imaged from a distance of several meters to hundreds of metters, for example, from 3-10 meters, 10-40 meters, 40-100 meters, 100-500 meters, or 500-1000 meters, and even from a satellite.

A light emitting compound immobilized on nanoparticles can be introduced to a green plant to make an autoluminescent plant. In one embodiment, co-immobilization of luciferase and luciferin on mesoporous silica nanoparticles can make autoluminescent plants without genetic modification. Immobilizing luciferase on silica nanoparticles with ATP in plant leaves can make the luminescence reactions to glow for longer time durations compared to free luciferase in a leaf.

Figure 48:
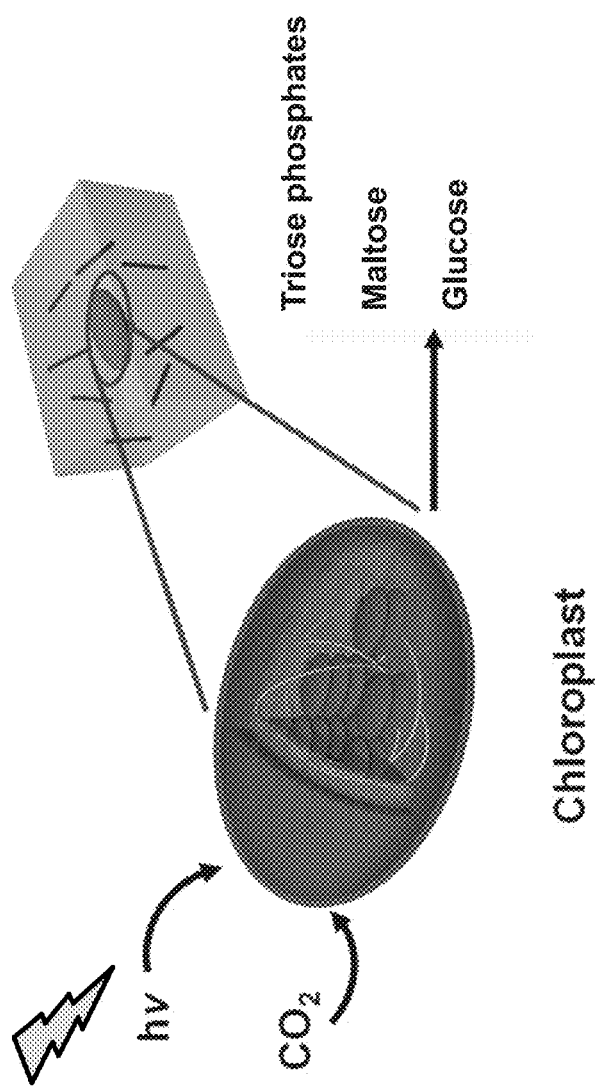
FIG. 48 is a schematic of a chloroplast performing photosynthesis.

Chloroplasts can be considered a high source of chemical energy in food supplies and carbon-based fuels on the planet. By capturing atmospheric $CO_2$, these plant organelles convert light energy into three major forms of sugars that fuel plant growth: maltose, triose phosphate and glucose (FIG. 48). (Weise, S. E., Weber, A. P. M. & Sharkey, T. D. Maltose is the major form of carbon exported from the chloroplast at night. *Planta* 218, 474-82 (2004), which is incorporated by reference in its entirety). While some information exists on the interface between photosystems and nanomaterials, nanoengineering chloroplast photosynthesis for enhancing solar energy harnessing remains unexplored. (Boghossian, A. A. et al. Application of Nanoparticle Antioxidants to Enable Hyperstable Chloroplasts for Solar Energy Harvesting. *Adv. Energy Mater.* 3:7, p. 881-893 (2013), which is incorporated by reference in its entirety). One deterrent in using chloroplast photosynthetic power as an alternative energy source can be that these organelles are no longer independently living organisms. However, isolated chloroplasts from the algae *Vaucheria litorea* in symbiotic association with the sea slug *Elysia chlorotica* remarkably can remain functional for at least 9 months. (Trench, R. K., Boyle, J. E. & Smith, D. C. The Association between Chloroplasts of Codium fragile and the Mollusc *Elysia viridis*. I. Characteristics of Isolated Codium Chloroplasts. *Proc. R. Soc. B Biol. Sci.* 184, 51-61 (1973); and Rumpho, M. E., Summer, E. J. & Manhart, J. R. Solar-Powered Sea Slugs. Mollusc/Algal Chloroplast Symbiosis. 123, 29-38 (2000), each of which is incorporated by reference in its entirety). Land plant chloroplast photosystem activity can decline within a day after extraction, while ex vivo sugar output can last for only a few hours. (Weise, S. E., et al. (2004); Choe, H. & Thimann, K. The Senescence of Isolated Chloroplasts. *Planta* 121, 201-203 (1974); Green, B. J., Fox, T. C. & Rumpho, M. E. Stability of isolated algal chloroplasts that participate in a unique mollus/kleptoplast association. *Symbiosis* 40, 31-40 (2005); and Neuhaus, H. E. & Schulte, N. Starch degradation in chloroplasts isolated from C3 or CAM (crassulacean acid metabolism)-induced Mesembryanthemum crystallinum L. *Biochem. J.* 318, 945-53 (1996), each of which is incorporated by reference in its entirety). Although chloroplasts have mechanisms in place to self-repair photo-damaged proteins, a double-stranded circular DNA with a subset of protein-encoding genes involved in photosynthesis, and ribosomal units for protein synthesis and assembly, little is known about engineering these plant organelles for long-term, stable photosynthesis ex vivo. (Edelman, M. & Mattoo, A. K. D1-protein dynamics in photosystem II: the lingering enigma. *Photosynth. Res.* 98, 609-20 (2008); Schmitz-Linneweber, C. et al. The plastid chromosome of spinach (*Spinacia oleracea*): complete nucleotide sequence and gene organization. *Plant Mol. Biol.* 45, 307-15 (2001); and Marin-Navarro, J., Manuell, A. L., Wu, J. & P Mayfield, S. Chloroplast translation regulation. *Photosynth. Res.* 94, 359-74 (2007), each of which is incorporated by reference in its entirety). Another limitation of chloroplasts photosynthesis can be that absorbed light is constrained to the visible range of the spectrum, allowing access to only roughly 50% of the incident solar energy radiation. (Bolton, J. R. & Hall, D. Photochemical conversion and storage of solar energy. *Annu. Rev. Energy* 4, 353-401 (1979), which is incorporated by reference in its entirety). Furthermore, in some conditions, less than 10% of full sunlight saturates the capacity of the photosynthetic apparatus. (Zhu, X.-G., Long, S. P. & Ort, D. R. Improving photosynthetic efficiency for greater yield. *Annu. Rev. Plant Biol.* 61, 235-61 (2010), which is incorporated by reference in its entirety). Photosynthetic organisms appear to have evolved for reproductive success, including shading competitors, not for solar energy conversion efficiency. Thus improving photosynthetic efficiency may require extending the range of solar light absorption, particularly in the near infrared spectral range, which is able to penetrate deeper into living organisms. (Blankenship, R. E. et al. Comparing photosynthetic and photovoltaic efficiencies and recognizing the potential for improvement. *Science* 332, 805-9 (2011), which is incorporated by reference in its entirety).

Figure 49:
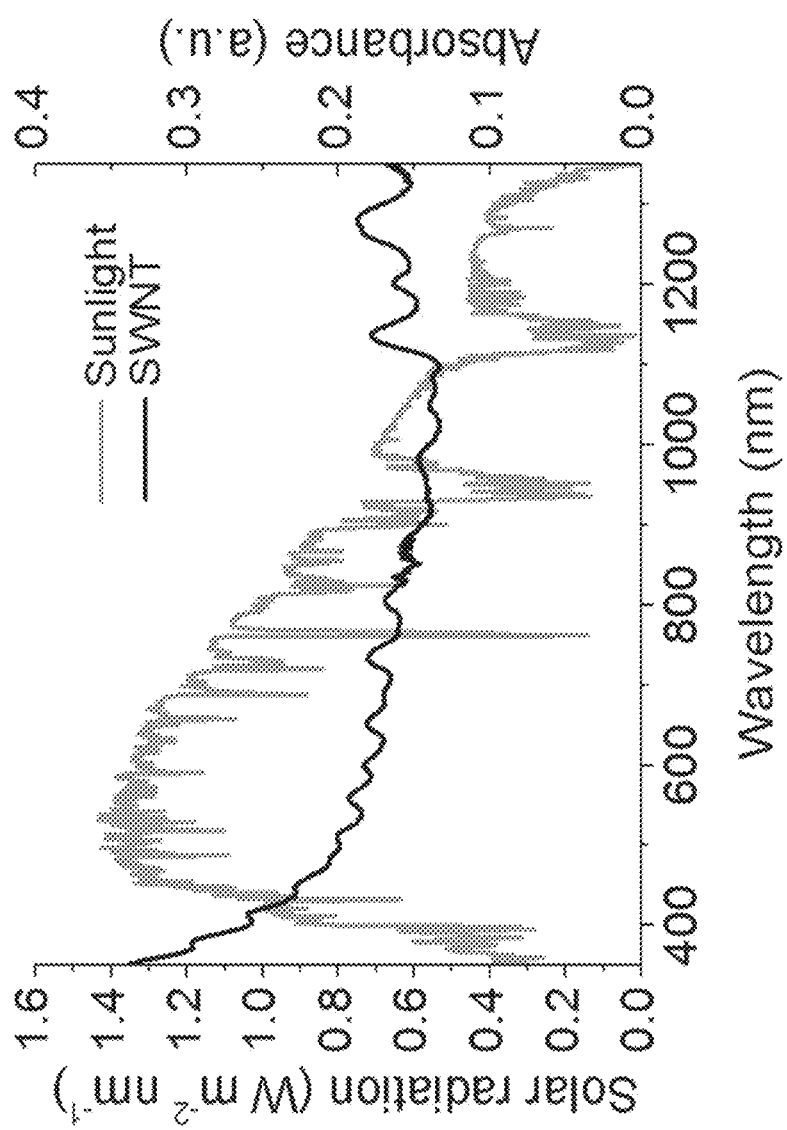
FIG. 49 is a graph representing absorption of solar spectrum light by SWNTs.
Figure 53:
FIG. 53A is a graph showing a response of a camera that can monitor emission from ~900 nm-1700 nm, which uses an InGaAs array.
FIG. 53B is a photograph of the FLIR SC6200.
FIG. 53C is a photograph showing the nIR emission of a 532 nm 200 mW laser shining through a vial of water.
FIG. 53D a photograph showing the nIR emission of a 532 nm 200 mW laser shining through a vial of 5 mg/L 6.5 SDS SWNT.
Figure 53:
Figure 53:
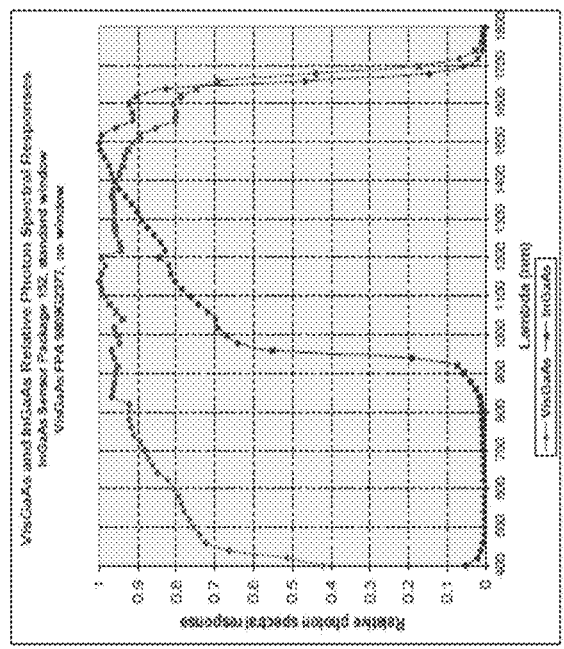
Figure 53:

The high stability and unique chemical and physical traits of nanomaterials have the potential to enable chloroplast-based photocatalytic complexes both ex vivo and in vivo with enhanced and novel functional properties. Single-walled carbon nanotubes ("SWNTs") embedded within chloroplasts have the potential to enhance the light reactions of photosynthesis with their distinctive optical and electronic properties. Under bright sunlight, chloroplast photosystems can capture more photons than they can convert into electron flow. (Wilhelm, C. & Selmar, D. Energy dissipation is an essential mechanism to sustain the viability of plants: The physiological limits of improved photosynthesis. *J. Plant Physiol.* 168, 79-87 (2011), which is incorporated by reference in its entirety). However, under non-saturating light conditions, maximizing solar energy capture can be crucial. (Scholes, G. D., Fleming, G. R., Olaya-Castro, A. & van Grondelle, R. Lessons from nature about solar light harvesting. *Nat. Chem.* 3, 763-774 (2011), which is incorporated by reference in its entirety). SWNTs can absorb light over a broad range of wavelengths in the ultraviolet, visible and nIR spectra not captured by the chloroplast antenna pigments (FIGS. 49 and 53). The electronic band gap of semiconducting SWNTs can allow them to convert this absorbed solar energy into excitons that could transfer electrons to the photosynthetic machinery. (Han, J.-H. et al. Exciton antennas and concentrators from core-shell and corrugated carbon nanotube filaments of homogeneous composition. *Nat. Mater.* 9, 833-9 (2010), which is incorporated by reference in its entirety). Also, SWNT-based nanosensors can monitor single-molecule dynamics of free radicals within chloroplasts for optimizing photosynthetic environmental conditions (light and $CO_2$). (Zhang, J. et al. Single Molecule Detection of Nitric Oxide Enabled by d(AT)(15) DNA Adsorbed to Near Infrared Fluorescent Single-Walled Carbon Nanotubes. *J. Am. Chem. Soc.* 20, 567-581 (2010), which is incorporated by reference in its entirety). However, nanoengineering photosynthesis can require the delivery of nanomaterials through the chloroplast outer envelope. Nanoparticle transport through lipid bilayers has been described to be energy dependent, requiring endocytosis pathways that have not been reported in isolated chloroplasts. (Shi, X., von dem Bussche, A., Hurt, R. H., Kane, A. B. & Gao, H. Cell entry of one-dimensional nanomaterials occurs by tip recognition and rotation. *Nat. Nanotechnol.* 6, 714-9 (2011), which is incorporated by reference in its entirety). To date, nanomaterial uptake mechanisms through cell membranes are controversial and poorly understood in organelles like chloroplasts. (Pogodin, S., Slater, N. K. H. & Baulin, V. a. Surface patterning of carbon nanotubes can enhance their penetration through a phospholipid bilayer. *ACS Nano* 5, 1141-6 (2011), which is incorporated by reference in its entirety).

Figure 51:
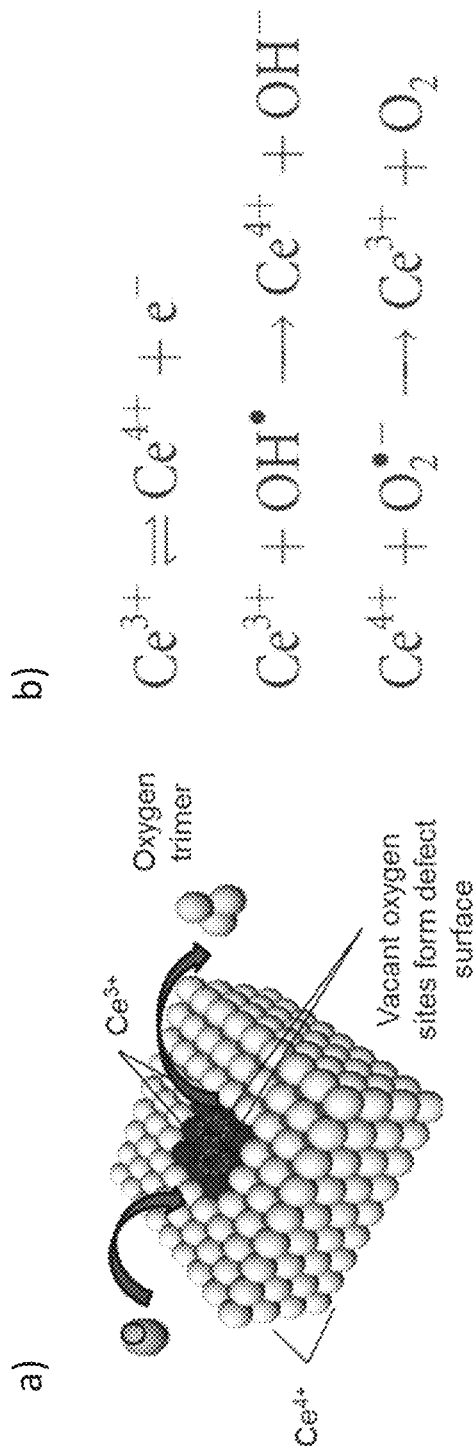
FIG. 51(a) is a schematic of nanoceria catalyzing the quenching a reactive oxygen species.
FIG. 51(b) includes reactions involved in nanoceria catalysis of a reactive oxygen species. Chen, J., et al., Rare earth nanoparticles prevent retinal degradation induced by intracellular peroxides. Nat Nanotechnol 1, 142-150 (2006).
Figure 52:
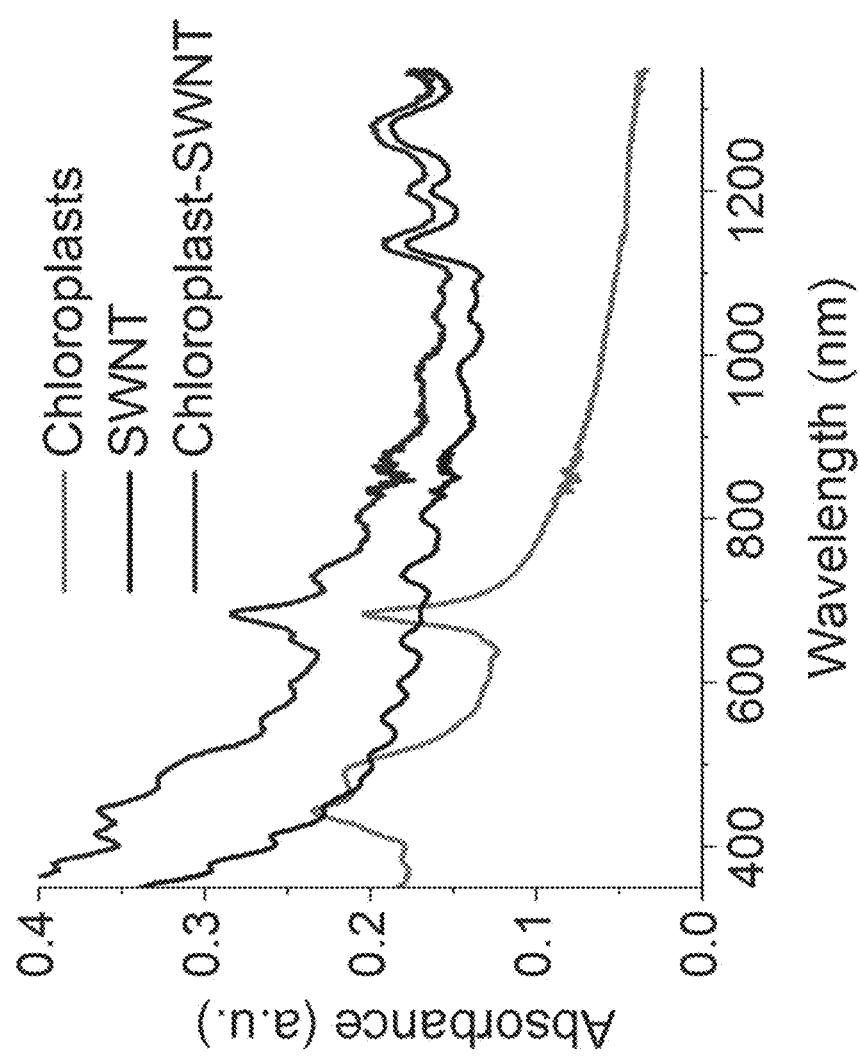
FIG. 52 is a graph representing the absorbance of chloroplasts, SWNTs and chloroplast-SWNTs as a function of the light wavelength.

Cerium oxide ($CeO_2$) nanoparticles (nanoceria) can catalyze the quenching of ROS in retinal cells, significantly reducing their intracellular concentrations (see, e.g., FIGS. 51(*a*) and 51(*b*)). (Chen, J., Patil, S., Seal, S. & McGinnis, J. F. Rare earth nanoparticles prevent retinal degeneration induced by intracellular peroxides. *Nat. Nanotechnol.* 1, 142-50 (2006), which is incorporated by reference in its entirety). Chloroplasts can have natural biochemical pathways to scavenge ROS and mechanisms for photosystem protein self-repair. (Edelman, M. & Matton, A. K. (2008)). However, the majority of enzymes involved cannot be synthesized ex vivo because they can lack the polypeptide precursors imported from the plant cell cytosol. (Soll, J. & Schleiff, E. Protein import into chloroplasts. *Nat. Rev. Mol. Cell Biol.* 5, 198-208 (2004), which is incorporated by reference in its entirety). Technologies that localize nanoceria at the sites of reactive oxygen species ("ROS") generation can exploit the oxygen vacancies in the $CeO_2$ lattice structure to effectively trap free radicals before they can damage nearby pigments, reaction centers and photosynthetic proteins. Cerium leakage from dextran nanoceria particles may not be able to penetrate the chloroplast outer envelope, and may promote only minor scavenging of photogenerated ROS. (Boghossian, A. A. et al. (2013)). More effective catalytic ROS scavenging and extended chloroplast photosynthetic activity may be achieved by assembling nanoceria within the photosynthetic machinery.

The interface between plant organelles and non-biological nanoparticles has the potential to impart the former with new and enhanced functions. For example, this nanobionic approach can yield chloroplasts that possess enhanced photosynthetic activity both ex vivo and in vivo, are more stable to reactive oxygen species ex vivo, and allow real time information exchange via embedded nanosensors for free radicals in plants. Accordingly, there is a need for nanoparticles that can interface with organelles, specifically, plant organelles ex vivo and in vivo to enable novel or enhanced functions. Similarly, there is a need for nanoparticles that can interface with intact photosynthetic organisms or intact cells of photosynthetic organisms ex vivo and in vivo to enable novel or enhanced functions. For example, the assembly of nanoparticle complexes within chloroplast photosynthetic machinery has the potential to enhance solar energy conversion through augmented light reactions of photosynthesis and ROS scavenging while imparting novel sensing capabilities to living plants.

Materials and Methods

Plant Material.

Chloroplasts were isolated from commercially available baby spinach leaves (*Spinacia oleraceae* L.) as described in Weise, S. E., et al. (2004) with modifications. Chloroplasts were isolated in sucrose buffer (pH 7.3, 28 mM $Na_2HPO_4$, 22 mM $KH_2PO_4$, 2.5 mM $MgCl_2$, 400 mM sucrose, and 10 mM KCl) by two cycles of centrifugation at 4000 RCF for 10 min, and then separated in a Percoll gradient consisting of 1 mL layers of 80%, 60%, 40%, and 20% Percoll in buffer. After 20 min of centrifugation at 4000 RCF, chloroplasts were selected from the 40% to 60% bands and washed with buffer. A 90% chloroplast intactness was determined by ferricyanide photoreduction with and without osmotic shock. (Lilley, R. M., Fitzgerald, M. P., Rienits, K. G. & Walker, D. A. Criteria of intactness and the photosynthetic activity of spinach chloroplast preparations. 75, 1-10 (1975), which is incorporated by reference in its entirety). Chlorophyll concentration was determined. (Amon, D. Copper Enzymes in Isolated Chloroplasts. Polyphenoloxidase in *Beta vulgaris*. *Plant Physiol*. 24, 1-16 (1949), which is incorporated by reference in its entirety). 100 µL of the chloroplast solution was added to 1 mL 80:20 acetone:water to suspend chloroplasts chlorophyll molecules, vortexed for 1 min, and centrifuged at 3000 g (Spectrafuge 24D by Labnet International) for 2 min. Absorption of supernatant was recorded at 652 nm (Shimadzu UV-3101PC) and chlorophyll content calculated based on extinction coefficient of 36 mL $mg^{-1}$. Wildtype Var. Col *Arabidopsis thaliana* plants between 4 to 6 weeks old were sampled for leaf nanoparticle uptake and electron transport rates. Plants were grown in propagation liner trays (Nursery supplies) with a soil mixture of Fafard Mix #3B maintained at water field capacity. Ambient temperature was 25° C. day/19° C. night during a 13 hr photoperiod. Leaf chlorophyll absorbance was measured with a SPAD meter (Minolta, SPAD 502).

SWNT and Nanoceria Synthesis.

Figure 40:
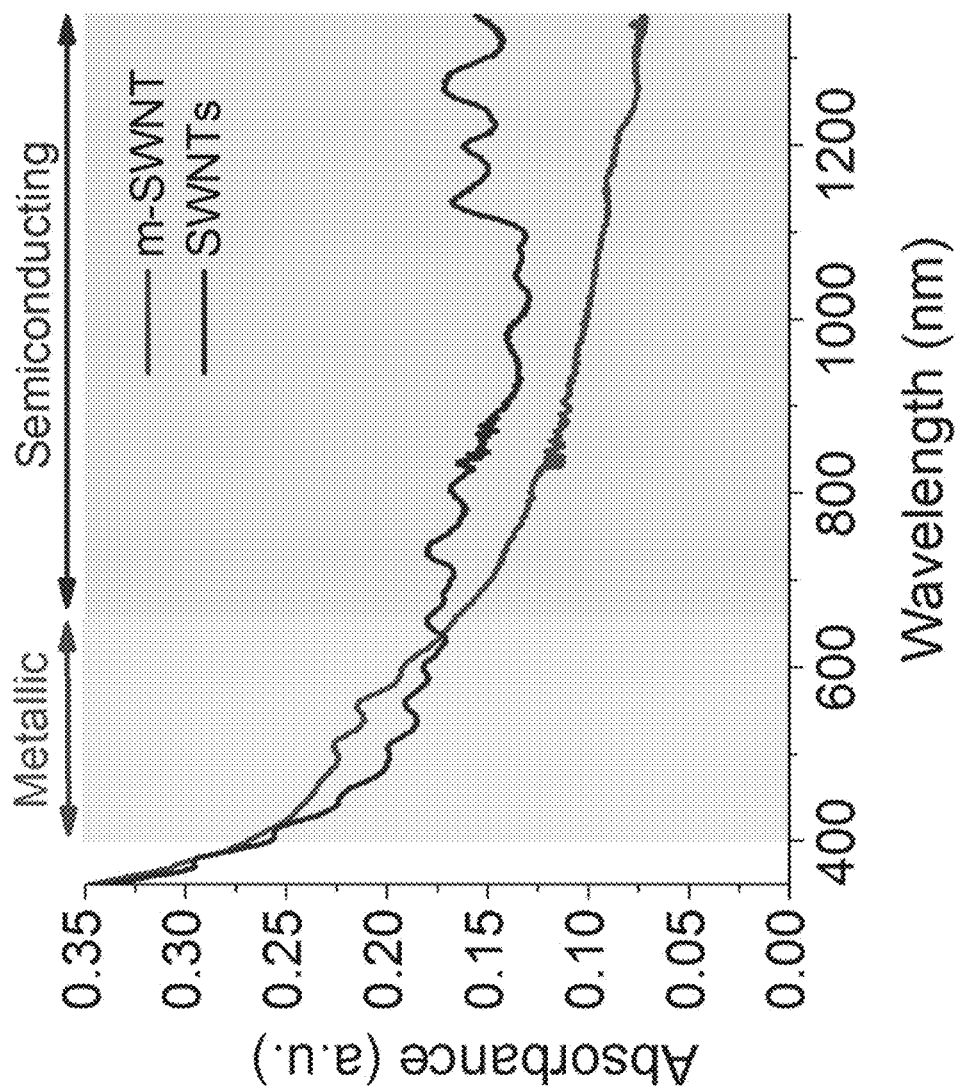
FIG. 40 is a graph representing SWNT and metallic SWNT (m-SWNTs) absorbance spectra (5 mg/L).

Raw HiPCO SWNTs (Unidym) were washed using organic phase separation. (Tvrdy, K. et al. A Kinetic Model for the Deterministic Prediction of Gel-Based Carbon Nanotube Separation. *ACS Nano* 7, 1779-1789 (2013), which is incorporated by reference in its entirety). The SWNTs were wrapped with a 30-base (dAdT) sequence of ssDNA ($AT_{15}$) (Integrated DNA Technologies), in chitosan, in PVA, or in phospholipid-polyethylene glycol. (Zhang et al. (2010); Reuel, N. F. et al. Transduction of glycan-lectin binding using near-infrared fluorescent single-walled carbon nanotubes for glycan profiling. *J. Am. Chem. Soc*. 133, 17923-33 (2011); Welsher, K. et al. A route to brightly fluorescent carbon nanotubes for near-infrared imaging in mice. *Nat. Nanotechnol*. 4, 773-80 (2009), each of which are incorporated by reference in its entirety). Metallic SWNTs were separated from HiPCO SWNTs (Unidym) by adsorption onto a magnetite-polymer construct. In brief, a mixture of SWNTs (1 mg/mL) in 1 wt % SDS was bath sonicated for 10 min followed by tip sonication at 20 W for 2 hrs. Then 3.5 mLs of equilibrated magnetic sephacryl was added to 10 mLs aliquots of SDS-SWNT and the mixture was stirred vigorously for 18 hrs. The solution was centrifuged at 4000 rpm for 10 min to settle out the sephacryl and the supernatant collected. The SDS-SWNT solution was characterized via photoabsorption spectroscopy to ensure isolation of m-SWNT (FIG. 40). The m-SWNTs had two characteristic peaks at 532 and 561 nm. In contrast, a mix of HiPCO SWNTs (Unidym) had several absorbance peaks in both the visible and the nIR. The m-SWNT SDS coating was exchanged with 30-base (dAdT) sequence of ssDNA ($AT_{15}$) (Integrated DNA Technologies) by sonication and centrifugation. Synthesis of poly(acrylic acid)-coated nanoceria proceeded as described in Asati (2010) with modifications. (Asati, A., Santra, S., Kaittanis, C. & Perez, J. M. Surface-charge-dependent cell localization and cytotoxicity of cerium oxide nanoparticles. *ACS Nano* 4, 5321-31 (2010), which is incorporated by reference in its entirety). Cerium (III) nitrate (2.5 mL, 1.09 g, 1 M, Sigma Aldrich, 99%) and an aqueous solution of 1,800 M.W. poly (acrylic acid) (2.5 mL, 2.25 g, 0.5 M, Sigma Aldrich) were added dropwise to 12.5 mL of HEPBS buffer (1.3 g, 0.4 M, Sigma Aldrich). The resulting mixture was adjusted to pH 8.5 with NaOH (8 M) and placed under continuous stirring for 24 hr at room temperature. The preparation was then centrifuged at 4000 RCF for 60 min to settle any debris and large agglomerates. The supernatant solution was then concentrated and purified by centrifugation at 4000 RCF for 10 min using a 10K Amicon cell (Millipore Inc.).

Nanoparticle Characterization.

SWNT concentration was calculated from absorbance measurements at 632 nm in a UV-vis-NIR scanning spectrometer (Shimadzu UV-3101PC) using an extinction coefficient of 0.036 $(mg/L)^{-1}$ $cm^{-1}$. The PAA-nanoceria concentration was determined by recording the absorbance at 240 nm and a molar absorption coefficient of 20 $cm^{-1}$ $mM^{-1}$. (Safi, M., Sarrouj, H., Sandre, O., Mignet, N. & Berret, J.-F. Interactions between sub-10-nm iron and cerium oxide nanoparticles and 3T3 fibroblasts: the role of the coating and aggregation state. *Nanotechnology* 21, 145103 (2010), which is incorporated by reference in its entirety). Carbon nitrile groups in the amide bonds of SWNT-NC complexes were detected by Fourier transform infrared spectroscopy (FTIR) Nicolet 4700 (Thermo). Atomic Force Microscopy (AFM) images of SWNT-nanoceria were taken in an Asylum Research AFM with a silicon tip in air. Samples were mounted on clean silicon dioxide plates coated with (3-aminopropyl) triethoxysilane APTES 1% (v/v). X-ray photoelectron spectroscopy (XPS) was performed on a Kratos AXIS Ultra X-ray Photoelectron Spectrometer with x-ray irradiation at 150 W. The TEM samples were mounted on Lacey-CA 300 mesh Cu grids (Ted Pella) and imaged in a 2000FX TEM microscope (JOEL) operating at 200 kV. The SWNT zeta potentials were quantified in a ZetaPALS Zeta potential analyzer (Brookhaven Instruments).

Nanomaterial Uptake by Isolated Chloroplasts.

SWNT chloroplast uptake videos were recorded in an AxioVision inverted microscope (Zeiss) coupled to a InGaAs OMA V array detector through a Acton SP2500 spectrometer (Princeton Instruments). Chloroplast autofluorescence was masked using 785 nm *Invictus* photodiode laser excitation (Kaiser) and 1100 nm long pass emission filter (Chroma). SWNTs (5 mg $L^{-1}$) were added to chloroplasts (0.05 mg Chl $mL^{-1}$) mounted on a glass slide and fluorescence recorded at 0.5 s (ss$(AT)_{15}$, lipid) or 1 s (Chitosan and PVA) per frame. Chloroplasts nIR imaging was performed under 658 nm Cl-200 laser excitation (CrystaLaser) and 860 nm long pass emission filter (Chroma). Raman spectroscopy 3D maps were acquired in a confocal Raman spectrometer HR-800 (Horiba BY) using a 632 nm laser source. Chloroplasts (0.05 mg Chl $mL^{-1}$) were mixed for 15 minutes with SWNTs (5 mg $L^{-1}$) at 1:1 v/v. Samples were mounted on silicon dioxide plates, focused on a 100× objective and Silicon Raman peak used as reference position in Z axis. The confocal hole was reduced to 50 µm for a Z-axis resolution of +1 µm. Raman spectra were taken after chloroplast exposure to 30 s under laser beam illumination when background levels were negligible. Raman 3D maps were plotted in Matlab R2011b. The PAA-nanoceria confocal images were taken in a Zeiss LSM 710 NLO microscope. Nanoceria were labeled via carbodiimide reaction with Alexa fluor 405 Cadaverine (Invitrogen). The preparation was filtered in 3 cycles of 5 min centrifugation through a 10K Amicon membrane (Milipore) at 14 g. Labeled PAA-nanoceria were mixed with chloroplasts (0.03 mg Chl mL$^{-1}$) and incubated for 2 hours. A FEI Technai Spirit TEM microscope at 80 KV was used to image chloroplast uptake of SWNT-NC complex. Chloroplasts (0.03 mg Chl mL$^{-1}$) were incubated for 2 hours with SWNT-NC (5 mg SWNT L$^{-1}$), and fixed (2.5% gluteraldehyde, 3% paraformaldehyde with 5% sucrose in 0.1M sodium cacodylate buffer pH 7.4). Then chloroplasts were post fixed in 1% osmium in veronal-acetate buffer, dehydrated and embedded in Spurrs resin, and sectioned at 50 nm thickness with a Leica Ultracut UCT microtome. Cerium analysis by inductively coupled mass spectroscopy (ICP-MS) was performed on chloroplasts after purification from free SWNT-NC by three cycles of 5 min centrifugation at 12000 g using 5 µm pore size Ultrafree-MC centrifugal filters (Millipore). Samples were characterized by ICP-MS at Elemental Analysis Inc. (Lexington, Ky.) under project number 6197-12.

Leaf Infiltration with SWNTs for Near Infrared Microscopy and Spectroscopy.

Leaves of *Arabidopsis thaliana* were infiltrated with 100 µL of ss(AT)$_{15}$-SWNTs. (Huang, X. et al. Magnetic virus-like nanoparticles in *N. benthamiana* plants: a new paradigm for environmental and agronomic biotechnological research. *ACS Nano* 5, 4037-45 (2011), which is incorporated by reference in its entirety). The SWNT stock suspension was dissolved in 10 mM MgCl$_2$ and 10 mM MES. A 1 ml needleless syringe was used to push the SWNT solution through several areas on the abaxial side of the leaf lamina. For in vivo near infrared imaging, plants were uprooted from soil and roots wrapped with a water-moistened cheese cloth to maintain plants hydrated during imaging. Leaves were immobilized on a no. 1 thickness coverslip using double-sided sticky tape.

Whole leaf imaging was performed on a CRi's Maestro (PerkinElmer) containing a liquid crystal tuning element that allows transmitted light to be electronically tuned with a maximum wavelength range of 650-1050 nm and a 40 nm bandpass under a laser excitation source of 785 nm. By analyzing the spectral emission wavelengths of the SWNT signal and leaf fluorescence, the entire signal's fingerprint was separated into these components and the signal of interest was determined. The emission window for leaves infiltrated with ss(AT)$_{15}$-SWNTs (30 mg L$^{-1}$) was set from 950 to 1050 nm with a 5 nm step size and 20 second reading at each step.

Leaf cross sections were imaged in the nIR by an Axiovision Zeiss inverted microscope with an InGAs array nIR detector. Leaf brightfield images were taken with a Zeiss brightfield camera (Zeiss, Axiovert 200). The SWNT nIR fluorescence images were collected at 0.5 s exposure with an emission filter of 1100 nm and laser excitation of 785 nm off resonance of photosynthetic pigments. Leaves were infiltrated with 100 ul of SWeNT®SG76 (SouthWest Nanotechnologies Inc.) ss(AT)$_{15}$-SWNTs (30 mg L$^{-1}$). Hand cross sections were imaged to detect SWNTs in the proximity of leaf veins. Imaging of leaf parenchyma cells and chloroplast was performed in cross sections fixed in 2.5% gluteraldehyde, 3% paraformaldehyde with 5% sucrose in 0.1M sodium cacodylate buffer (pH 7.4), and fixed in 1% OsO4 in veronal-acetate buffer. The cell pellet was stained in block overnight with 0.5% uranyl acetate in veronal-acetate buffer (pH6.0), then dehydrated and embedded in Embed-812 resin. Sections were cut on a Reichert Ultracut E microtome with a Diatome diamond knife at a thickness setting of 50 nm. Chloroplast fluorescence was imaged with a 658 nm 200 mW diode pumped solid state laser (CrystaLaser, RCL-100-660) and a band pass filter 700-750 nm (Chroma). Leaf images were colocalized to SWNT sources of nIR fluorescence using a custom MATLAB mapping file using leaf autofluoresence as a broadband emission source. A similar mapping file was created to map regions of interest from the SWNT sources of fluorescence and the brightfield images. SWNT images and either leaf fluorescence or leaf brightfield images were overlaid using coordinates from our mapping files.

Figure 23:
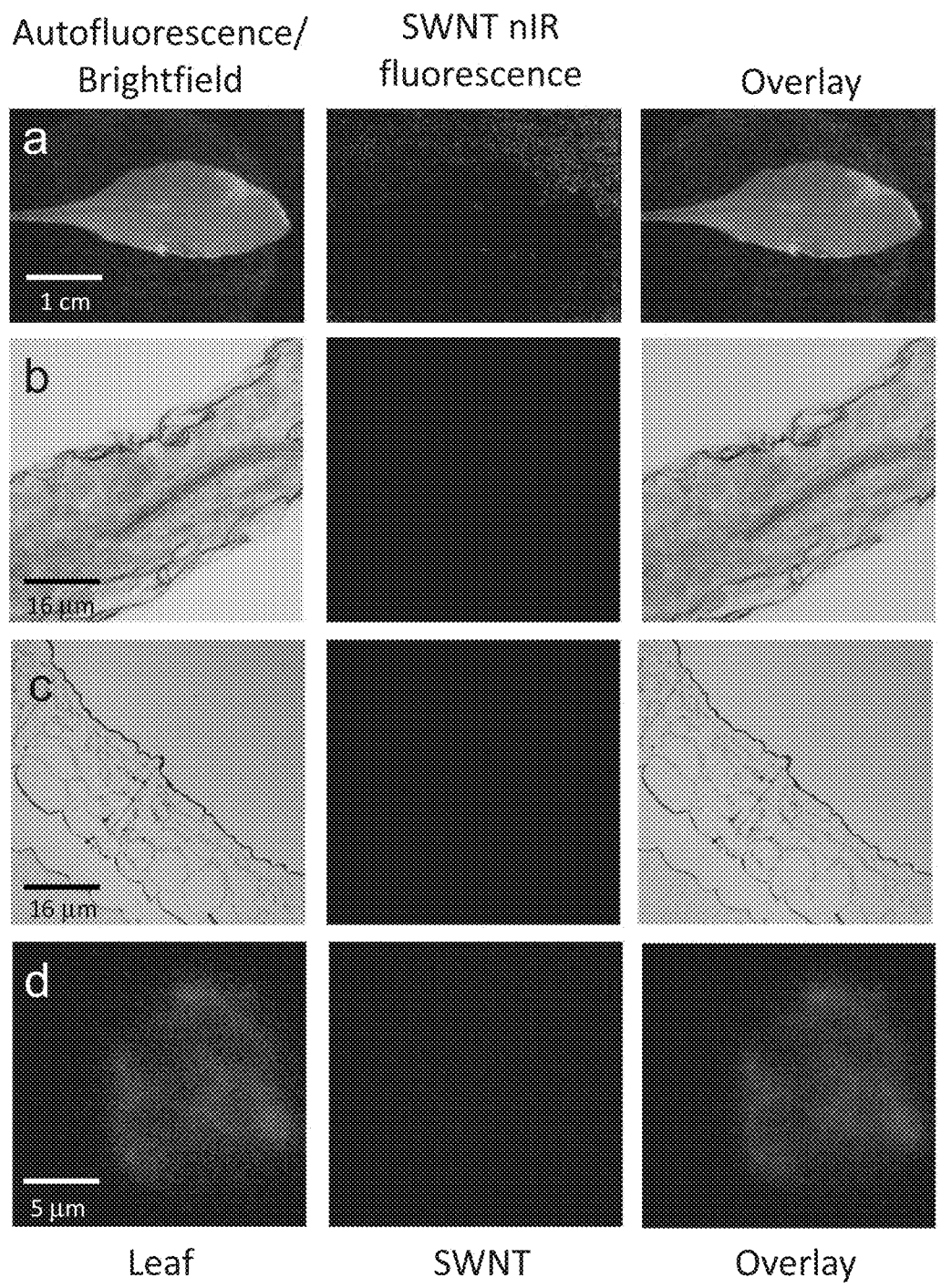
FIG. 23 shows images of *A. thaliana* leaves with infiltration medium.

Near-infrared optical imaging and spectra of whole leaves (*A. thaliana*) infiltrated with SWNTs were collected on two inverted microscopes (Zeiss, Axiovert 200) equipped with a 20× objective (Zeiss, α-Plan-APOCHROMAT 20×DIC (UV) VIS-IR). For nIR imaging, the microscope was attached to a 2D InGaAs CCD array (OMA-V 2D, Princeton Instruments) and CCD camera (Zeiss, Axio-Cam Mrm). For spectrometry, the microscope was coupled to an InGaAs array detector (OMA-V, Princeton Instruments) through an Acton SP-2500 spectrograph (Princeton Instruments). Infiltrated SWNT were excited with a 785 nm Invictus photodiode laser excitation (Kaiser) through the leaf tissue. Images were acquired at a frame rate of 2 Hz, and spectra were recorded with a 10 s exposure time. The nIR fluorescence of SWNTs was not detected in control leaves infiltrated with buffer (FIG. 23). Control leaves had a background signal up to 1025 nm and 2000 cm-1 in nIR fluorescence and Raman spectra, respectively. Raman spectra were collected in HR-800 spectrometer (Horiba BY) using a 785 nm laser source with a 10× objective under a 785 nm laser excitation, at 2 cycles of 5 s each.

Optical Sensing of Nitric Oxide in Chloroplast Ex Vivo and Leaves In Vivo.

Figure 42:
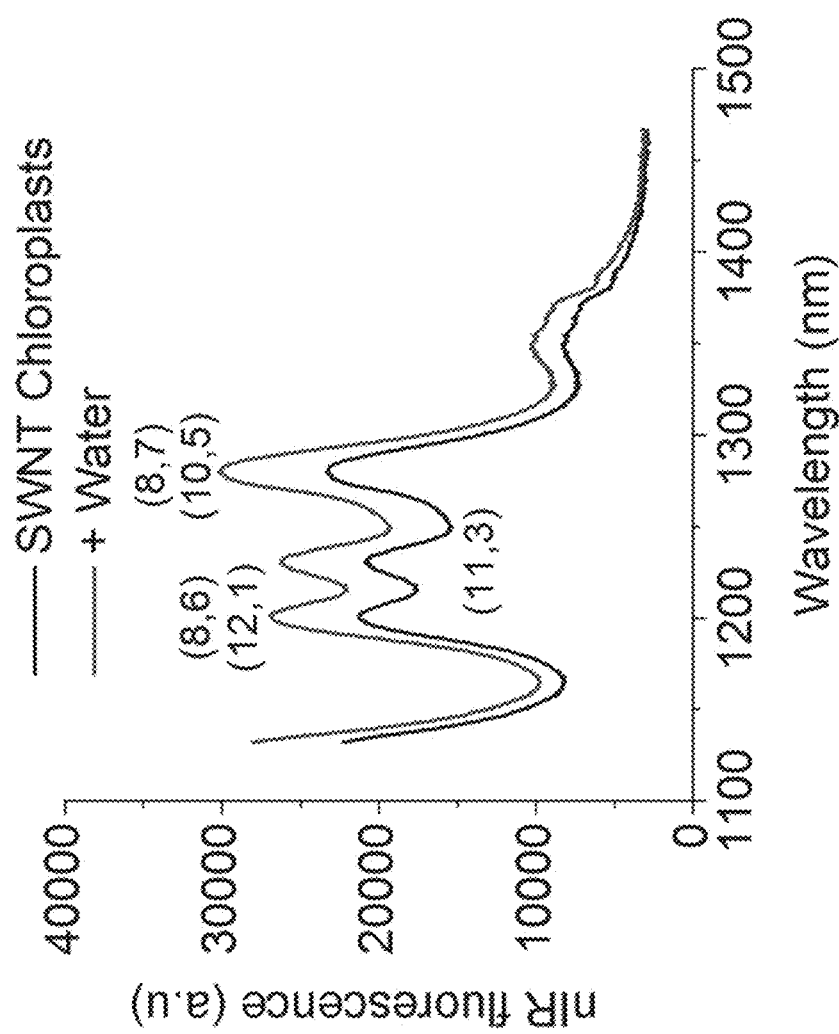
FIG. 42 is a graph representing the fluorescence intensity of SWNT chiralities inside extracted chloroplasts in the presence of deionized water.
Figure 43:
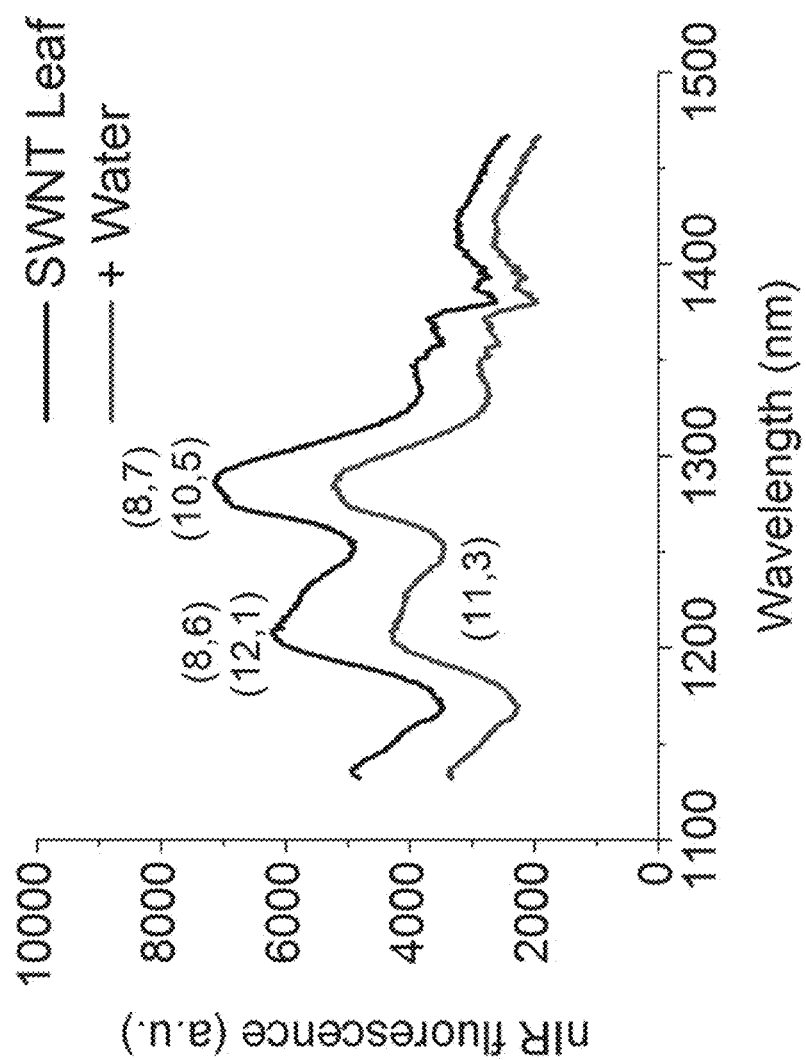
FIG. 43 is a graph representing the fluorescence intensity of SWNT chiralities inside leaves in the presence of deionized water.
Figure 44:
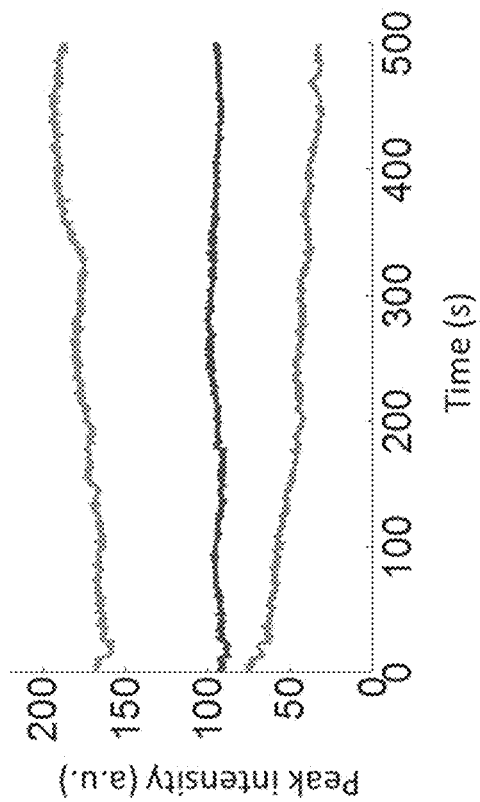
FIG. 44 includes an image of SWNTs inside leaves in the absence or presence of deionized water, and a graph representing the peak intensity of the imaged SWNTs at a laser excitation of 785 nm.
Figure 44:
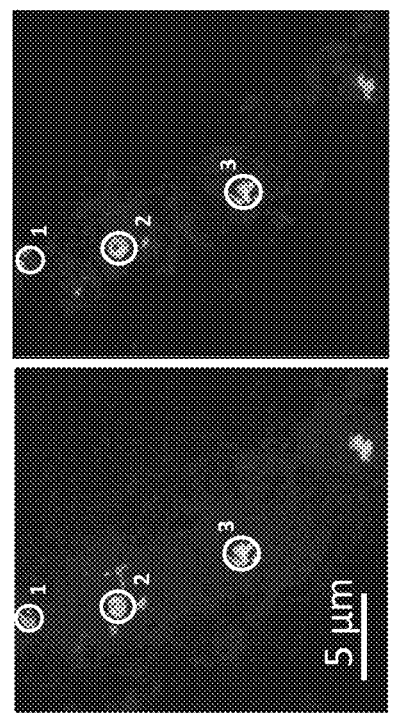

For nitric oxide (NO) quenching experiments, isolated chloroplasts (0.01 mg Chl mL$^{-1}$) were suspended in 200 uL solution of ss(AT)$_{15}$-SWNTs (5 mg L$^{-1}$) in water for 15 min. The nIR fluorescence spectra was collected as explained above in a range of 1150 to 1450 nm with a 10 s exposure time under a 785 nm laser excitation. Then 10 uL of NO solution was added and the measurements were repeated. For leaves, a region of interest within the leaf lamina was found with several SWNT fluorescence sources. Small incisions were made adjacent to the SWNT regions of interest to allow NO internalization. A 20 µL volume of a dissolved NO solution was added to the leaf incision and the SWNT intensity at the predetermined regions of interest was imaged for 500 seconds and spectra collected at 10 s exposure time as explained above. For control experiments where H$_2$O was added in lieu of NO, the process was repeated by adding H$_2$O instead of NO to the extracted chloroplasts and the leaf lamina (FIGS. 42-44). Image processing was accomplished by monitoring the peak-intensity profile of SWNT regions of interest as a function of time for the duration of the movie. SWNT peak intensity did not change substantially after addition of H$_2$O.

Laurdan Labeled Liposomes and SWNT Interaction.

Laurdan (15 µM) was suspended with the most common chloroplast lipids, DGDG (0.7 mM) and MDGD (0.3 mM)

(Avanti lipids) in chloroform-methanol (1:1). The solution was evaporated in vacuum chamber for 3 hr followed by nitrogen gas drying. The lipid layer was pre-hydrated in 3 mL of sterile PBS buffer 1× warmed above the lipids gel-fluid transition temperature (70° C.). The preparation was immediately submerged in a water bath above 80° C. while spinned in a rotary for 60 min. The laurdan-labeled liposome change in fluorescence in the presence of ss(AT)$_{15}$-SWNTs was measured in the 410-650 nm range on a Varioskan flash plate reader 3001 (Thermo) under wavelength excitation of 390 nm. (Szilagyi, A., Selstam, E. & Akerlund, H. Laurdan fluorescence spectroscopy in the thylakoid bilayer: The effect of violaxanthin to zeaxanthin conversion on the galactolipid dominated lipid environment. Biochim. Biophys. Acta 1778, 348-355 (2008), which is incorporated by reference in its entirety). Laurdan generalized polarization (Gp) was calculated. (Szilagyi, A., et al. (2008)).

Nanoceria Scavenging of Reactive Oxygen Species.

Figure 41:
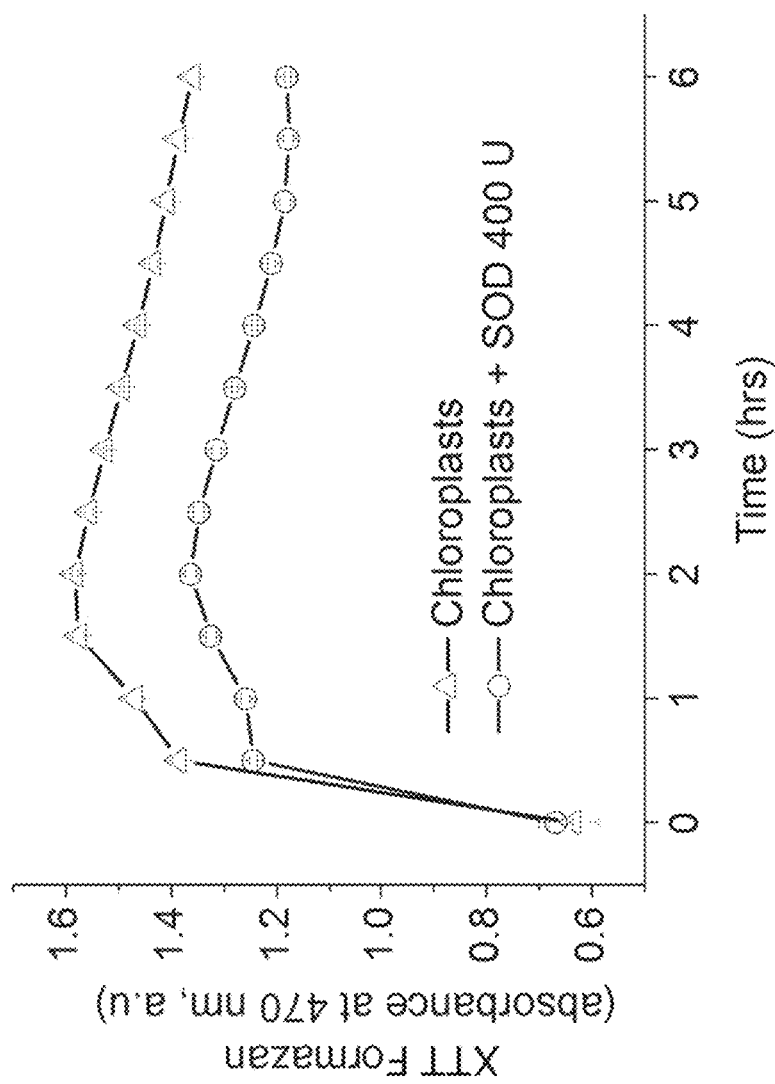
FIG. 41 is a graph representing XTT cumulative reduction in the present of chloroplasts incubated with scavenger superoxide dismutase (SOD).
Figure 45:
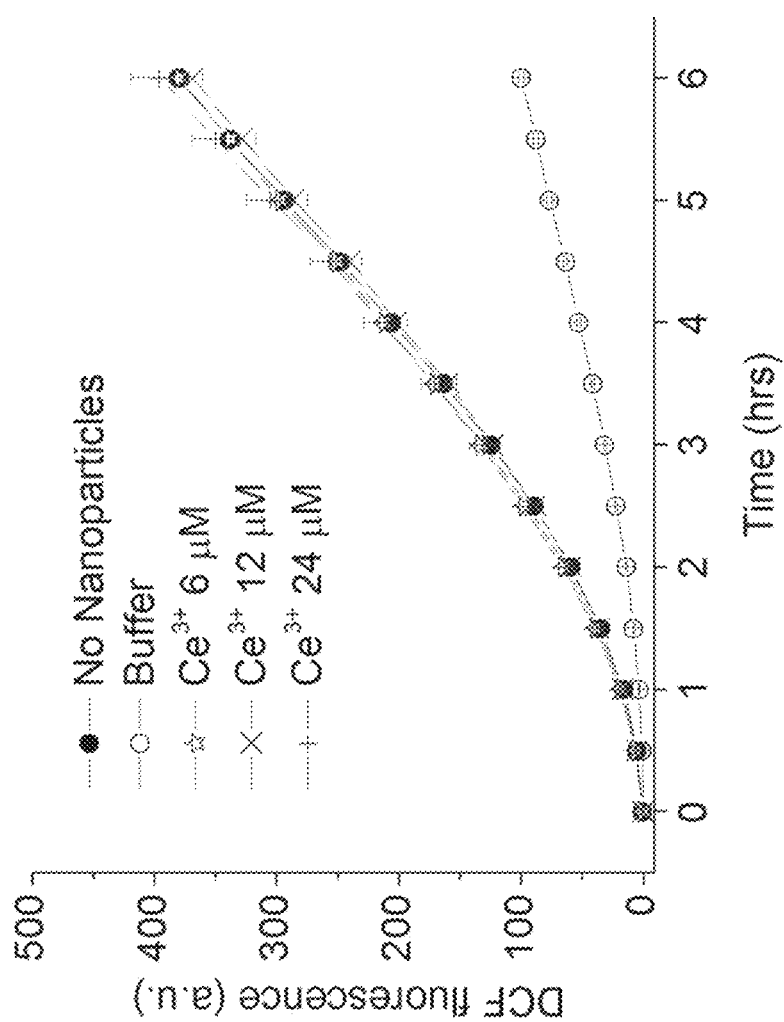
FIG. 45 is a graph representing chloroplast ROS scavenging in response to $Ce^{3+}$ as quantified by the conversion of $H_2DCFDA$ to DCF. Error bars are standard deviations (n=3).
Figure 46:
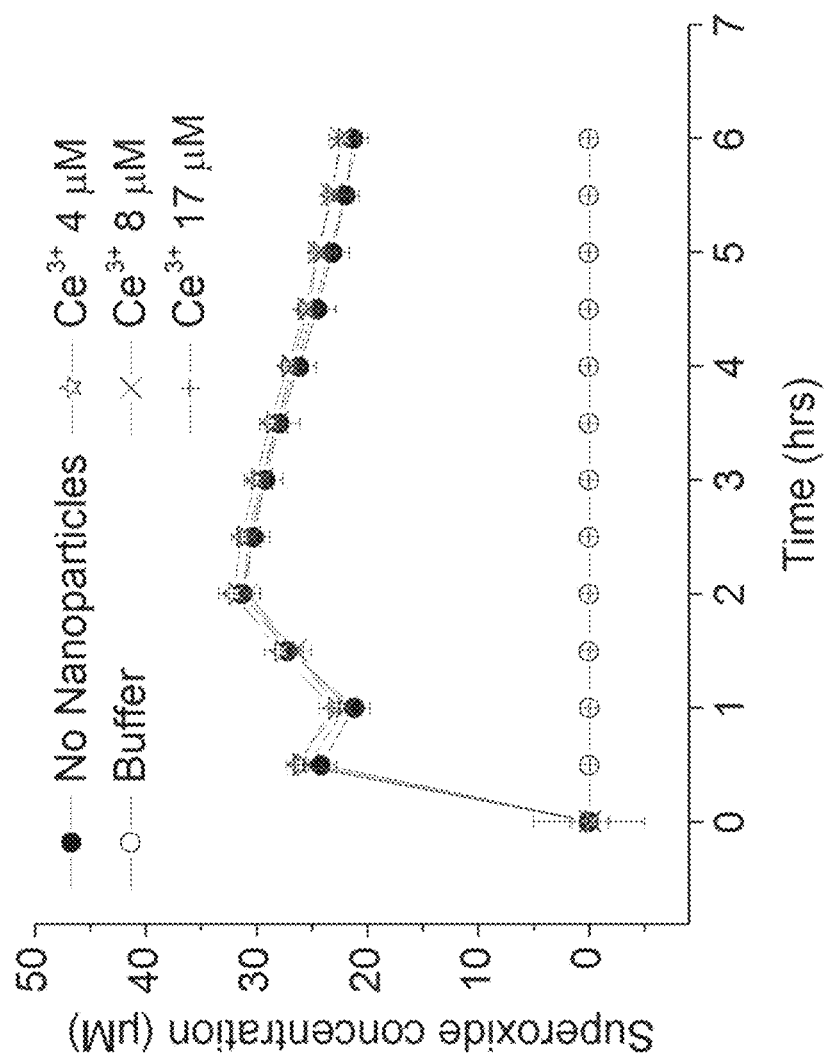
FIG. 46 is a graph representing the chloroplast superoxide concentration in response to $Ce^{3+}$. Error bars are standard deviations (n=3).

Chloroplast (approximately 0.01 mg Chl mL$^{-1}$) ROS scavenging by nanoparticles was quantified by the conversion of the membrane permeant 2',7'-dichlorodihydrofluorescein diacetate (H$_2$DCFDA, 0.6 mg mL$^{-1}$) to the fluorescent 2',7'-dichlorofluorescein (DCF). (Mubarakshina, M. M. et al. Production and diffusion of chloroplastic H2O2 and its implication to signalling. *J. Exp. Bot.* 61, 3577-87 (2010), which is incorporated by reference in its entirety). The effect of nanoparticles on superoxide concentration was determined by the reduction of 2,3-bis (2-methoxy-4-nitro-5-sulfophenyl)-2H-tetrazolium-5-carboxanilide sodium salt (XTT, 0.06 mg mL$^{-1}$) dye (Sigma Aldrich) in the presence of superoxide as in previous studies on plant cells. (Jiang, M. Water stress-induced abscisic acid accumulation triggers the increased generation of reactive oxygen species and up-regulates the activities of antioxidant enzymes in maize leaves. *J. Exp. Bot.* 53, 2401-2410 (2002); and Able, A., Guest, D. & Sutherland, M. Use of a new tetrazolium-based assay to study the production of superoxide radicals by tobacco cell cultures challenged with avirulent zoospores of *Phytophthora Parasitica* var *Nicotianae*. Plant Physiol. 117, 491-9 (1998), each of which is incorporated by reference in its entirety). To allow the transport of the membrane impermeable SOD to the sites of superoxide generation, chloroplasts were ruptured in water then suspended in buffer during incubation with SOD for an hour. The significantly lower levels of XTT formazan production in the presence of the superoxide scavenger SOD confirmed previous studies in plant cells (Able, et al. (1998)), demonstrating that XTT was responsive to changes in superoxide concentration. It was confirmed that the reduction of XTT responds to chloroplast superoxide concentration by incubating chloroplasts with superoxide dismutase (SOD), a well-known superoxide scavenger (FIG. 41). In DCF experiments, chloroplasts were illuminated at approximately 3% of photosynthesis saturation light levels to reduce H$_2$DCFDA light induced autofluorescence (FIG. 45), while in XTT experiments, illumination with a LED flood lamp FL-70W (LED wholesalers) was 30% of photosynthesis light saturation (200 μmols m$^{-2}$ s$^{-1}$ photosynthetic active radiation, PAR, or 40 W m$^{-2}$). DCF fluorescence at 520 nm and XTT absorbance at 470 nm was recorded every 30 min for six hours with a Varioskan well plate reader (Thermo). Superoxide concentration based on XTT measurements was calculated from background corrected absorbance values using an extinction coefficient of 21.6 mM$^{-1}$ cm$^{-1}$. (Jiang, M. (2002)). Controls with cerium nitrate addition at the same concentrations of PAA-NC show no association of ROS and superoxide scavenging with cerium concentration (FIGS. 45 and 46). More specifically, Ce$^{3+}$ had no effect on ROS scavenging quantified by the conversion of H$_2$DCFDA to DCF or chloroplast superoxide concentration.

Extracted Chloroplast and Leaf Photosynthesis.

Photosynthetic activity was monitored in isolated chloroplasts (approximately 0.01 mg Chl mL$^{-1}$) in sucrose buffer by measuring the change from initial absorbance at 600 nm of the electron acceptor dye dichloroindophenol (DCPIP, 0.034 mg mL$^{-1}$) with an extinction coefficient of 21.7 mM$^{-1}$ cm$^{-1}$. (Lonergan, T. A. & Sargent, M. L. Regulation of the Photosynthesis Rhythm in Euglena gracilis CS1-75. *Plant Physiol.* 64, 99-103 (1979), which is incorporated by reference in its entirety).

Figure 35:
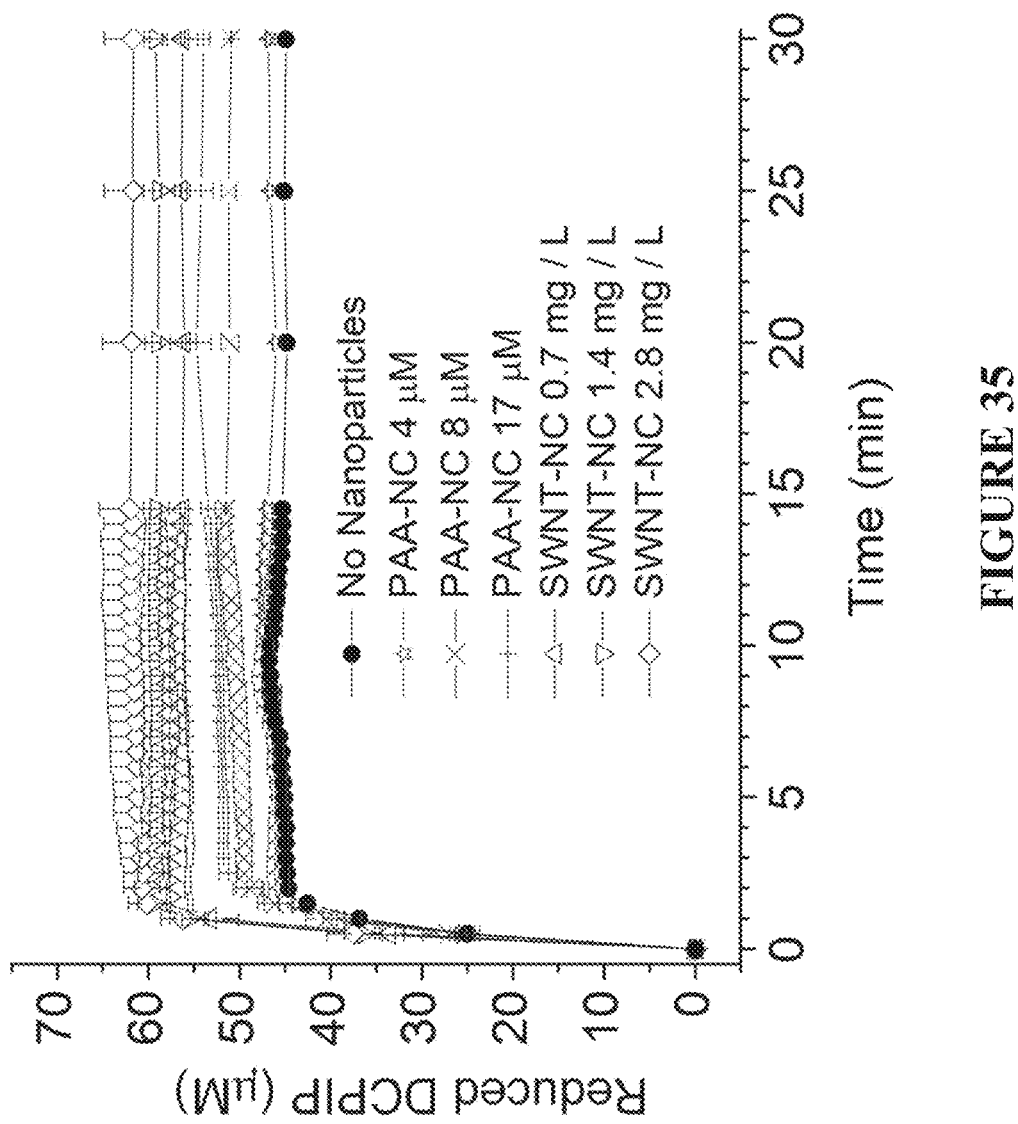
FIG. 35 is a graph representing the photosynthetic activity of chloroplasts with nanoceria and SWNT-nanoceria in the first 30 minutes of reduction of the electron acceptor dye DCPIP.
Figure 36:
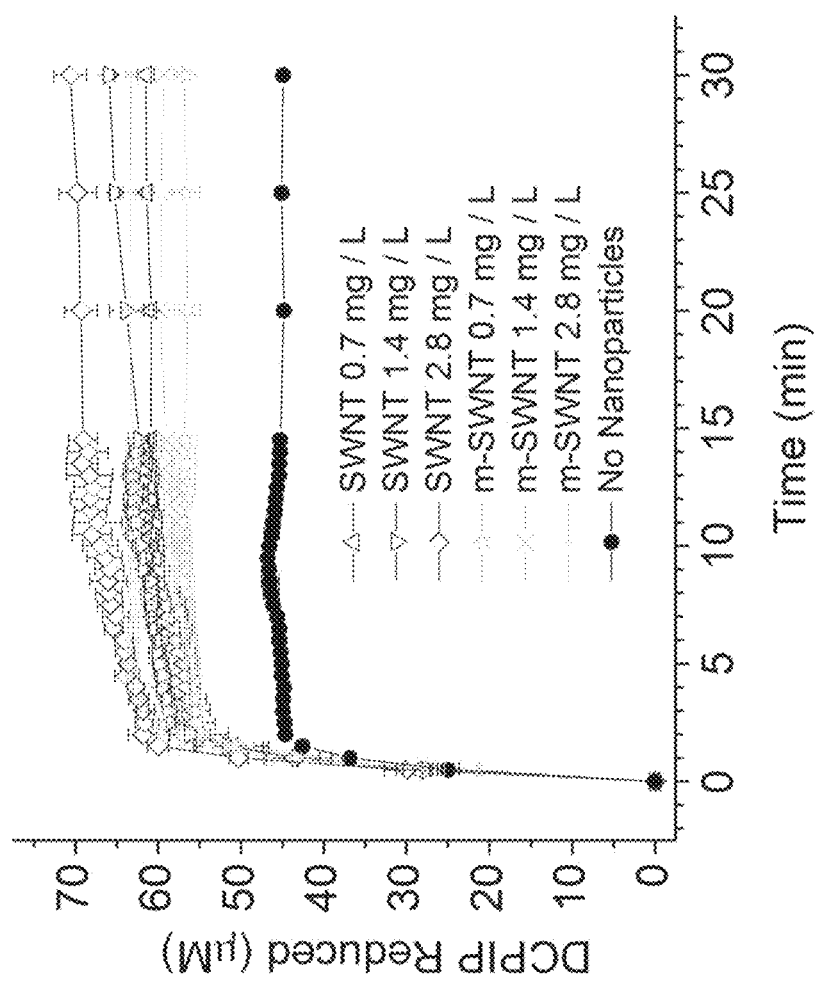
FIG. 36 is a graph representing the photosynthetic activity of chloroplasts with SWMTs and m-SWNTs in the first 5 minutes of reduction of the electron acceptor dye DCPIP.
Figure 37:
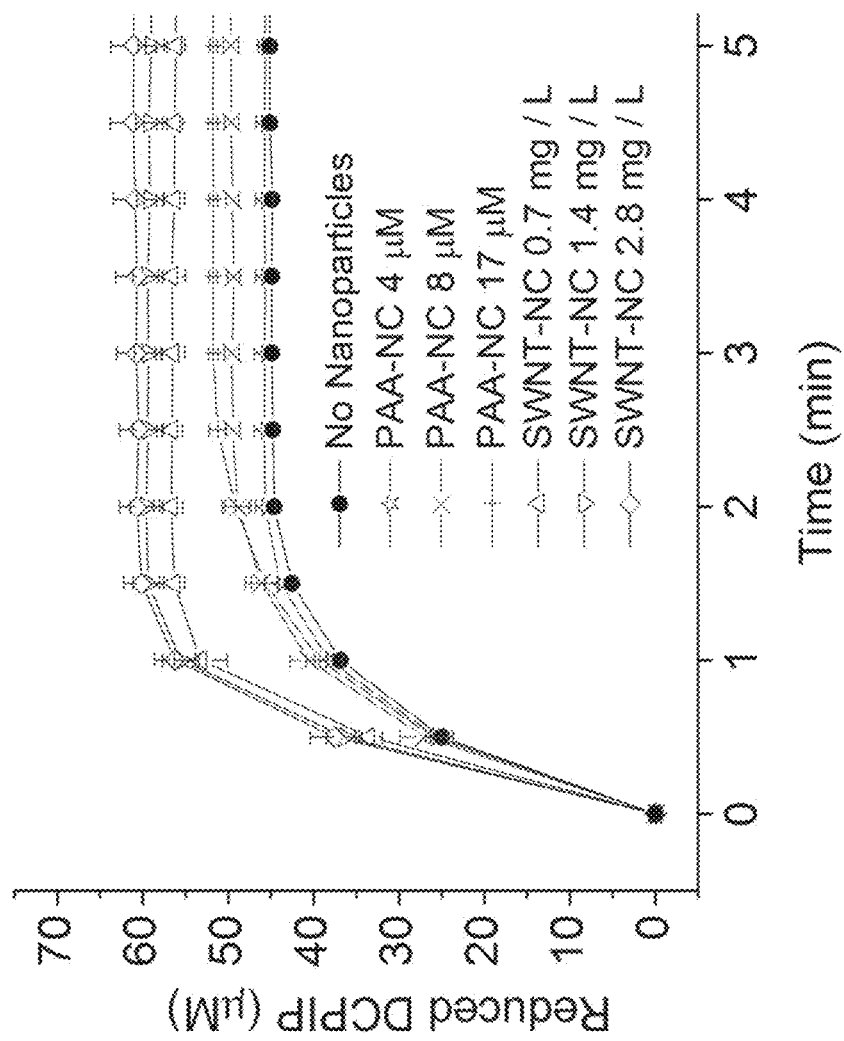
FIG. 37 is a graph representing the photosynthetic activity of chloroplasts with nanoceria and SWNT-nanoceria in the first 30 minutes of reduction of the electron acceptor dye DCPIP.
Figure 38:
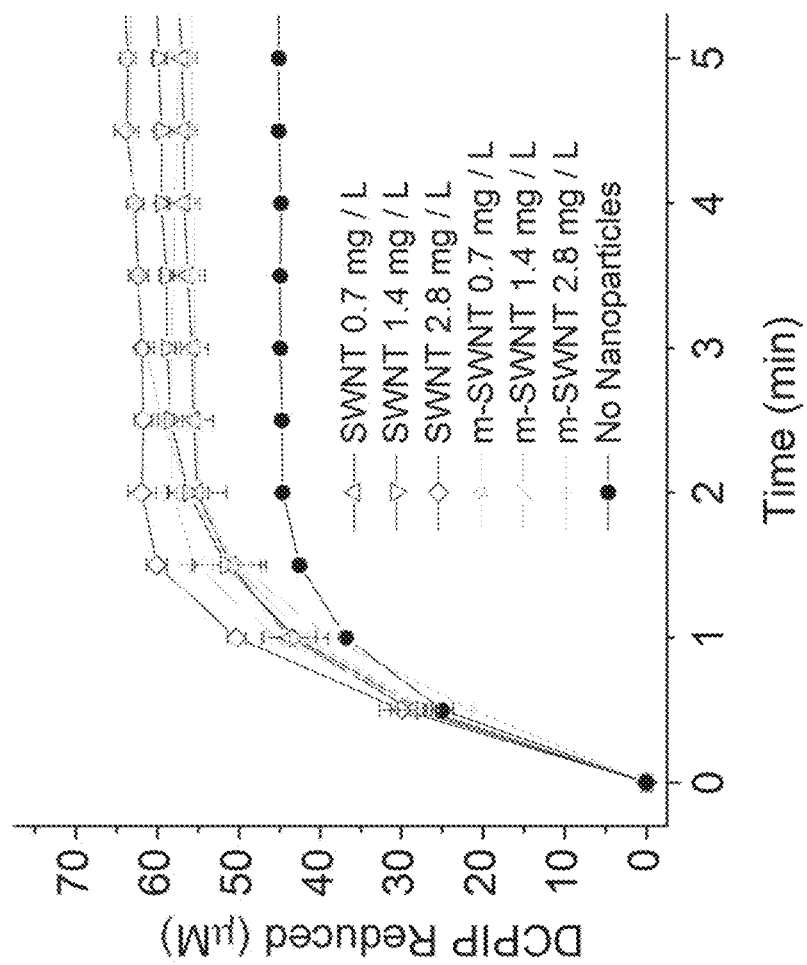
FIG. 38 is a graph representing the photosynthetic activity of chloroplasts with nanoceria and SWNT-nanoceria in the first 5 minutes of reduction of the electron acceptor dye DCPIP.

The effect of SWNT and SWNT-NC alone on DCPIP in buffer was not significant relative to nanoparticles interfaced with chloroplasts (FIGS. 35-39). Increased photosynthetic activity of chloroplasts with nanoceria and SWNT-nanoceria was seen in the first 30 minutes of reduction of the electron acceptor dye DCPIP (FIG. 35). Both SWNTs and m-SWNTs were observed to increase the photosynthetic activity of chloroplasts in the first 30 minutes but m-SWNTs were less effective than SWNTs (FIG. 36). FIGS. 37 and 38 show the data for the initial five minutes of the experiments shown in FIGS. 35 and 36. The table shown in FIG. 39 shows a comparison of DCPIP (μM) change between chloroplasts with nanoparticles minus chloroplasts without nanoparticles (Chloroplasts) vs. DCPIP reduced by nanoparticles in buffer after 30 minutes and 6 hrs. While reduction of DCPIP by PAA-NC in buffer contributed significantly to the observed DCPIP reduction by chloroplasts in the first 30 minutes, DCPIP reduction in buffer by SWNT-NC could not account for the effect of these nanoparticles in chloroplast photosynthetic activity both in the initial 30 min and after 6 hrs. Similarly, both SWNTs and metallic SWNTs (m-SWNT) showed a low dye reduction in buffer relative to their effect on chloroplast DCPIP change. Data represented averages (n=3). Error bars represented standard deviations.

Figure 47:
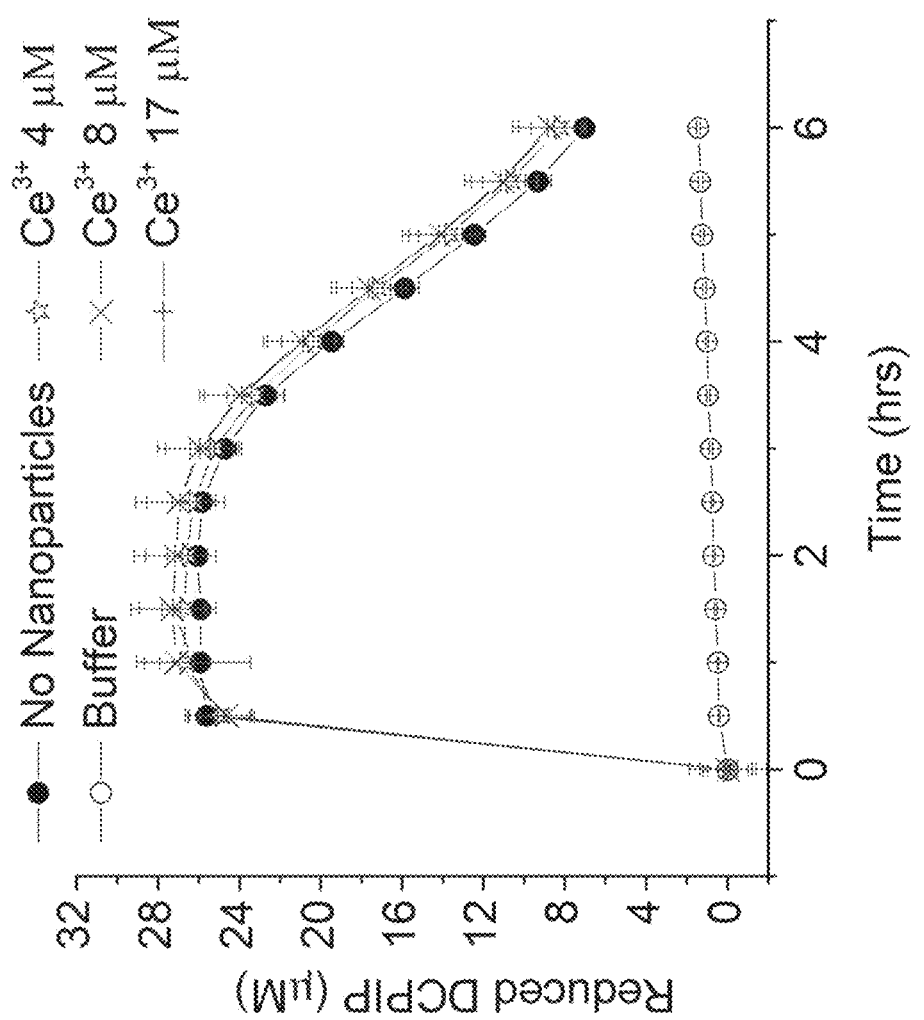
FIG. 47 is a graph representing the reduction of the electron acceptor DCPIP (0.01 mg chlorophyll/mL) in response to $Ce^{3+}$. Error bars are standard deviations (n=3).

Chloroplasts were illuminated with a light intensity of approximately 200 μmol m$^{-2}$ s$^{-1}$ PAR (40 W m$^{-2}$) with a LED flood lamp FL-70W (LED wholesalers). Cerium nitrate treatments were performed as a control at same concentrations of PAA-NC. Cerium did not influence chloroplast photosynthetic activity (FIG. 47). Leaf electron transport rates were assessed by measuring the yield of chlorophyll fluorescence with a MINI-PAM photosynthesis yield analyzer (WALZ). Light absorbed by chlorophyll pigments can be used for photochemistry, while excess energy is converted into heat or re-emitted as fluorescence. By measuring the yield of chlorophyll fluorescence, information about these competing processes can be quantified to calculate rate of electron transport, an indicator of the light reactions of photosynthesis. (Maxwell, K. & Johnson, G. N. Chlorophyll fluorescence—a practical guide. *J. Exp. Bot.* 51, 659-668 (2000), which is incorporated by reference in its entirety).

Examples

High Zeta Potential Nanoparticles Spontaneously Assemble within Chloroplasts

Figure 2:
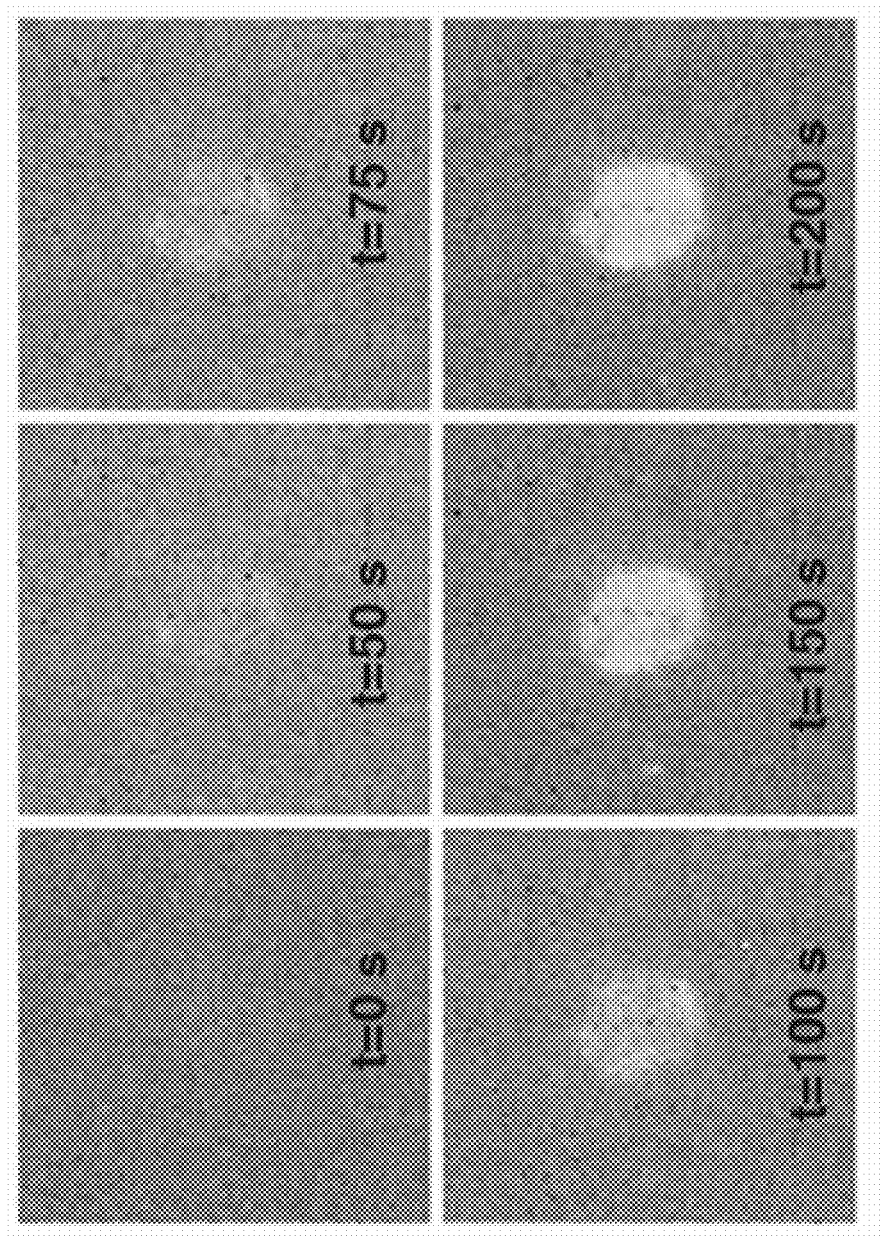
FIG. 2 is a nIR photograph showing the penetration of $AT_{15}$-SWNTs into isolated chloroplasts.

A single-particle tracking of nIR fluorescent semi-conducting SWNTs was utilized to investigate their interaction with isolated plant chloroplasts from spinach leaves. SWNTs did not photobleach and fluoresce in the near infrared region above 1100 nm, where chloroplast autofluorescence is minimal (FIG. 1). SWNT fluorescence of chiralities (9,4), (8,6), (12,1), (11,3), (8,7), and (10,5) was quantified inside chloroplasts with a laser excitation (785 nm) off-resonance to photosynthetic pigments. Surprisingly, SWNTs suspended in strongly cationic or anionic coatings (i.e., high magnitude of the zeta potential) were found to traverse and localize rapidly within the chloroplast outer envelope, and not just adsorb to the exterior. The process was observed to occur within seconds of nanoparticle interaction with the inner and outer lipid bilayer (FIG. 2). This process was irreversible, and in the case of ss(AT)$_{15}$ DNA and chitosan-wrapped SWNTs dosed at 2.5 mg L$^{-1}$ concentration, left no free nanotubes suspended in the buffer solution.

Figure 6:
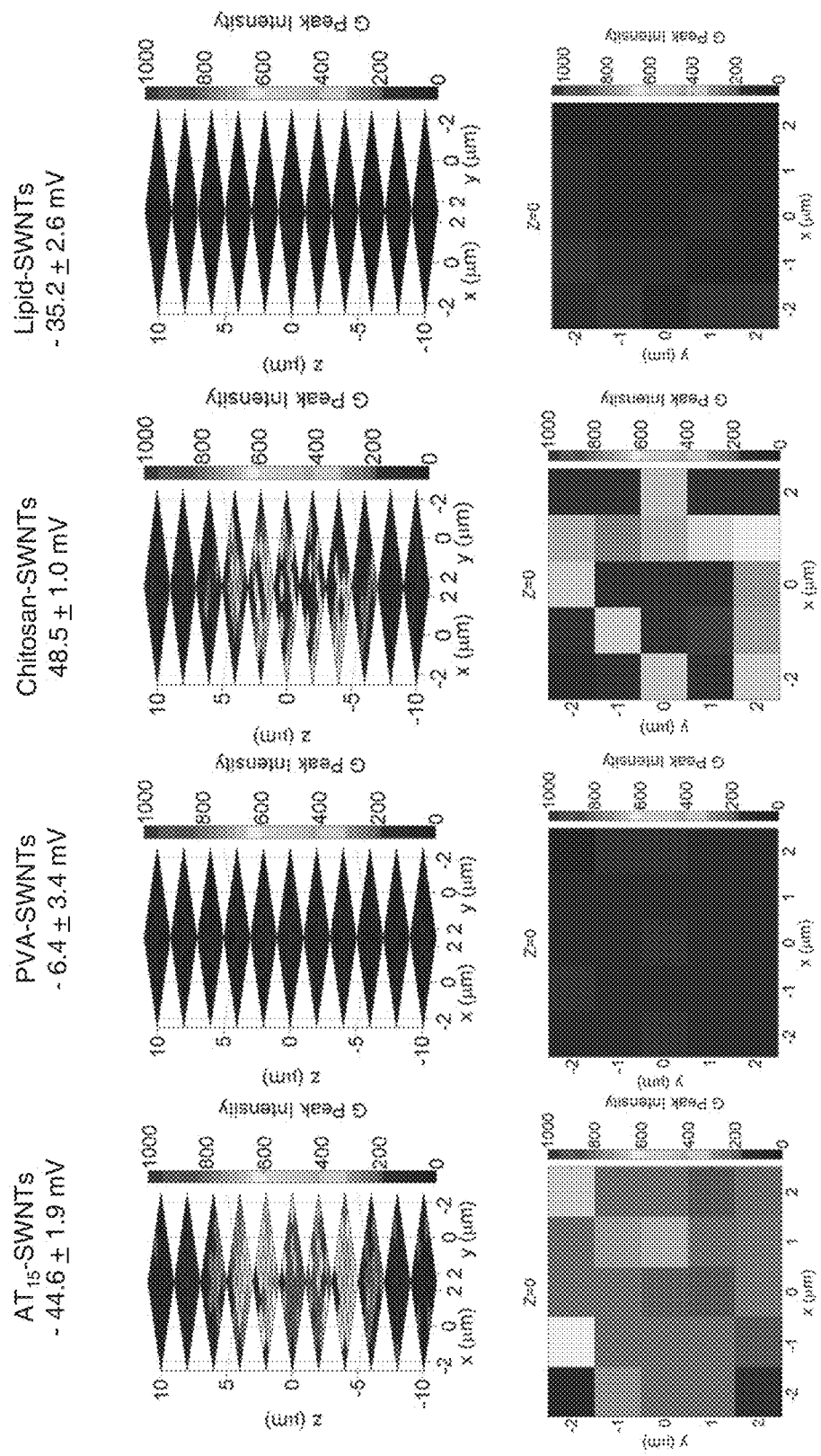
FIG. 6 includes confocal Raman spectroscopy 3D maps showing the location of nanoparticles relative to chloroplasts.

Not all SWNT types were transported through lipid bilayers. Both nIR SWNT fluorescent images (FIGS. 4(a)-(c) and FIGS. 5(a)-(d)) and confocal 3D mapping of the characteristic SWNT Raman G-band (1580 nm) (FIG. 6) indicated that while ss(AT)$_{15}$ and chitosan SWNTs were embedded within chloroplasts, polyvinyl alcohol (PVA) and lipid-wrapped SWNTs did not interact with the lipid bilayer. This appears to confirm some modeling studies that suggested SWNT surface patterning and charge as key traits determining penetration through lipid membranes. (Pogodin, S., et al. (2011); Chem, J., et al. (2006)). A highly negative or positive SWNT zeta potential favored nanotube adsorption to the chloroplast lipid membrane (FIG. 6). The ss(AT)$_{15}$ and chitosan SWNTs having zeta potentials of $-44.6\pm1.9$ mV and $48.5\pm1.0$ mV, respectively, were transported inside chloroplasts, but not PVA-wrapped SWNTs with more neutral values, $-6.4\pm3.4$ mV. However, lipid-SWNTs with a negative zeta potential, $-35.2\pm2.6$ mV, were unable to move through the chloroplast outer envelope, confirming a membrane trapping inhibition once SWNTs were coated with lipids.

Figure 7:
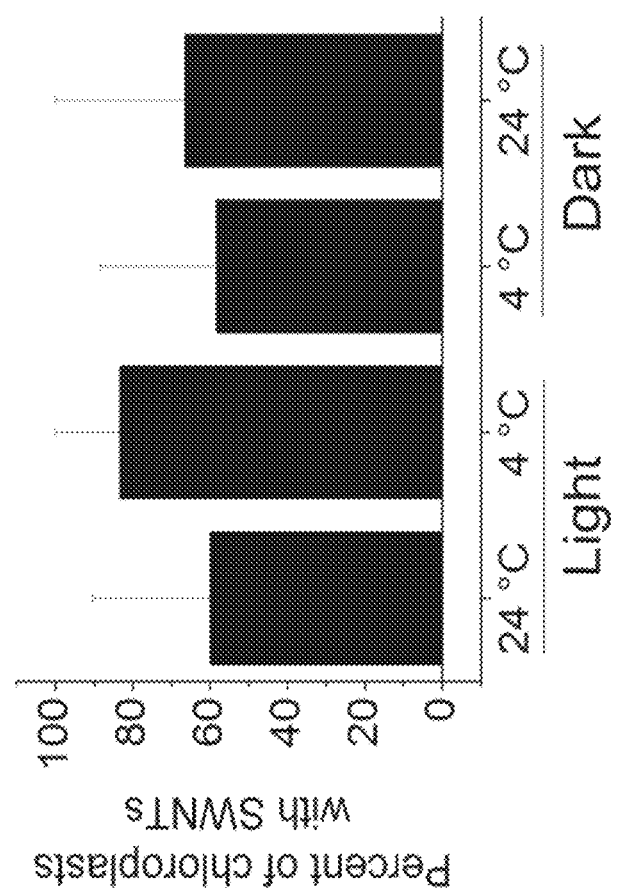
FIG. 7 is a graph representing the percent of chloroplasts containing nanoparticles as a function of the temperature and light conditions.
Figure 8:
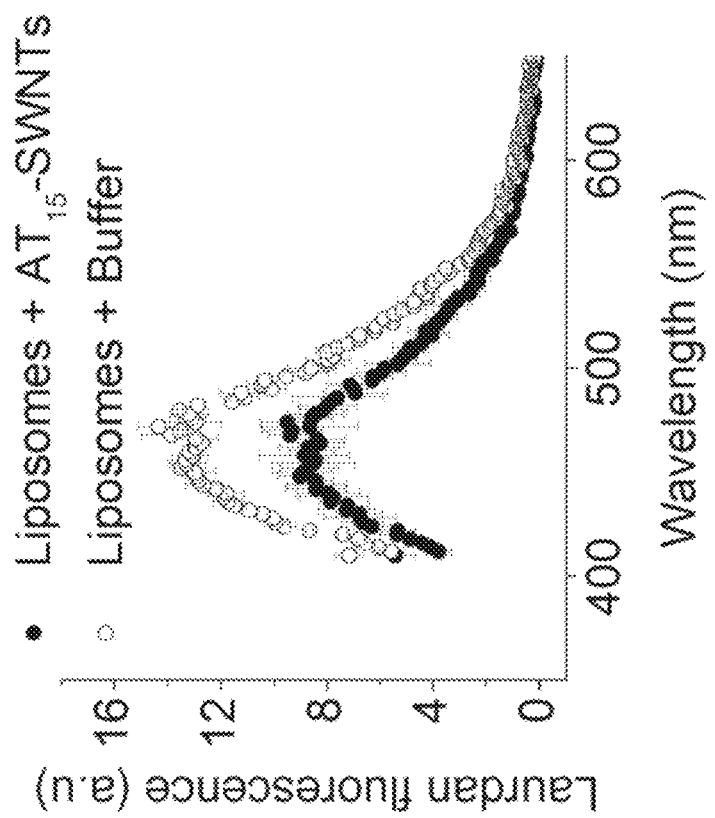
FIG. 8 is a graph representing the Laurdan fluorescence as a function of an emission wavelength.
Figure 9:
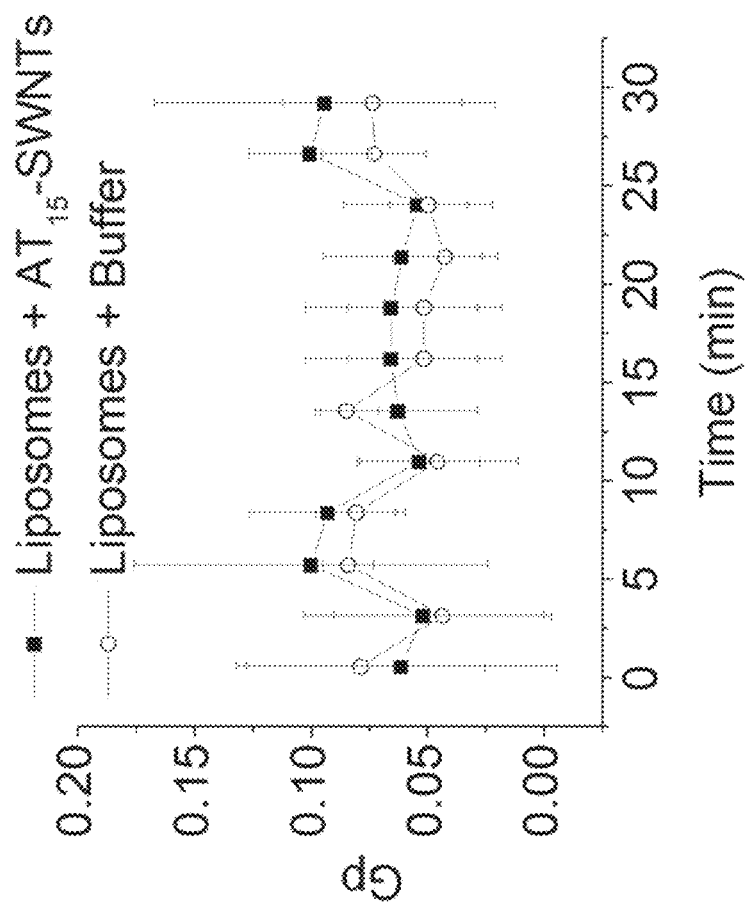
FIG. 9 is a graph representing the Laurdan generalized polarization as a function of time.

SWNT movement through chloroplast membranes may occur via passive mechanisms. Neither variation in temperature from 4 to 24° C. nor light conditions appeared to influence chloroplast ss(AT)$_{15}$-SWNT uptake (FIG. 7). Previous studies of protein transport inside chloroplasts have used temperature as an indicator of metabolic activity and light conditions as a proxy for ATP generation[23]. (Leheny, E. A. & Theg, S. M. Apparent Inhibition of Chloroplast Protein Import by Cold Temperatures Is Due to Energetic Considerations Not Membrane Fluidity. *Plant Cell* 6, 427-437 (1994), which is incorporated by reference in its entirety). Together these results suggest that SWNTs were transported through the chloroplast membranes in a process driven by diffusion and spontaneous surface reaction. Consistent with our results, it has been reported that carboxylated SWNTs localize in mitochondria, an organelle lacking endocytic pathways. (Ma, X. et al. Single-Walled Carbon Nanotubes Alter Cytochrome c Electron Transfer and Modulate Mitochondrial Function. *ACS Nano* 6(12), p. 10486-96 (2012), which is incorporated by reference in its entirety). The adsorption of chloroplast lipids on the SWNT surface seemed to occur without a shift in laurdan fluorescence, an indicator of membrane fluidity (FIGS. 8 and 9). However, laurdan fluorescence quenching points to an interaction of the fluorophore with membrane bound SWNTs.

Figure 3:
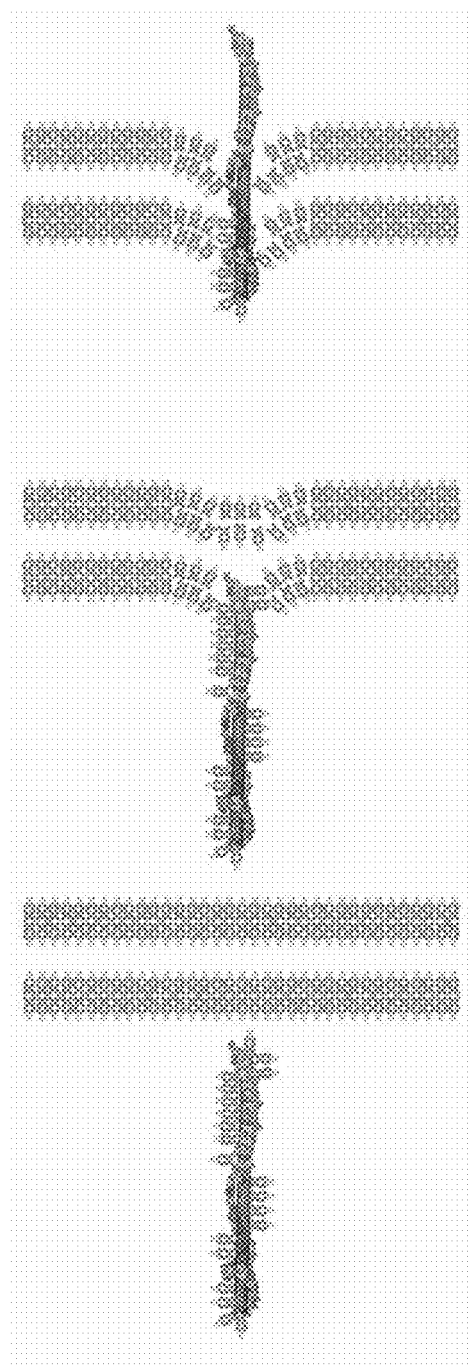
FIG. 3 is a schematic of nanoparticle transport through a chloroplast double membrane envelope (outer lipid membrane) via kinetic trapping by lipid exchange.
Figure 4:
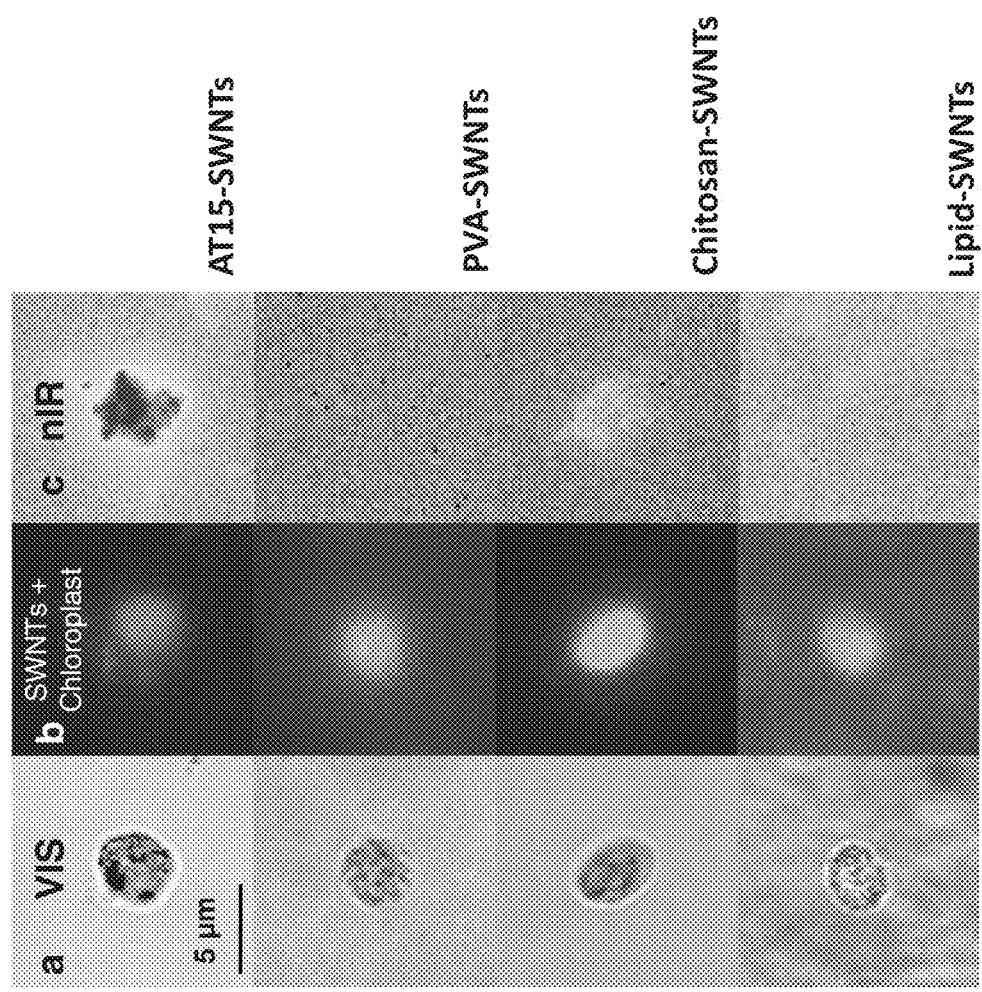
FIG. 4 includes images of nanoparticle uptake by chloroplasts.
Figure 5:
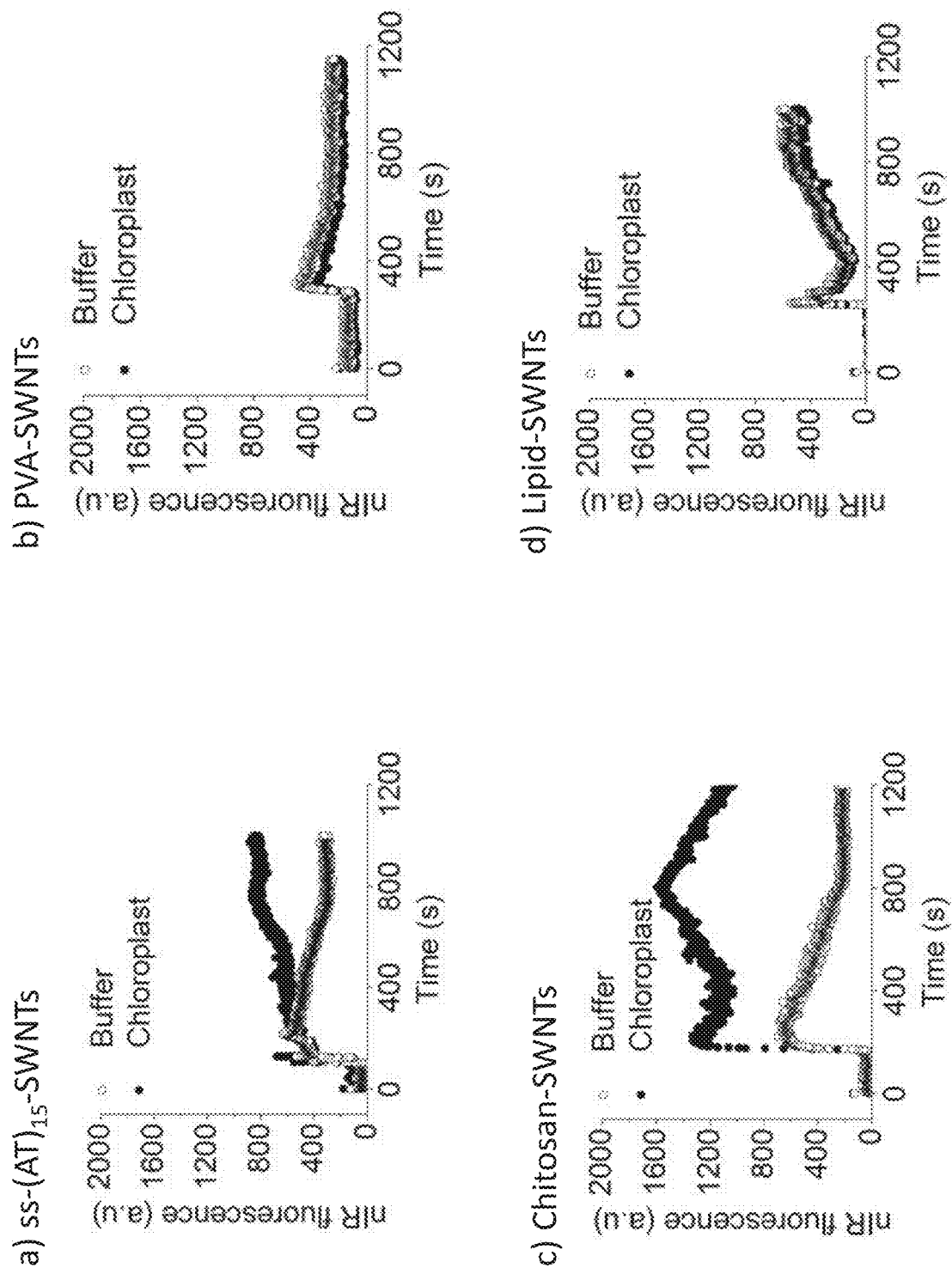
FIG. 5 includes graphs representing the change in average nanoparticle fluorescence in cross sections of chloroplasts versus external buffer solution. Laser excitation was 785 nmat 75 μW.

SWNT penetration through the chloroplast lipid bilayer may occur via kinetic trapping by lipid exchange (FIG. 3). Glycerolipids, forming the majority of chloroplast outer envelope (2.5-3 mg lipids mg protein$^{-1}$), wrap around SWNTs as they interact with the membrane. (Block, M. a, Douce, R., Joyard, J. & Rolland, N. Chloroplast envelope membranes: a dynamic interface between plastids and the cytosol. *Photosynth. Res.* 92, 225-44 (2007), which is incorporated by reference in its entirety). The disruption of the chloroplast membranes may lead to lipid adsorption to the hydrophobic SWNT surface. As nanotubes penetrate through the envelopes, they may be coated with a layer of lipids that can irreversibly bind them to the chloroplast interior. The lipid membrane may then re-heal after the nanoparticle uptake process is completed. This nanoparticle-enabled uptake mechanism through lipid bilayers could serve as a pathway for material delivery into plant organelles.

Figure 10:
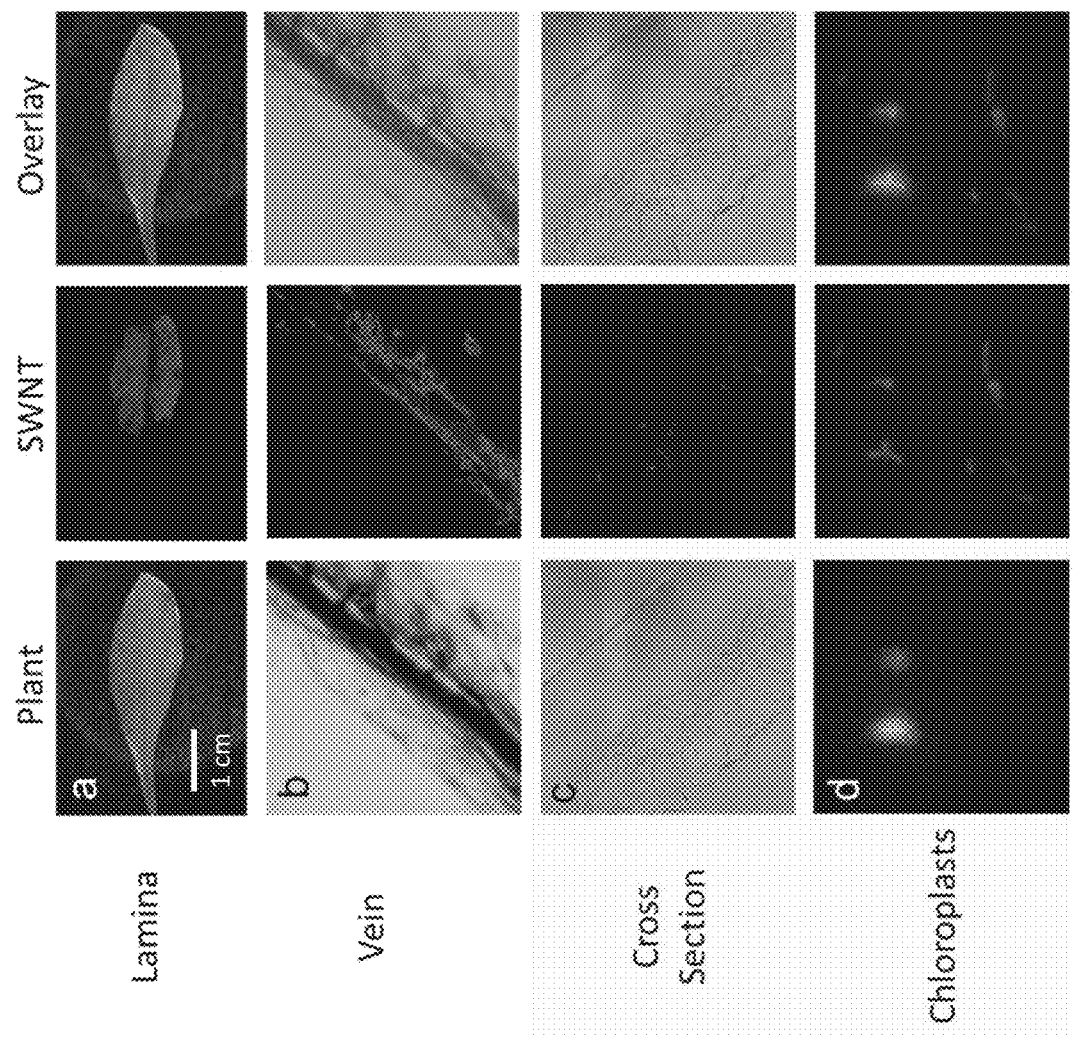
FIG. 10 includes images and graphs demonstrating nanoparticle transport inside chloroplasts and leaves.
Figure 10:
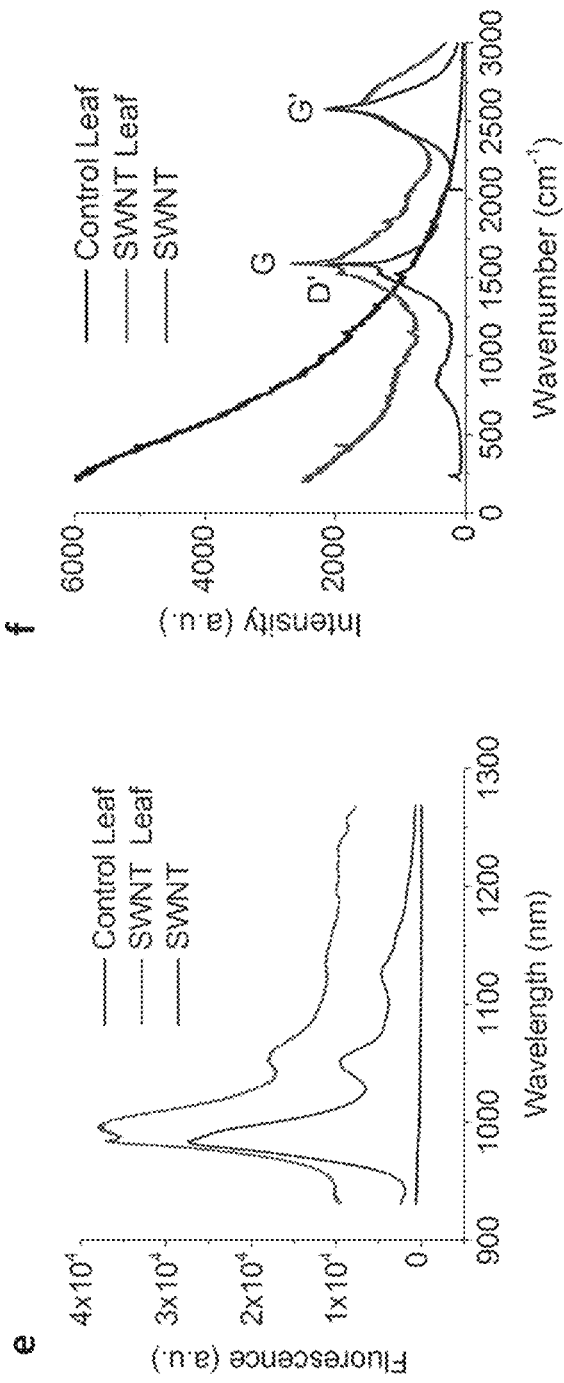
Figure 10:
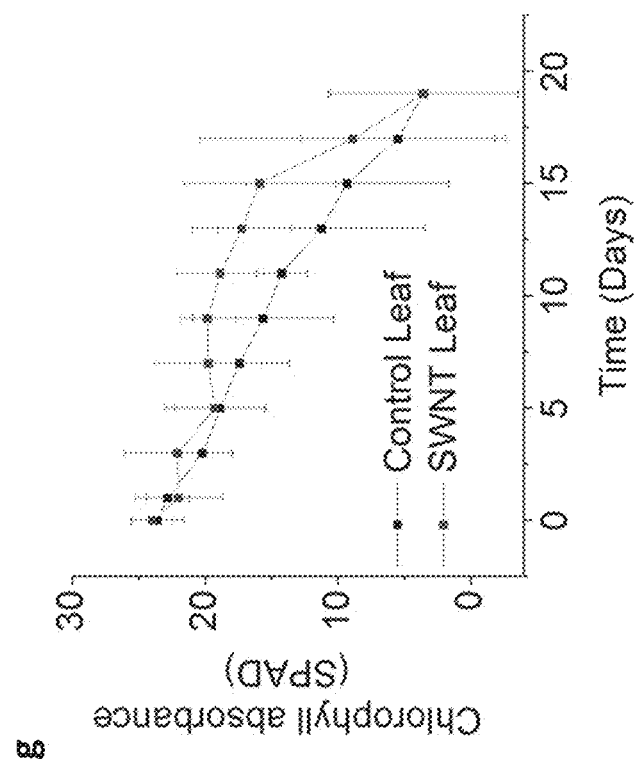

The ss(AT)$_{15}$-SWNTs were also delivered to chloroplasts of *Arabidopsis thaliana* leaves in vivo by infiltration through the leaf lamina (FIGS. 10 and 23). Leaves assembled with CoMoCAT ss(AT)$_{15}$-SWNTs showed a characteristic fluorescence peak for the 6.5 chirality (980 nm) throughout the lamina in both Cri Maestro images and the nIR spectrum (FIGS. 10(a) and 10(e)). A sharp peak shoulder in SWNT Leaf nIR fluorescence was attributed to the Raman scattering in carbon nanotubes. The Raman spectra of ss(AT)$_{15}$-SWNTs inside leaves was similar to nanoparticles in suspension except for a broadening of the G and G' bands (FIG. 10(f)). SWNTs have been previously shown to penetrate cell walls and membranes of tobacco cell cultures. (Liu, Q. L. et al. Carbon Nanotubes as Molecular Transporters for Walled Plant Cells. *Nano Lett.* 9, 1007-1010 (2009), which is incorporated by reference in its entirety). By imaging leaf tissue cross sections, ss(AT)$_{15}$-SWNTs were localized to the leaf veins and both in intracellular and extracellular parenchyma tissues (FIGS. 2 and 3), indicating transport through leaf cell membranes and walls. Colocalization images of chloroplast and nIR SWNT fluorescence indicated that SWNTs were associated with chloroplasts inside parenchyma cells (FIG. 10(d)). No SWNT nIR fluorescence was detected in control leaves treated with only infiltration medium (FIG. 23). Leaf lifespan was not affected by infiltration with ss(AT)$_{15}$-SWNTs at 5 mg/L (FIG. 10(g)). Leaf chlorophyll content has been used as a proxy for indicating the timing of leaf senescence, a type of programmed cell death in which the photosynthetic machinery is dismantled. (Lim, P. O., Kim, H. J. & Nam, H. G. Leaf senescence. *Annu. Rev. Plant Biol.* 58, 115-36 (2007), which is incorporated by reference in its entirety). Both SWNT leaves and control leaves treated with infiltration medium showed similar temporal patterns in chlorophyll content for 20 days until the end of leaf lifespan.

Figure 24:
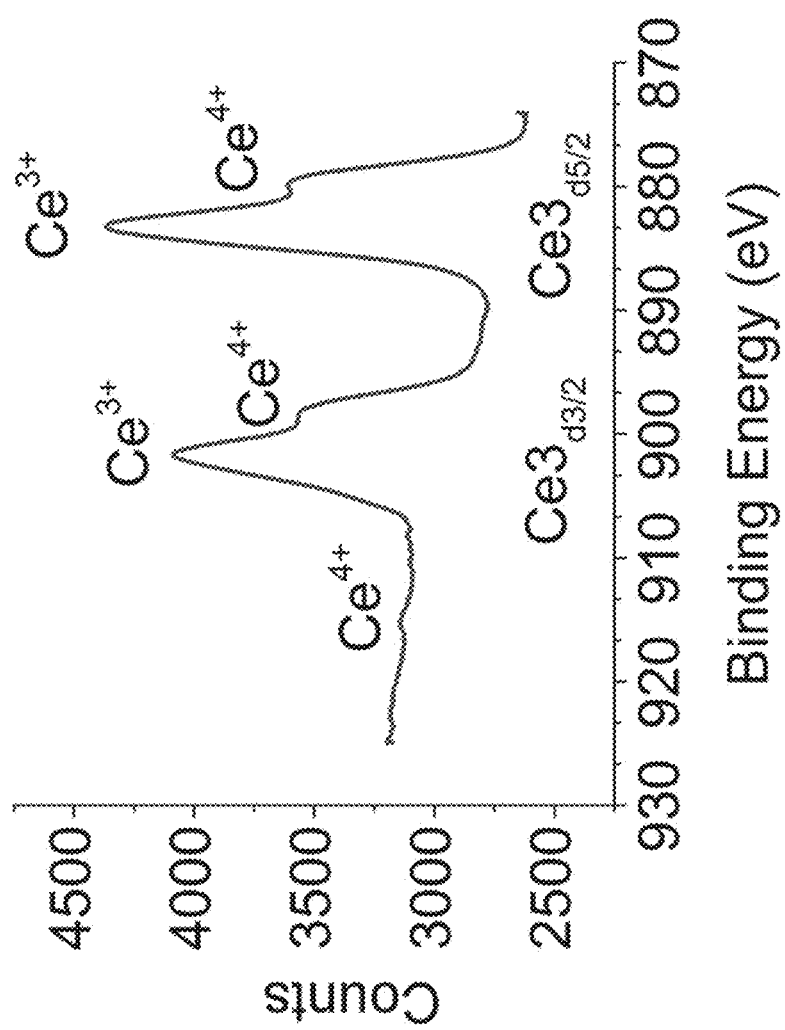
FIG. 24 is a graph representing the x-ray photoelectron spectra for PAA-nanoceria.
Figure 25:
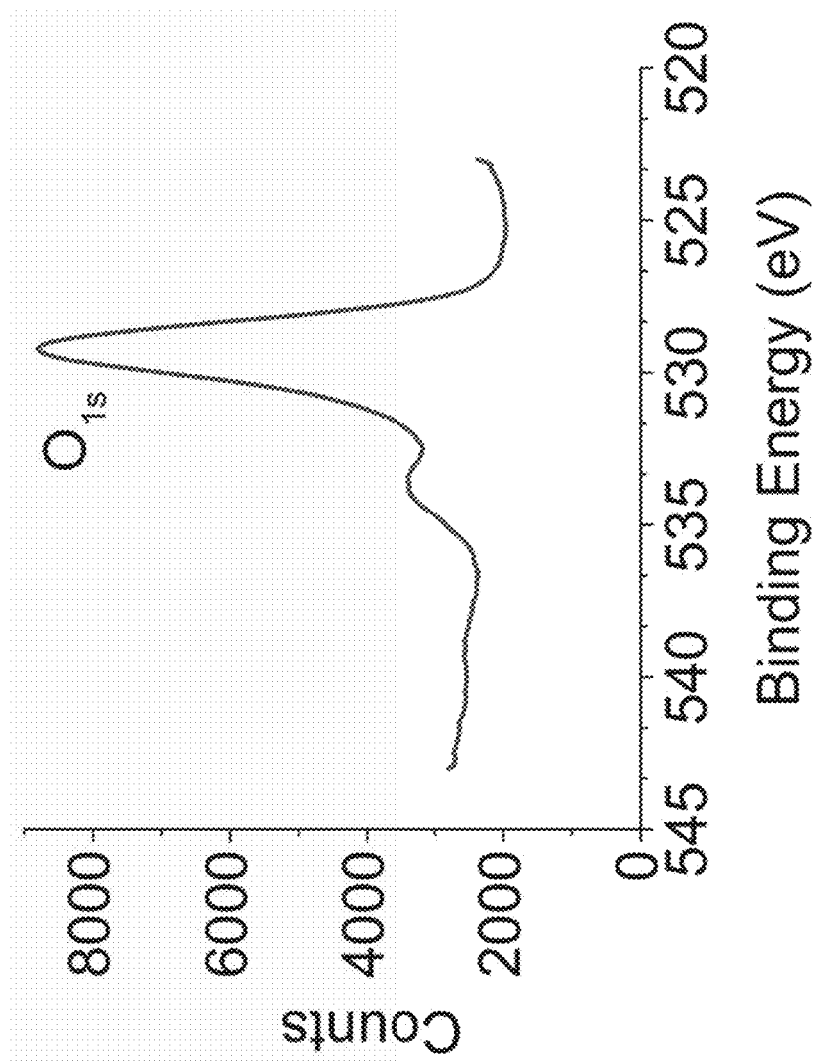
FIG. 25 is a graph representing the oxygen binding energy corresponding to metal oxide.

A compelling application of this spontaneous transport and assembly of SWNTs within the chloroplast could be to localize other nanoparticles within the envelope, and ultimately, on the thylakoid membranes. Nanoceria may be one of the most potent reactive oxygen scavengers available and can have the potential to significantly reduce ROS generation at the sites of generation. However, no mechanism is known for synthesizing these particles within chloroplast membranes. Nanoceria can interchange oxidation states between $Ce^{3+}$ and $Ce^{4+}$, forming oxygen vacancies with dangling $Ce^{3+}$ bonds (FIGS. 24 and 25). (Deshpande, S., Patil, S., Kuchibhatla, S. V. & Seal, S. Size dependency variation in lattice parameter and valency states in nanocrystalline cerium oxide. *Appl. Phys. Lett.* 87, 133113 (2005), which is incorporated by reference in its entirety). Lattice strains can promote the formation of defect sites with regeneration of the $Ce^{3+}$ oxidation state via redox cycling reactions. Thus, nanoceria may be positioned to catalytically scavenge hydroxyl and superoxide radicals at chloroplast sites of generation via the following reactions:

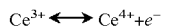
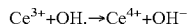
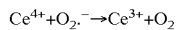

Figure 11:
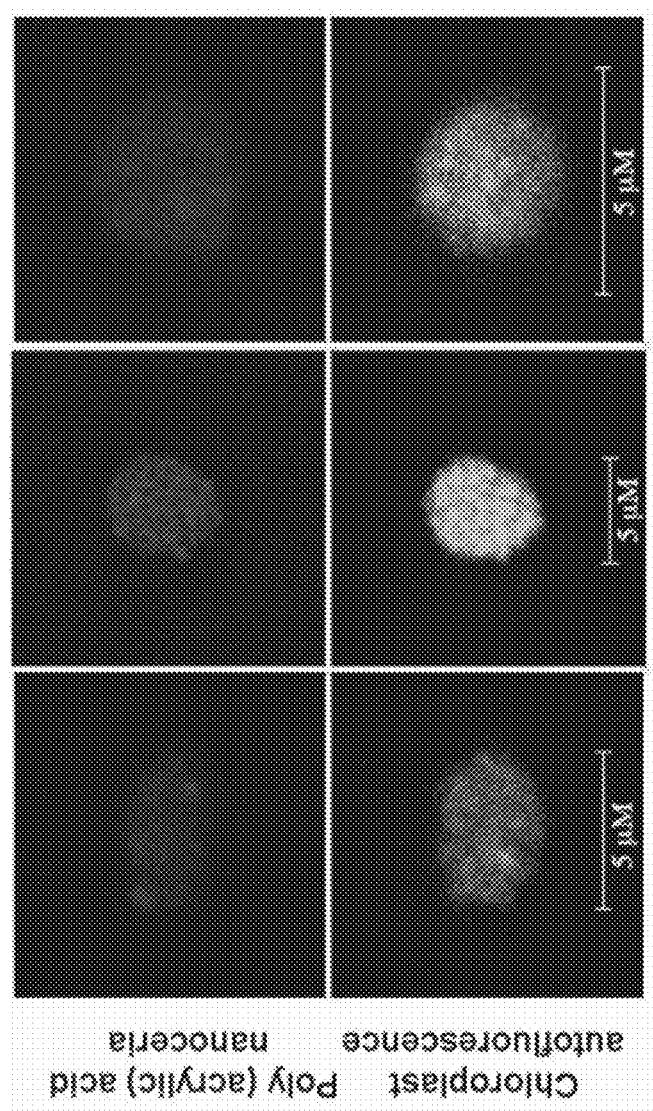
FIG. 11 includes confocal images of pigment fluorescence colocalized with nanoceria particles labeled with a fluorophore.
Figure 12:
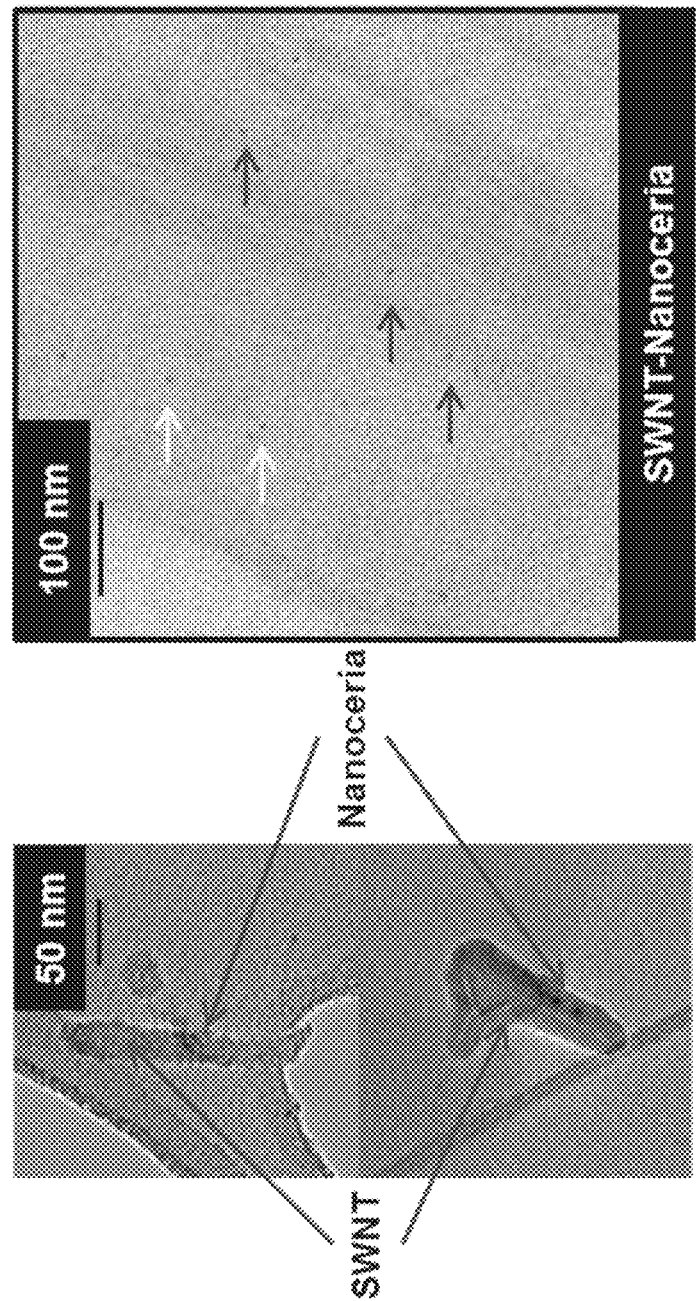
FIG. 12 includes TEM images of SWNT-nanoceria complexes inside chloroplasts.
Figure 26:
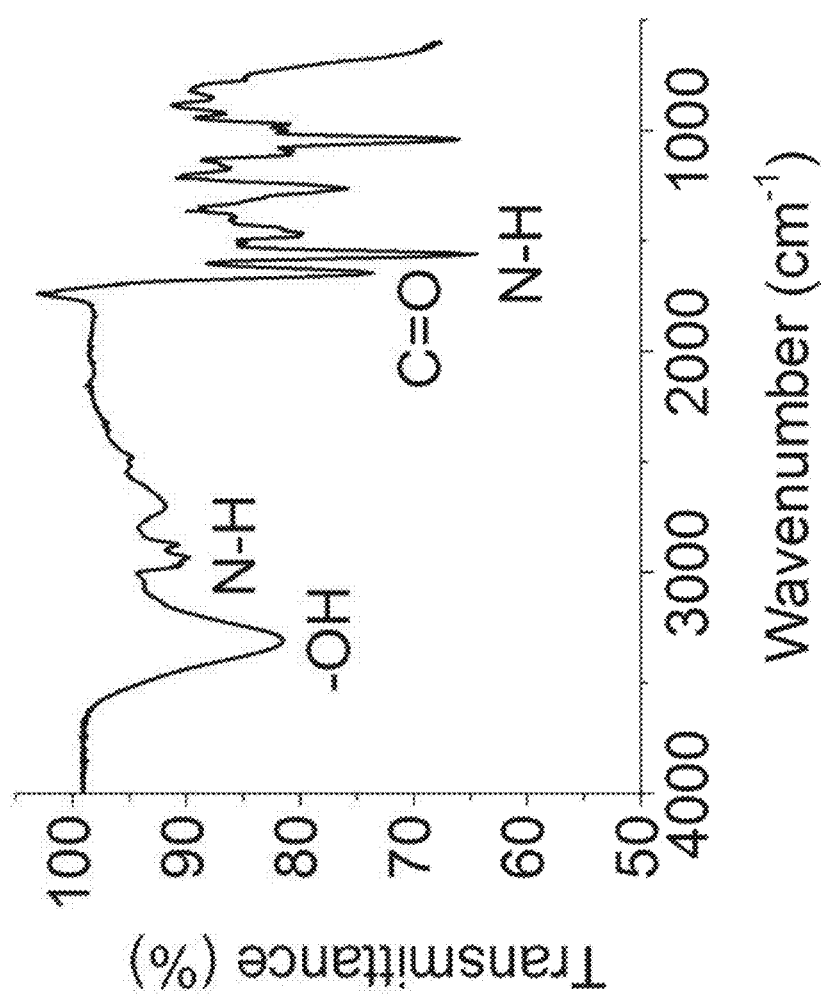
FIG. 26 is a graph representing the percent transmittance as a function of wavenumber for Fourier-transform infrared spectroscopy.
Figure 27:
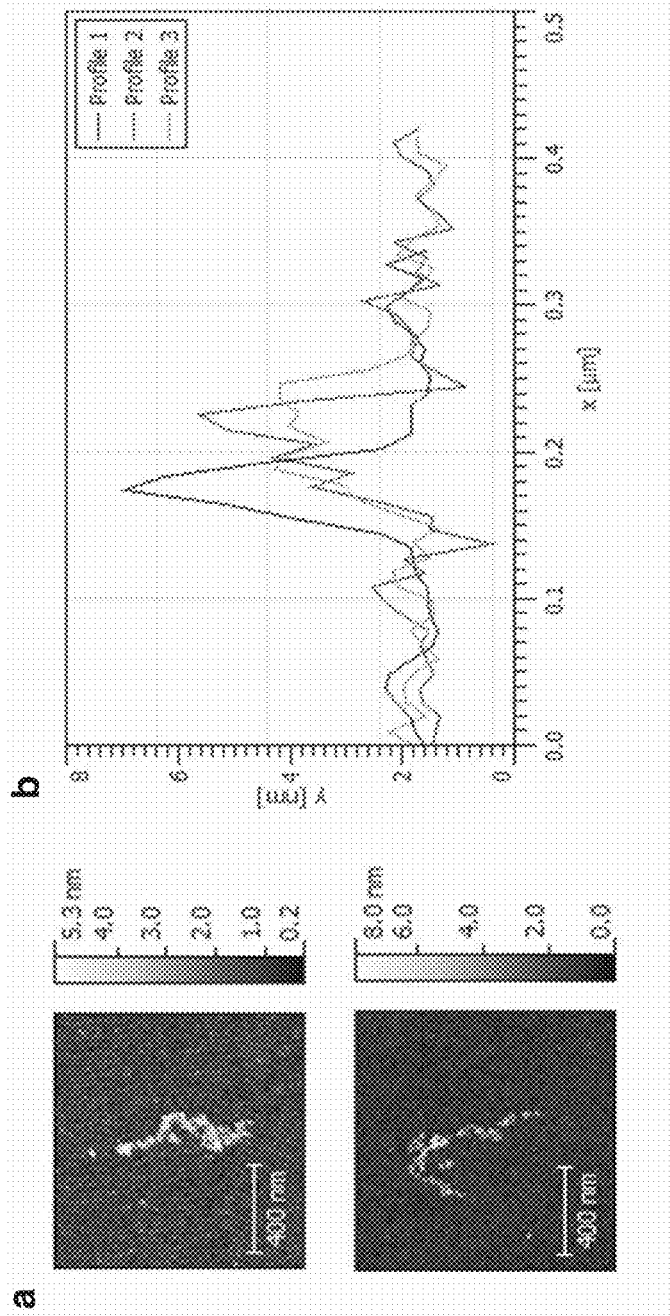
FIG. 27(a) is an atomic force microscopy image of a SWNT-nanoceria complex.
FIG. 27(b) is a graph representing the height profile of a SWNT-nanoceria complex.
Figure 28:
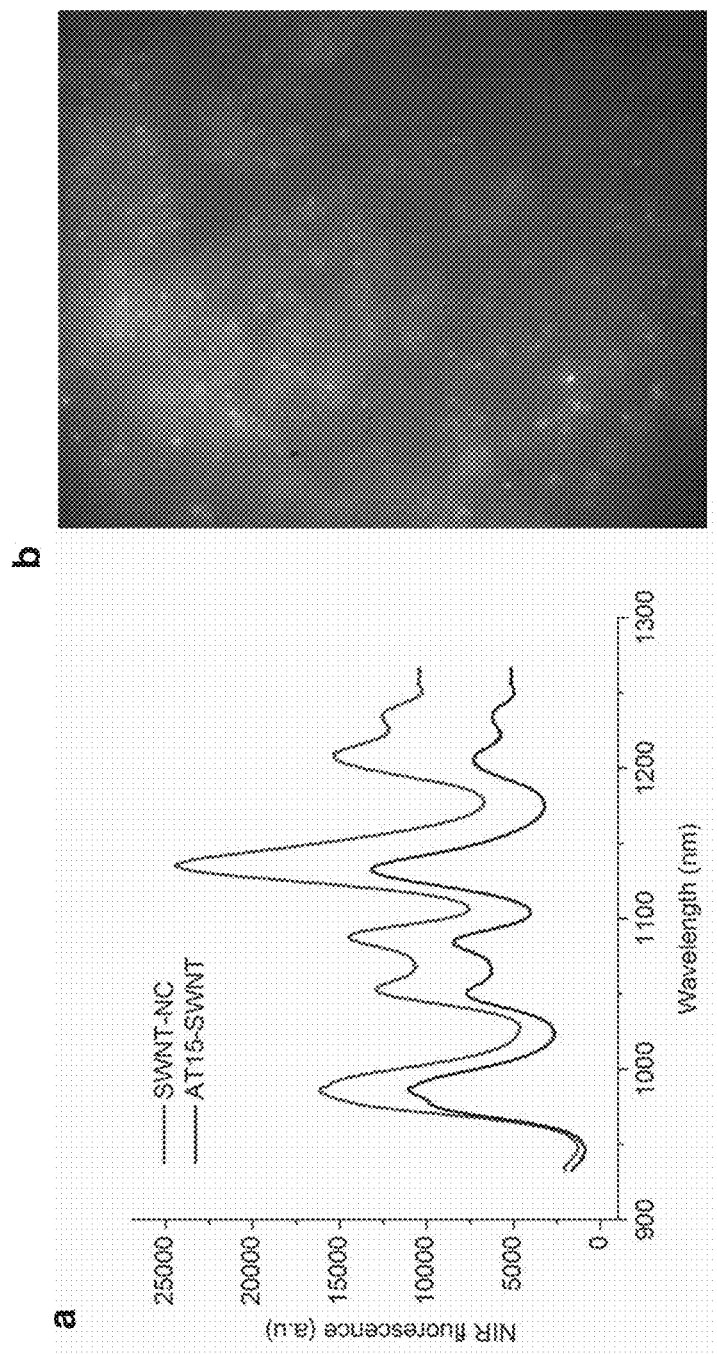
FIG. 28(a) is a graph representing nIR fluorescence of a SWNT, before and after conjugation with nanoceria.
FIG. 28(b) is a nIR image of single particle SWNT-nanoceria in buffer solution at a laser excitation of 658 nm.
Figure 29:
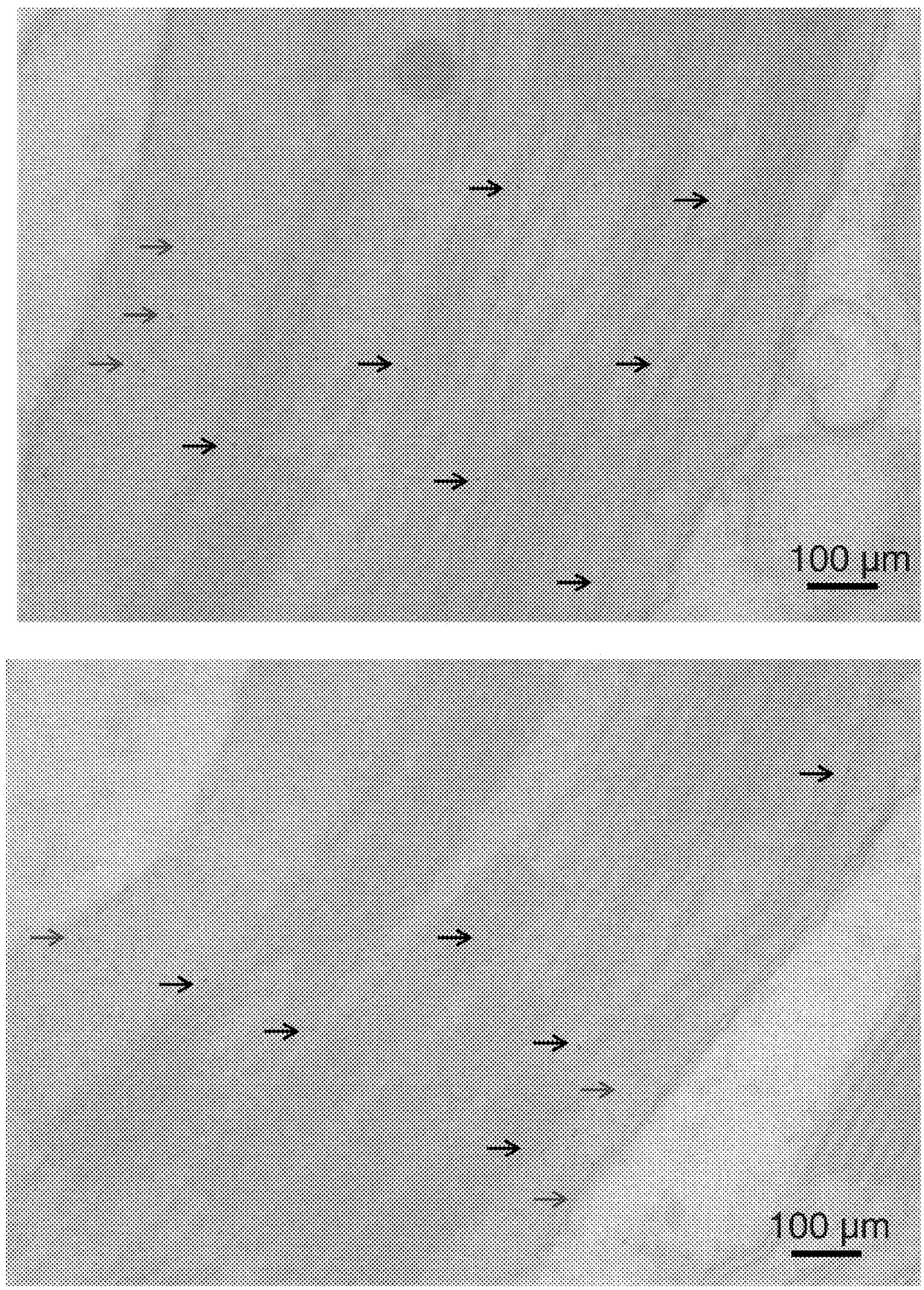
FIG. 29 includes TEM images of SWNT-nanoceria complexes inside extracted chloroplasts.
Figure 30:
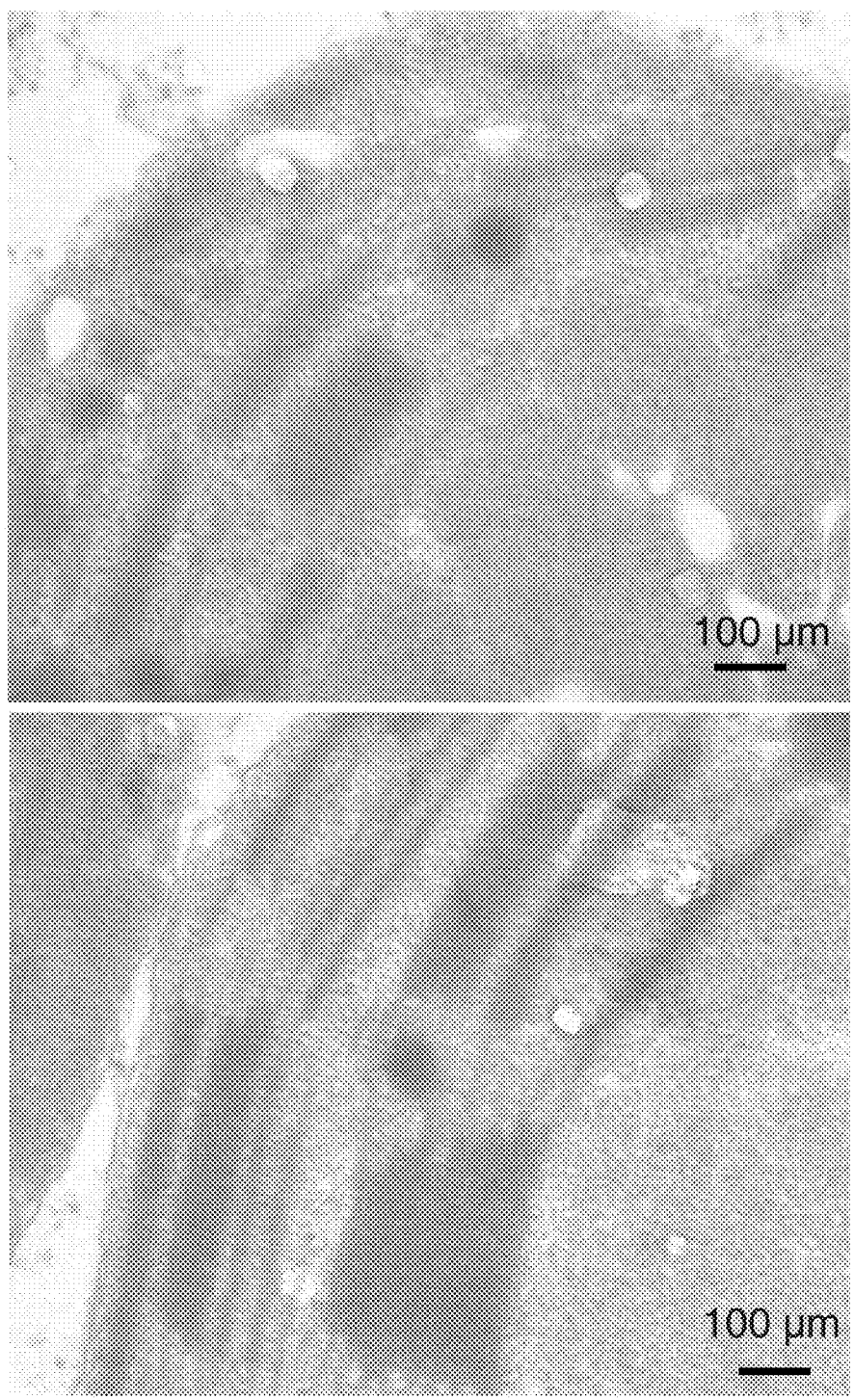
FIG. 30 includes TEM images of extracted chloroplasts without nanoparticles.
Figure 31:
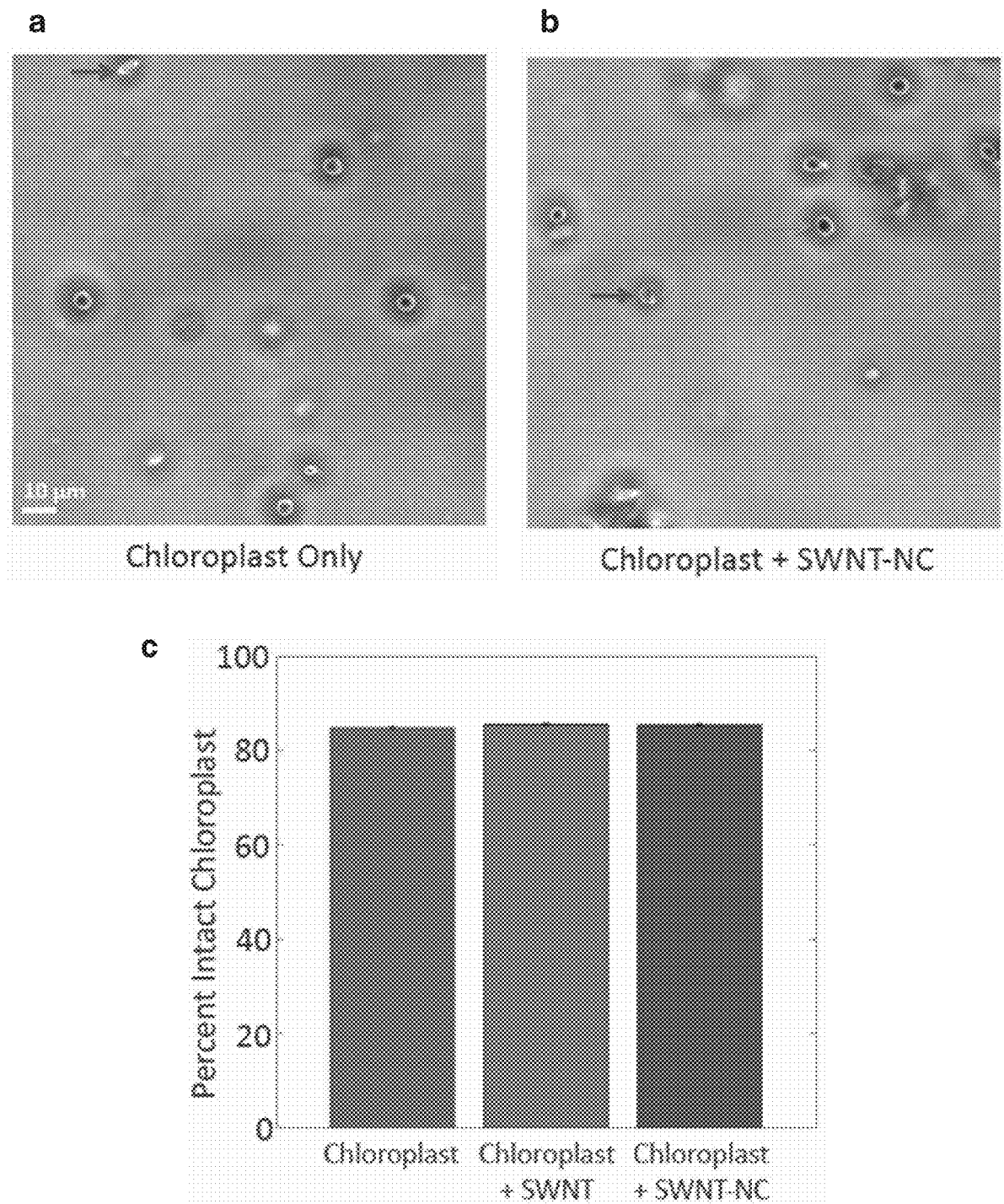
FIG. 31(a) is an image of chloroplasts only.
FIG. 31(b) is an image of chloroplasts containing SWNT-nanoceria complexes.
FIG. 31(c) is a bar graph representing the percent intact chloroplasts in samples of chloroplasts, chloroplasts containing SWNTs, chloroplasts containing SWNT-nanoceria complexes.
Figure 32:
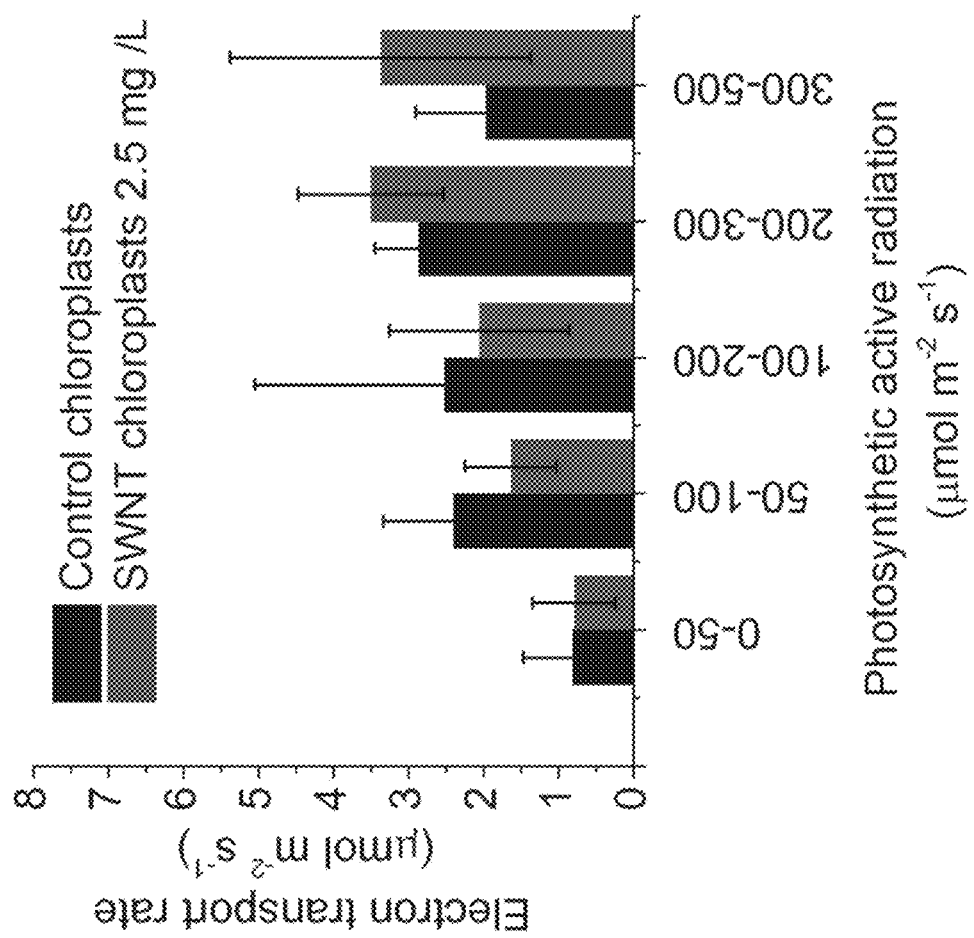
FIG. 32 is a bar graph representing the electron transport rate for chloroplasts or SWNT chloroplasts at various photosynthetic active radiation levels.
Figure 33:
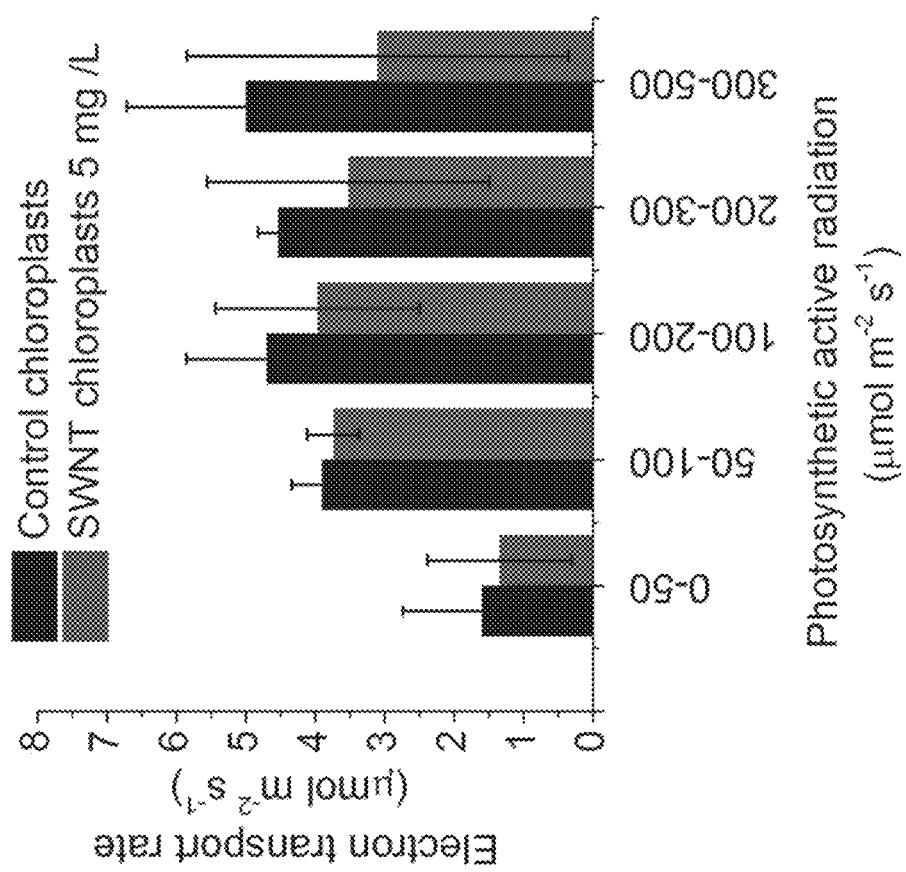
FIG. 33 is a bar graph representing the electron transport rate for chloroplasts or SWNT chloroplasts at various photosynthetic active radiation levels.
Figure 34:
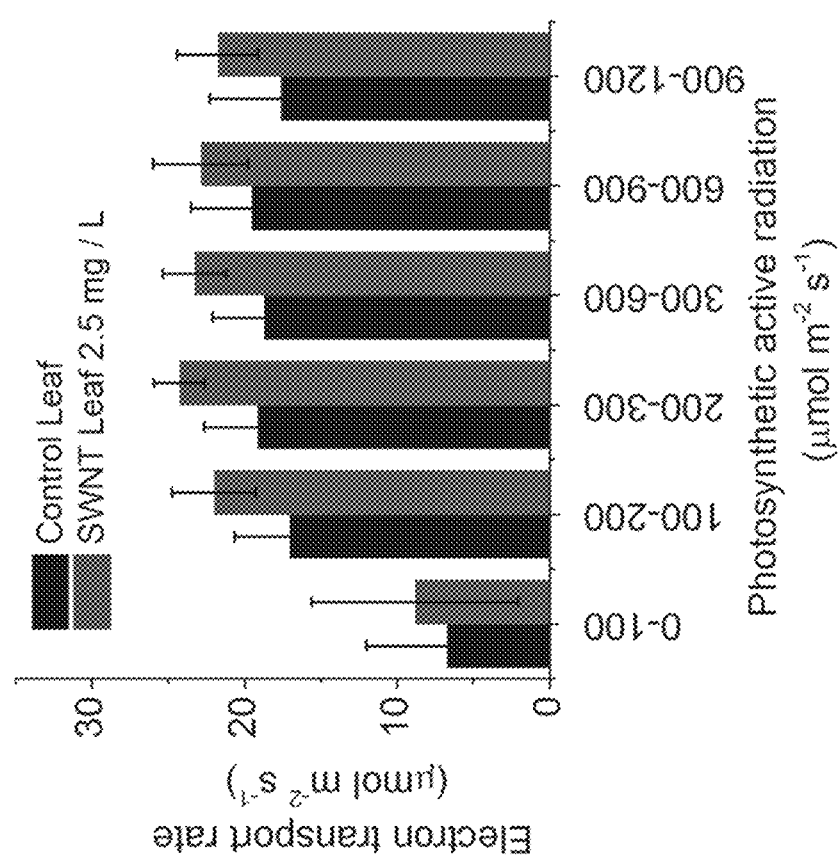
FIG. 34 is a bar graph representing the electron transport rate for leaves or SWNT leaves at various photosynthetic active radiation levels.

Previous studies demonstrated the potential of dextran-wrapped nanoceria as ROS scavengers for isolated chloroplasts and microalgae despite their inability to move through lipid bilayers and cell walls. (Boghossian, A. A. et al. (2013); Sicard, C. et al. CeO2 Nanoparticles for the Protection of Photosynthetic Organisms Immobilized in Silica Gels. *Chem. Mater.* 23, 1374-1378 (2011), each of which is incorporated by reference in its entirety). It is possible that dextran-wrapped nanoceria did not interact with the chloroplast membrane due to their neutral zeta potential. (Asati, A., Santra, S., Kaittanis, C. & Perez, J. M. Surface-charge-dependent cell localization and cytotoxicity of cerium oxide nanoparticles. *ACS Nano* 4, 5321-31 (2010), which is incorporated by reference in its entirety). It is possible that nanoceria particles with a high negative or positive zeta potential can localize within the chloroplast envelope. Confocal images demonstrated that negatively charged poly (acrylic acid) nanoceria (PAA-NC) co-localize with chlorophyll molecules inside isolated chloroplasts (FIG. 11). (Asati, A., et al. (2010)). A mechanism of chloroplast nanoparticle uptake may also extend to a nanomaterial of SWNTs conjugated with PAA-NC via carbodiimide chemistry (SWNT-NC). In brief, SWNT-NC were synthesized from HiPCO SWNTs (Unidym) suspended with a 30-base (dAdT) sequence of ssDNA ($AT_{15}$) functionalized with amino groups at the 5' end (Integrated DNA Technologies). The PAA-NC and 5'amino-ss($AT)_{15}$-SWNTs were conjugated with a zero cross link carbodiimide agent N-ethyl-N'-(3-dimethylaminopropyl) carbodiimide hydrochloride (EDAC) (Sigma Aldrich). The solution was purified from reagents by bench top centrifugation using a 100 K Amicon membrane (Millipore). Fourier transform infra-red spectroscopy (FTIR) indicates the formation of amide bonds between amino groups at the 5' end of DNA wrapped ss($AT)_{15}$-SWNTs and the hydroxyl groups of PAA-NC (FIG. 26). The size of SWNT-NC complexes determined by atomic force microscopy (AFM) and transmission electron microscopy (TEM) was in the range of several hundred nanometers in length and four to seven nanometers in height (FIG. 27). TEM image analysis showed that 55±7% SWNT were conjugated with 4±2 nanoceria particles on average (FIG. 12). The conjugation of NC with SWNTs by carbodiimide chemistry produced individual SWNT-NC complexes with characteristic peaks in n-IR fluorescence (FIG. 28). These SWNT-NC complexes were able to penetrate the chloroplast envelope and assembled within photosynthetic machinery (FIGS. 12, 29 and 30). The nanoparticles localized in proximity to the chloroplast thylakoid membranes and stroma in which the light and carbon reactions of photosynthesis occur, respectively. Chloroplast intactness after being interfaced with SWNTs and SWNT-NC remained unchanged at approximately 85% (FIG. 31).

Semiconducting SWNTs Increase and Extend Chloroplast Photosynthetic Activity

Figure 15:
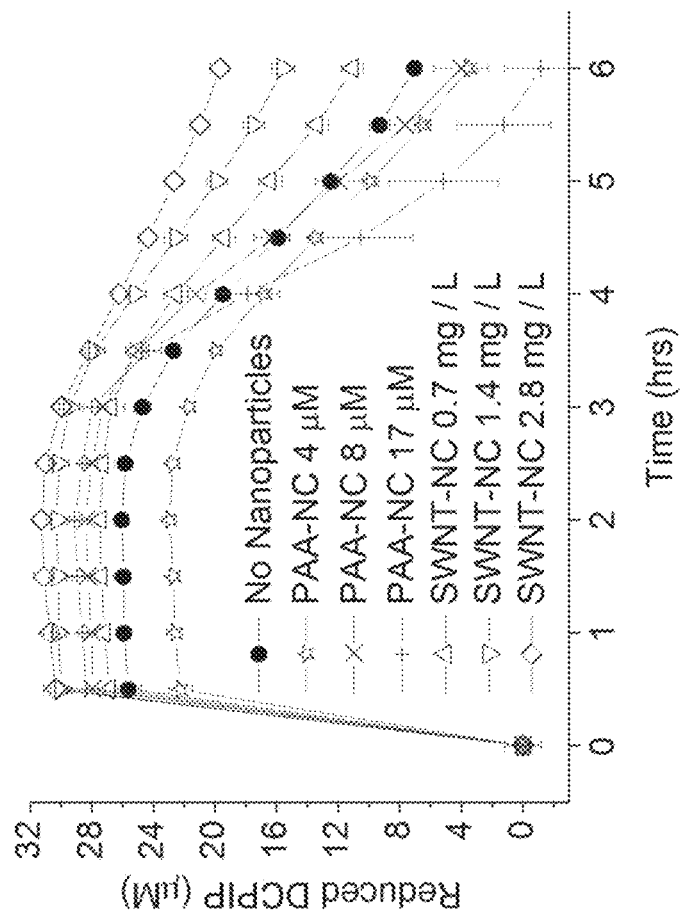
FIG. 15 is a graph representing the concentration of reduced DCPIP as a function of time showing the photosynthetic activity of isolated chloroplasts with nanoparticles.
Figure 16:
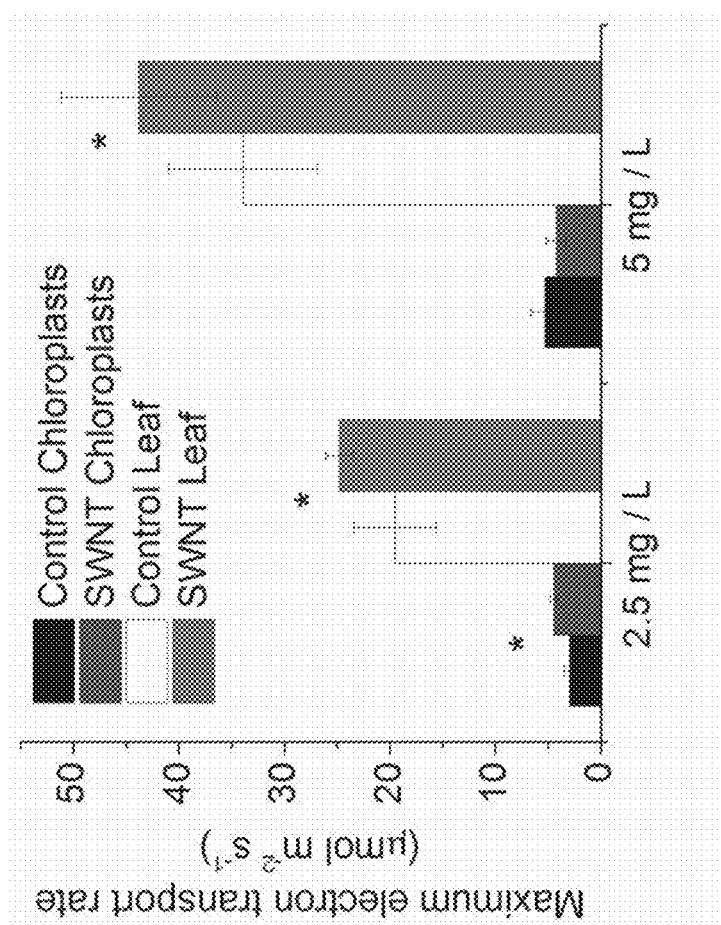
FIG. 16 is a bar graph representing maximum electron transport rates in extracted chloroplasts and leaves as quantified by chlorophyll fluorescence.
Figure 17:
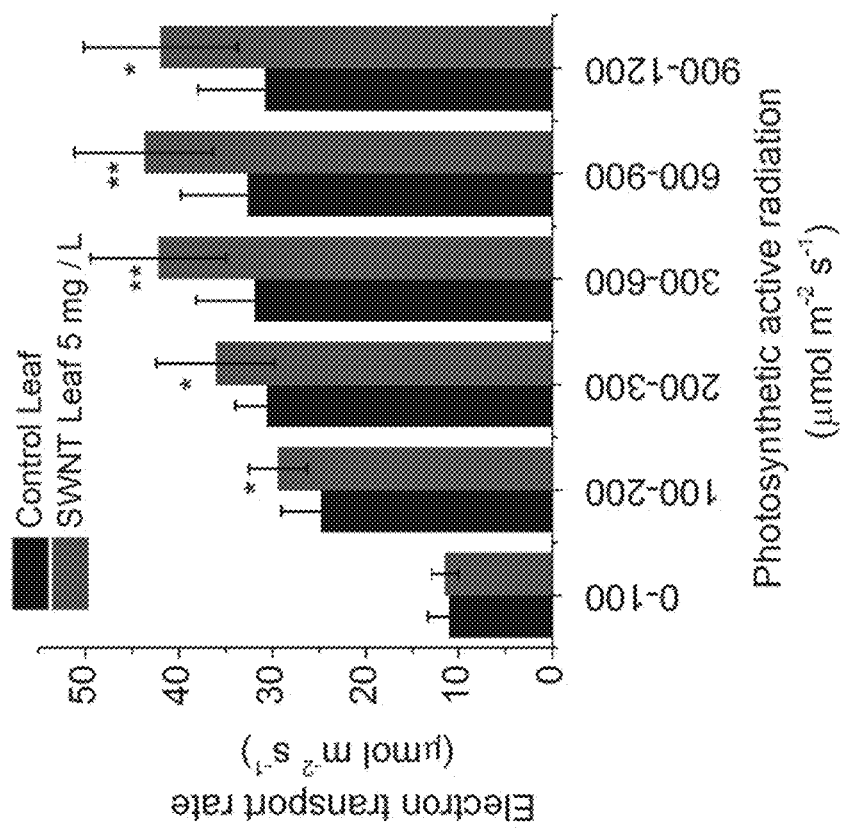
FIG. 17 is a bar graph representing the electron transport rate at various photosynthetic active radiation levels.

Enhanced and extended photosynthetic activity by passive assembly of extracted chloroplasts with SWNT-NC was shown by higher reduction rates of the electron acceptor dye dichlorophenolindophenol (DCPIP) (FIG. 15). DCPIP can intercept electrons transported from photosystem II to photosystem I in the chloroplast photosynthetic machinery. (Lonergan, T. A. & Sargent, M. L. Regulation of the Photosynthesis Rhythm in Euglena gracilis CS1-75. *Plant Physiol.* 64, 99-103 (1979), which is incorporated by reference in its entirety). PAA-NC interfaced with chloroplasts had an optimum concentration at 8 µM, showing slightly higher photosynthetic activity for the initial 3.5 hours followed by complete deactivation of photosynthetic electron transport after 6 hours. However, a control sample of DCPIP and PAA-NC in buffer showed similar reduction indicating that PAA-NC did not significantly improve photosynthetic activity (FIGS. 35-39). SWNT-NC particles had the strongest effect on photosynthetic activity with more than three times higher chloroplast DCPIP reduction than the control after 6 hours. This suggested that the presence of SWNT, not NC, may be the cause of enhanced photosynthetic activity for SWNT-NC, instead of ROS scavenging. While it appeared that the observed scavenging of ROS did not significantly improve photosynthetic activity, it may be beneficial for other processes, such as the carbon fixation reactions. Extracted chloroplast photosynthesis was also quantified by measuring the yield of chlorophyll fluorescence using a MINI-PAM photosynthesis analyzer (WALZ). Maximum electron transport rates of light adapted chloroplasts were significantly increased by 49% with SWNTs at 2.5 mg/L (FIG. 16). Remarkably, SWNTs also enhanced the light reactions of photosynthesis of chloroplasts inside leaves in vivo. Leaves infiltrated with 2.5 and 5 mg/L of SWNTs showed a 27% and 31% increase in maximum electron transport rates over leaves without SWNTs, respectively (FIG. 16). Rates of electron transport were also higher with photosynthetic active radiations above 100 µmol $m^{-2}$ $s^{-1}$ in leaves with SWNTs at 5 mg/L, but no effect was observed in extracted chloroplasts (FIGS. 17, 32, 33 and 34). The difference in this behavior could have been due to variations in optimum light levels for photosynthesis in extracted chloroplasts versus chloroplasts in leaves. Together the results indicate that SWNTs were able to enhance solar energy conversion of chloroplasts both in vivo and ex vivo.

Figure 18:
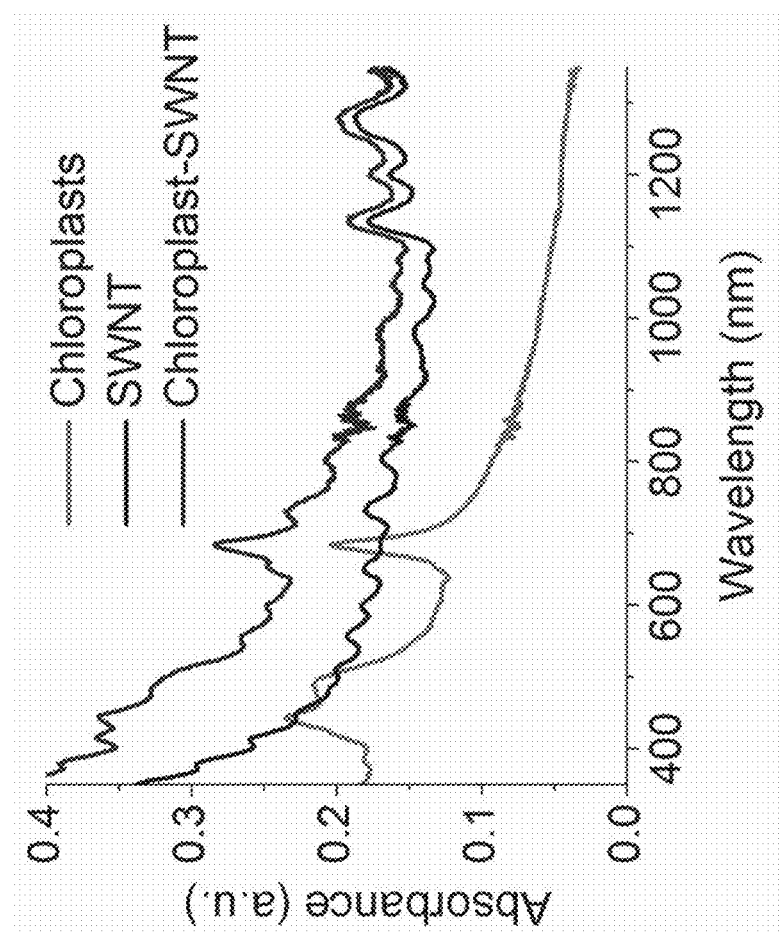
FIG. 18 is a graph representing absorption spectrums of chloroplasts, SWNTs, and chloroplasts containing SWNTs.
Figure 19:
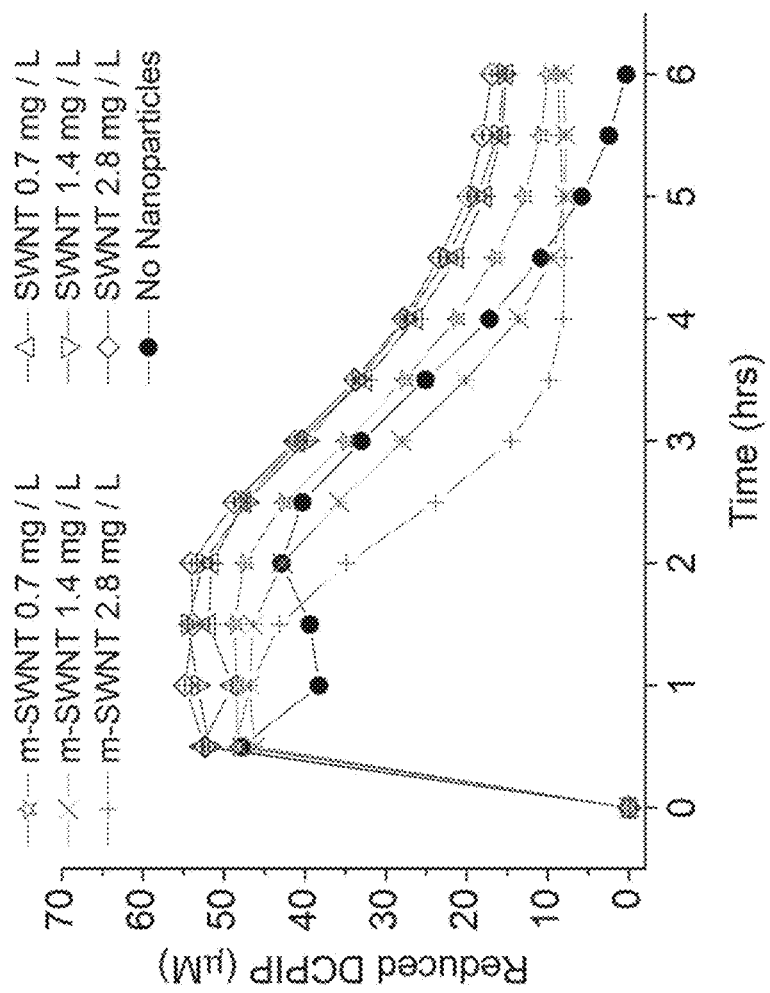
FIG. 19 is a graph representing the amount of chloroplast reduction of DCPIP in the presence of SWNTs or m-SWNTs.

One possible explanation for the enhancement of photosynthetic activity by SWNTs is electron transfer between SWNTs and chloroplasts. SWNTs have been reported to generate a photoelectrohemical current upon dynamic assembly with extracted reaction centers and nanodisc lipids. (Ham, M.-H. et al. Photoelectrochemical complexes for solar energy conversion that chemically and autonomously regenerate. *Nat. Chem.* 2, 929-36 (2010), which is incorporated by reference in its entirety). Electron transfer between carbon nanotubes and photosynthetic machinery has been demonstrated, including recently between nanotubes and spinach thylakoids. (Boghossian, A. A., Ham, M.-H., Choi, J. H. & Strano, M. S. Biomimetic strategies for solar energy conversion: a technical perspective. *Energy Environ. Sci.* 4, 3834-3843 (2011); and Calkins, J. O., Umasankar, Y., O'Neill, H. & Ramasamy, R. P. High photo-electrochemical activity of thylakoid-carbon nanotube composites for photosynthetic energy conversion. *Energy Environ. Sci.* 6, 1891 (2013), each of which is incorporated by reference in its entirety). Thus, the assembly of SWNTs within the photosynthetic machinery may modify the chloroplast absorption profile by increasing light energy capture in UV, green, and nIR ranges of the spectrum (FIG. 18). Semiconducting SWNTs were then able to convert this absorbed light into excitons that can be transferred to the chloroplast electron transport chain (FIG. 19). To confirm this mechanism, the photosynthetic activity of extracted chloroplasts assembled with separated, metallic SWNTs (m-SWNTs) and unseparated HiPCO SWNTs (Unidym, approximately ⅓ metallic, ⅔ semiconducting) were compared. If semiconducting SWNT enhanced light capturing, then metallic SWNT should show less of an impact since metallic SWNTs (m-SWNTs) are not able to convert light energy to excitons. As expected, m-SWNTs showed a minimal effect on chloroplast reduction of the electron acceptor dye DCPIP over six hours (FIG. 19). Similar trends of nanoparticle impact on chloroplast photosynthetic activity were observed at initial rates of DCPIP reduction (FIGS. 35-38). Different concentrations of the mix of HiPCO SWNTs (Unidym) had the same increase in photosynthetic activity. However, increasing concentrations of m-SWNTs decreased the reduction of DCPIP relative to chloroplasts without nanoparticles from one to six hours. This negative effect of m-SWNTs on chloroplast photosynthetic activity, likely occurred because m-SWNTs absorb light that chloroplasts could otherwise have captured, but m-SWNTs were unable to transfer any of this energy to the electron transport chain (FIG. 40).

Cerium and Carbon Based Nanoparticles Enhance Chloroplast ROS Scavenging

Figure 13:
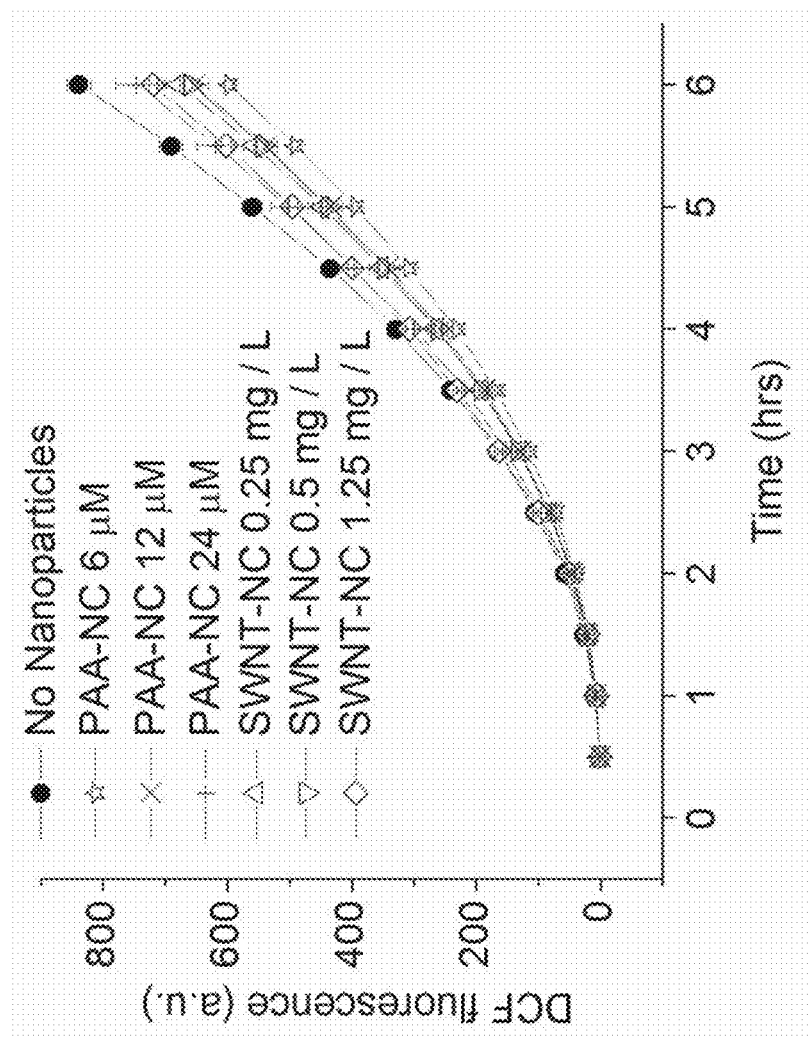
FIG. 13 is a graph representing an amount of ROS scavenging by nanoparticles inside chloroplasts as demonstrated by the oxidation of $H_2DCFDA$ to DCF.
Figure 14:
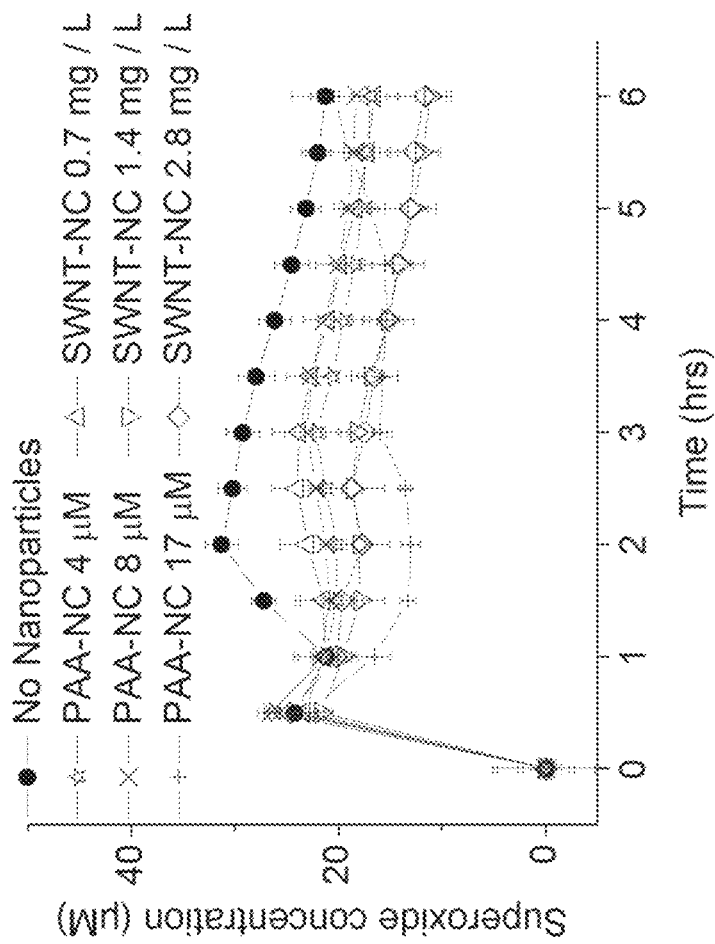
FIG. 14 is a graph representing the superoxide concentration as a function of time in the presence of various nanoparticle concentrations.

PAA-NC and SWNT-NC localized inside extracted chloroplasts significantly decreases the ROS concentration, as shown by the conversion of the dye $H_2DCFDA$ to its fluorescent form DCF (FIG. 13). $H_2DCFDA$ oxidation to DCF by a range of free radicals such as hydrogen peroxide, superoxide, nitric oxide, and peroxidases has been applied to monitor ROS generated by extracted chloroplasts. (Mubarakshina, M. M. et al. Production and diffusion of chloroplastic H2O2 and its implication to signalling. *J. Exp. Bot.* 61, 3577-87 (2010), which is incorporated by reference in its entirety). Under continuous illumination for six hours, chloroplasts interfaced with 6 µM PAA-NC showed a substantial 71.3% reduction in ROS relative to chloroplasts without nanoparticles. SWNT-NC were less effective than PAA-NC at scavenging ROS. The optimum concentration of SWNT-NC (0.5 mg $L^{-1}$) led to a 78.6% drop in chloroplast ROS generation. Superoxide concentrations considerably declined from 31.29±1.56 µM down to 12.99±0.89 µM with PAA-NC and 17.62±2.57 µM with SWNT-NC after two hours. Scavenging of short lived ROS, such as superoxide, was facilitated by the proximity of nanoparticles to the sites of ROS generation near the thylakoid membranes, providing a quick pathway for superoxide radicals to react with nanoceria $Ce^{3+}$ dangling bonds (FIG. 14). While chloroplast superoxide scavenging by 17 µM PAA-NC declined over time, other PAA-NC concentrations and all SWNT-NC concentrations maintained significantly lower levels of superoxide, with 1.4 and 2.8 mg $L^{-1}$ SWNT-NC having the maximum impact.

Figure 20:
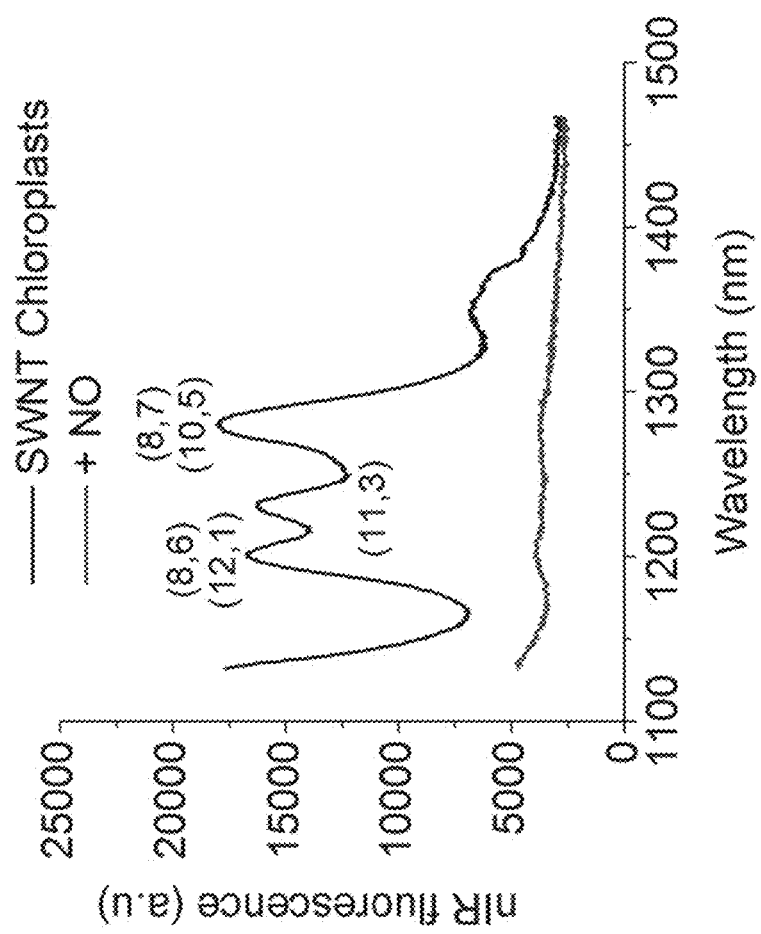
FIG. 20 is a graph representing the emission spectra of SWNT containing chloroplasts in the presence or absence of nitric oxide.
Figure 21:
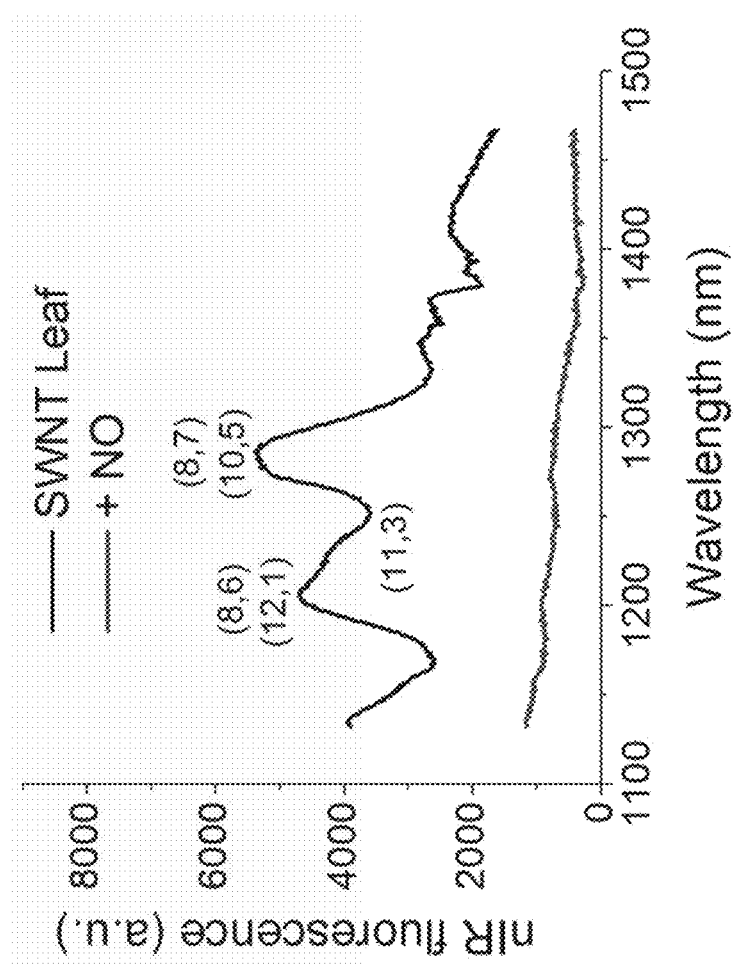
FIG. 21 is a graph representing the emission spectra of SWNT containing leaves in the presence or absence of nitric oxide.
Figure 22A:
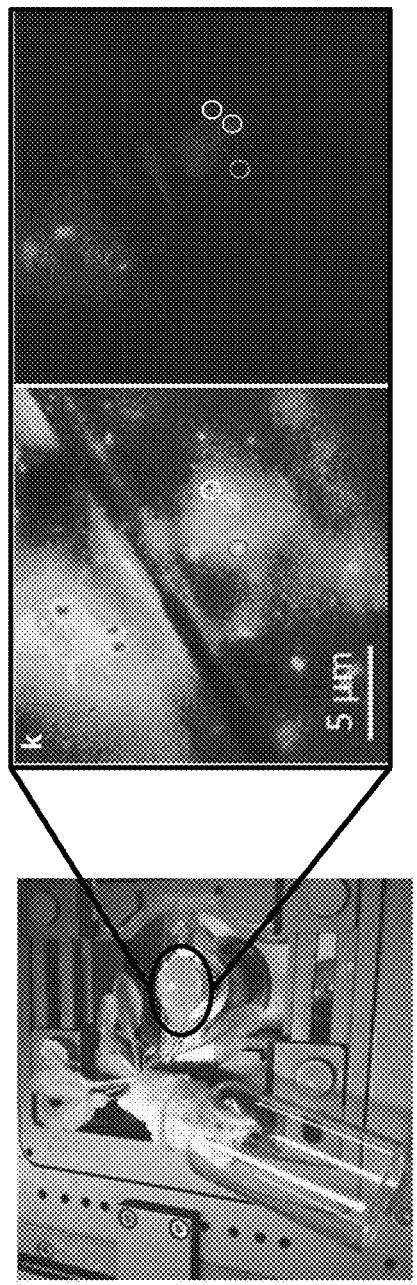
FIG. 22(a) includes an image of an in vivo plant setup and images obtained using the in vivo plant setup.
Figure 22B:
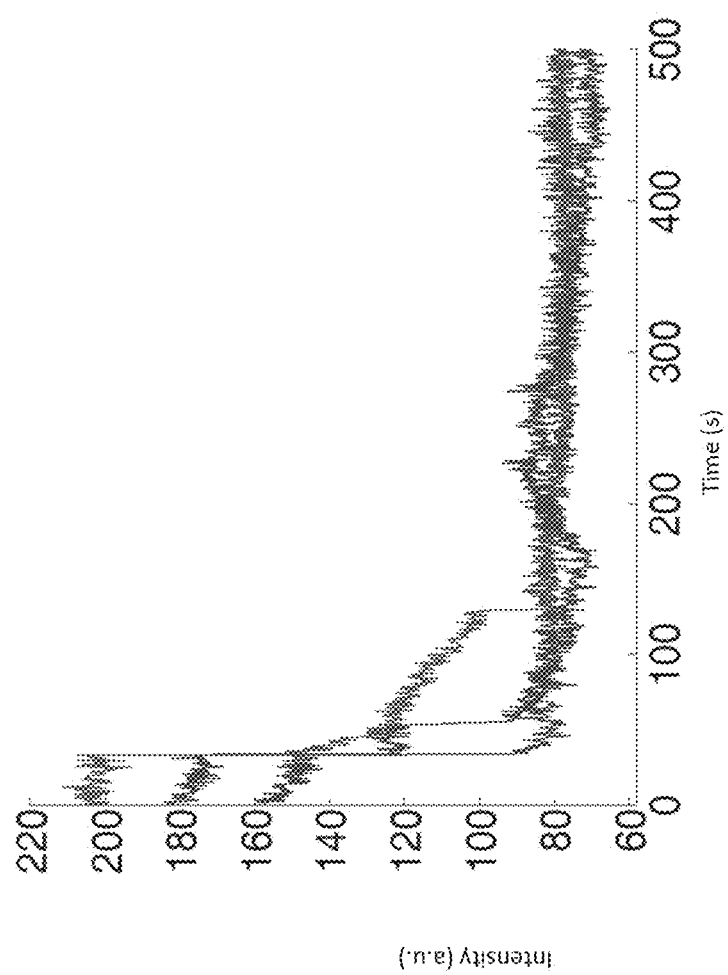
FIG. 22(b) is a graph representing the peak intensity time traces of the three nanoparticle regions indicated in FIG. 22(a).

SWNTs Enable Real-Time Free Radical Sensing Inside Extracted Chloroplasts and Leaves The ss(AT)$_{15}$-SWNTs have been examined as fluorescent detectors of nitric oxide (NO). (Kim, J.-H. et al. The rational design of nitric oxide selectivity in single-walled carbon nanotube near-infrared fluorescence sensors for biological detection. *Nat. Chem.* 1, 473-81 (2009), which is incorporated by reference in its entirety). (NO is a key signaling molecule found in chloroplasts and also an environmental pollutant. Wilson, I. D., Neill, S. J. & Hancock, J. T. Nitric oxide synthesis and signalling in plants. *Plant. Cell Environ.* 31, 622-31 (2008), which is incorporated by reference in its entirety). The ability to localize ss(AT)$_{15}$-SWNTs in chloroplasts can offer an opportunity to embed this real-time sensor of NO within the photosynthethic apparatus to monitor and control the degradation rate. The potential for nitric oxide detection in plants by ss(AT)$_{15}$-SWNTs was demonstrated (FIGS. 20-21). SWNT chiralities with a peak of emission above 1100 nm underwent a strong quenching in near-infrared fluorescence in the presence of dissolved nitric oxide in both extracted chloroplasts and leaves in vivo. Real-time imaging of free radical diffusion in a living plant using a SWNT-based sensor was performed (FIG. 22(a)). Near infrared images of the leaf lamina confirmed a steep reduction in SWNT sensor intensity upon perfusion of dissolved NO (FIG. 22(b)). The development of nanobionic leaves with novel sensing capabilities has the potential to create plant biochemical detectors for both endogenous signaling molecules and exogenous environmental compounds. The use of novel SWNT-based sensors can be used to detect other key molecules of interest within plants. The separation of single chirality SWNTs can enable the development of more robust sensors with multimodal responses for in vivo applications. (Tvrdy, K. et al. A Kinetic Model for the Deterministic Prediction of Gel-Based Carbon Nanotube Separation. ACS Nano 7, 1779-1789 (2013); and Heller, D. A. et al. Multimodal optical sensing and analyte specificity using single-walled carbon nanotubes. Nat. Nanotechnol. 4, (2009), each of which is incorporated by reference in its entirety).

SWNT Nitroaromatics Sensors

Nanotubes can be functionalized in different ways to serve as sensors for harmful compounds. Bombolitin is a unique peptide which allows for recognition of nitroaromatics, the key compounds in many explosives. See, Heller, D., Pratt, G. & Zhang, J., 2011. Peptide secondary structure modulates single-walled carbon nanotube fluorescence as a chaperone sensor for nitroaromatics. *Proceedings of the National Acadamy of Sciences U.S.A.*, 108(21), pp. 8544-8549, which is incorporated by reference in its entirety. Using bombolitin to coat carbon nanotubes results in stronger recognition and easily differentiable spectral shifts. The functionalization of the carbon nanotube surface can result in completely unique sites for recognition, resolvable at the single-molecule level. Airborne nitroaromatic molecules can enter a plant system alongside carbon dioxide and water vapor from the air. Any bombolitin-functionalized nanotubes infused into the leaves of the plant would recognize the nitroaromatics and would display a spectral shift upon change in the bombolitin's secondary structure. The modified plant can effectively act as a nitroaromatic-sensing plant. Such nanobionic plants do not rely upon genetic modification, and therefore the nitroaromatics-sensing function can be given to almost any plant. This technology can be applied to airports, hospitals, and other areas where security is a major concern. Indoor plants used for their aesthetic value in these locations can double as nitroaromatics sensors.

Developing stand-off devices for detecting the spectral shift would allow for this technology to become widespread. For example, a FLIR SC6200 nIR camera can be used to accomplish standoff detection of SWNT nIR emission. FIG. 53 shows that the FLIR SC6200 can be used to image 6.5 chirality SWNT suspended in SDS. FIG. 53A shows that the response of this camera can monitor emission from ~900 nm-1700 nm, which uses an InGaAs array. FIG. 53B shows a picture of the FLIR SC6200. FIG. 53C shows the nIR emission of a 532 nm 200 mW laser shining through a vial of water. FIG. 53D shows the nIR emission of a 532 nm 200 mW laser shining through a vial of 5 mg/L 6.5 SDS SWNT. This approach can be used to image semiconducting SWNT and SWNT-based sensors within plants from a distance of several meters and even from a satellite.

Glowing Plants Enabled by Silica Nanoparticle-Luciferase-Luciferin Complexes

Co-immobilization of luciferase and luciferin on mesoporous silica nanoparticles can make autoluminescent plants without the need of genetic engineering. Previously, luciferase and luciferin co-immobilized mesoporous silica nanoparticle materials have been reported for intracellular biocatalysis in Hela cells. See, Luciferase and Luciferin Co-immobilized Mesoporous Silica Nanoparticle Materials for Intracellular Biocatalysis, *J. Am. Chem. Soc.* 2011, 133, 18554-18557, which is incorporated by reference in its entirety. Immobilizing luciferase on silica nanoparticles with ATP in plant leaves can make the luminescence reactions to glow longer (16 h) than free luciferase (2-8 h) in both a tube test and a leaf.

Concentration of Materials (General)

Buffer (30 mM HEPES, 15 mM $MgCl_2$ at pH 7.8), luciferin (1 mM), ATP (3 mM; if added, depending on experiment), Luciferase (variable depending on experiment)

Example

HEPES (358 mg) and 71.4 mg $MgCl_2$ were dissolved in 50 mL DI water, then adjusted to pH 7.8 using KOH. ATP (15 mg) in amL of HEPES/$MgCl_2$ solution was prepared in a separate container. One milligram of luciferin was dissolved in 357 μL of HEPES/$MgCl_2$ solution. Three separate solutions, HEPES/$MgCl_2$:ATP:luciferin, added in 8:1:1 ratio.

Infiltration to Plant Leaves

HEPES/$MgCl_2$ buffer was prepared in 50 mL Falcon tube and adjust to pH 7.8, and 1 mL of buffer was mixed with 15 mg ATP in Eppendorf tube. After 357 μL of the buffer was added to dissolve luciferin, 800 μL of the buffer, 10 μL of luciferin solution, and desired amount of luciferase (free or silica nanoparticle-immobilized) solution were pipetted into Eppendorf tube. The solution without ATP was injected through the leaf lamina with a needleless syringe and luminescence was observed. After 10 μL of ATP was added to Eppendorf tube, the solution with ATP was injected into leaf and observe luminescence Immobilization of Luciferase on Silica Nanoparticle (SiNPs) SiNPs were Dispersed in Ethanol.

GPTS (0.5% v/v) was added to SiNPs suspension, acetic acid was added to adjust the pH of the reaction mixture to be about 4-5. The temperature was gradually increased up to 65° C. and the reaction was continued overnight with vigorous magnetic stirring. After washing the Si NPs with ethanol, PEG amine (1% v/v) was added, and the reaction was continued for 3-6 hours with vigorous magnetic stirring. After washing PEG-Si NPs with ethanol and DI water, PEG-Si NPs were dispersed in Tris-acetate buffer (50 mM, pH 7.4), and load luciferase. This reaction was kept in the fridge for 1.5 hour. Free luciferase was removed by washing with water several times.

Without the aid of silica nanoparticles, luminescence was observed after infiltration of the reaction mixture containing buffer, luciferase, luciferin and ATP to spinach leaves. Luminescence was observed with infiltration of the reaction mixture without ATP to spinach leaf, which meant ATP molecules inside of the spinach leaf participated in this reaction. Luminescence lasted for about an hour. When various plants (habanero, cucumber, cabbage, and spinach) were tested for this effect, only spinach and cucumber proved to be suitable plants that enough ATP existed for luciferin-luciferase reaction.

When silica nanoparticle luciferase complexes were introduced to spinach leaves, luminescence reactions can last longer (16 h) than free luciferase (2-8 h) in both a tube test and a leaf. For example, luciferase was embedded to PEG layers anchored on silica nanoparticles (50 nm-diameter), and luciferase immobilized silica nanoparticles (50 nm-diameter) showed luminescence in buffer containing luciferin, $Mg^{2+}$ and ATP. When it was infiltrated to the spinach leaf, bright luminescence was observed in the leaf. The luminescence of free luciferase-luciferin was brighter than that of immobilized luciferase on silica nanoparticles-luciferin in the beginning. The luminescence from free luciferase has been diminished quickly by 30 minutes, whereas, fluorescence from immobilized luciferase glowed for 6 hours with same intensity and extended total glowing time to 16 hours.

In sum, cationic or anionic nanoparticles may have the ability to passively transport and irreversibly localize within organelles, for example, the lipid envelope of extracted plant chloroplasts from *Spinacia oleracea* L. Internalized SWNT complexes within extracted chloroplasts can promote photosynthetic activity over three times higher than controls and can enhance maximum electron transport rates. SWNT chloroplast assemblies can enable higher rates of leaf electron transport in vivo via a proposed mechanism of augmented photoabsorption. Concentrations of reactive oxygen species inside extracted chloroplasts, such as superoxide, can be suppressed to 42% and 56% by delivering poly (acrylic acid) nanoceria and corresponding nanotube nanoceria complexes, respectively. SWNTs can also enable near infrared fluorescence monitoring of nitric oxide ex vivo and in vivo. Nanobionic engineering of plant function may contribute to the development of biomimetic materials for light-harvesting and biochemical detection with regenerative properties and enhanced efficiency.

Advantages of using nanoparticles with organelles or photosynthetic organisms can include (1) the ability to understand mechanisms of transport and spontaneous assembly of nanoparticles inside intact cells or organelles; (2) increased photosynthetic activity in chloroplasts via specific nanoparticle assemblies within photosynthetic machinery; (3) enhanced ability of the chloroplast to scavenge ROS using cerium oxide and carbon-based nanoparticles transported to optimal sites of ROS generation; and (4) real-time monitoring of free radical species and environmental pollutants using in vivo and ex vivo embedded nanosensors.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed:

1. An engineered chloroplast comprising:
    a coated nanoparticle having a zeta potential of less than 10 mV or greater than 10 mV and
    a lipid layer that surrounds coated nanoparticle in the chloroplast interior, the coated nanoparticle having the ability to passively transport and irreversibly localize within a chloroplast thylakoid membrane within seconds of nanoparticle interaction with the inner and outer lipid bilayer to enhance electron transport rates.

2. The composition of claim 1, wherein the nanoparticle includes a nanotube.

3. The composition of claim 1, wherein the nanoparticle includes a carbon nanotube.

4. The composition of claim 1, wherein the nanoparticle includes a single-walled carbon nanotube.

5. The composition of claim 1, wherein the nanoparticle includes cerium oxide.

6. The composition of claim 1, wherein the nanoparticle is conjugated with at least one cerium oxide nanoparticle.

7. The composition of claim 1, wherein the nanoparticle includes a polymer.

8. The composition of claim 7, wherein the polymer of the nanoparticle is cross-linked with at least one cerium oxide nanoparticle.

9. The composition of claim 7, wherein the polymer includes a polynucleotide.

10. The composition of claim 9, wherein the polynucleotide includes poly(AT).

11. The composition of claim 7, wherein the polymer includes a polysaccharide.

12. The composition of claim 11, wherein the polysaccharide is selected from the group consisting of dextran, pectin, hyaluronic acid, chitosan, and hydroxyethylcellulose.

13. The composition of claim 11, wherein the polysaccharide is chitosan.

14. The composition of claim 7, wherein the polymer includes poly(acrylic acid).

15. The composition of claim 1, wherein the nanoparticle is photoluminescent.

16. The composition of claim 1, wherein the nanoparticle emits near-infrared radiation.

17. The composition of claim 1, wherein the nanoparticle has a zeta potential of less than 20 mV or greater than 20 mV.

18. The composition of claim 1, wherein the nanoparticle has a zeta potential of less than −30 mV or greater than 30 mV.

19. The composition of claim 1, wherein the nanoparticle is photoluminescent and the photoluminescence emission of the photoluminescent nanoparticle is altered by a change in a stimulus within the organelle.

20. The composition of claim 19, wherein the stimulus is the concentration of an analyte.

21. The composition of claim 20, wherein the analyte is a reactive oxygen species.

22. The composition of claim 20, wherein the analyte is nitric oxide.

23. The composition of claim 20, wherein the analyte is carbon dioxide.

24. The composition of claim 20, wherein the analyte is adenosine triphosphate.

25. The composition of claim 20, wherein the analyte is nicotinamide adenine dinucleotide phosphate.

26. The composition of claim 20, wherein the analyte is oxygen.

27. The composition of claim 19, wherein the stimulus is the pH of the organelle.

28. The composition of claim 1, wherein the nanoparticle is a semiconductor.

29. A green plant including the composition of claim 1.

* * * * *